United States Patent
Grammenos et al.

(10) Patent No.: US 8,299,262 B2
(45) Date of Patent: Oct. 30, 2012

(54) PYRIDYLMETHYL-SULFONAMIDE COMPOUNDS

(75) Inventors: Wassilios Grammenos, Ludwigshafen (DE); Jan Klaas Lohmann, Ludwigshafen (DE); Thomas Grote, Wachenheim (DE); Jochen Dietz, Karlsruhe (DE); Bernd Mueller, Frankenthal (DE); Michael Puhl, Lampertheim (DE); Jens Renner, Bad Duerkheim (DE); Sarah Ulmschneider, Bad Duerkheim (DE); Marianna Vrettou, Mannheim (DE); Joachim Rheinheimer, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 163 days.

(21) Appl. No.: 12/746,086

(22) PCT Filed: Nov. 21, 2008

(86) PCT No.: PCT/EP2008/065958
§ 371 (c)(1),
(2), (4) Date: Jun. 3, 2010

(87) PCT Pub. No.: WO2009/071448
PCT Pub. Date: Jun. 11, 2009

(65) Prior Publication Data
US 2010/0249077 A1 Sep. 30, 2010

(30) Foreign Application Priority Data

Dec. 5, 2007 (EP) .................................. 07122415
Feb. 29, 2008 (EP) .................................. 08102193

(51) Int. Cl.
*C07D 213/62* (2006.01)
*A61K 31/44* (2006.01)

(52) U.S. Cl. ........................ 546/294; 514/347

(58) Field of Classification Search ................ None
See application file for complete search history.

(56) References Cited

U.S. PATENT DOCUMENTS

| 7,799,915 | B2* | 9/2010 | Sum et al. ........... 544/330 |
| 2006/0014945 | A1 | 1/2006 | Galley et al. |
| 2006/0293314 | A1 | 12/2006 | Grammenos et al. |
| 2008/0221177 | A1 | 9/2008 | Grammenos et al. |
| 2010/0069243 | A1 | 3/2010 | Lohmann et al. |

FOREIGN PATENT DOCUMENTS

| EP | 1 103 543 | 5/2001 |
| WO | WO 01/70229 | 11/2001 |
| WO | WO 2004/072070 | 8/2004 |
| WO | WO 2004/096366 | 11/2004 |
| WO | WO 2005/033081 | 4/2005 |
| WO | WO 2005/040120 | 5/2005 |
| WO | WO 2005/040165 | 5/2005 |
| WO | WO 2005/054243 | 6/2005 |
| WO | WO 2006/021403 | 3/2006 |
| WO | WO 2006/097488 | 9/2006 |
| WO | WO 2006/097489 | 9/2006 |
| WO | WO 2007/104726 | 9/2007 |

OTHER PUBLICATIONS

Silverman, R. "The Organic Chemistry of Drug Design and Drug Action," 2004, Elsevier, pp. 29-32.*
International Search Report prepared in International Application No. PCT/EP2008/065958, filed Nov. 21, 2008.
English language translation of the International Preliminary Report on Patentability from corresponding International Application No. PCT/EP2008/065958, filed Nov. 21, 2008.
Brana, M.F. et al., "Synthesis of N, N'-Bis(phenylsulfonyl)-1,2-bis(4-pyridyl)ethylenediamines", Liebigs Annalen Der Chemie, 1990, pp. 641-645.
Zhang, Ying-Ying et al., "N-Benzyl-2-nitro-N-(4-pyridylmethyl)-benzene-sulfonamide", Acta Crystallographica, Section E, 2007, pp. 1285-1286, vol. E63, No. 3.
Zificsak, Craig et al., "Synthesisi of 2-(α-substituted-amidoalkyl)-imidazoles", Tetrahedron Letters, Jul. 11, 2005, pp. 4789-4792, vol. 46, No. 28, Elsevier, Amsterdam.

* cited by examiner

*Primary Examiner* — Janet Andres
*Assistant Examiner* — Heidi Reese
(74) *Attorney, Agent, or Firm* — Brinks Hofer Gilson & Lione

(57) ABSTRACT

The present invention relates to novel pyridylmethyl-sulfonamide compounds of formula (I)

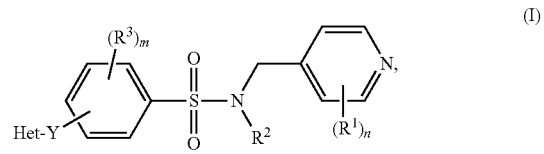

where: n is 0 to 4; m is 0 to 4; $R^1$ is halogen, CN, $NO_2$, OH, SH, $C_1$-$C_4$-alkyl, $C_1$-$C_4$-haloalkyl, $C_1$-$C_4$-alkoxy, $C_1$-$C_4$-haloalkoxy, etc.; and/or two radicals $R^1$ together form a fused ring; $R^2$ is H, $C_1$-$C_4$-alkyl, $C_1$-$C_4$-haloalkyl, $C_2$-$C_4$-alkenyl, $C_2$-$C_4$-alkynyl, $C_3$-$C_8$-cycloalkyl, $C_1$-$C_4$-alkyl-$C_3$-$C_8$-cycloalkyl or benzyl; $R^3$ is halogen, CN, $NO_2$, $C_1$-$C_4$-alkyl, $C_1$-$C_4$-haloalkyl, $C_1$-$C_4$-alkoxy or $C_1$-$C_4$-haloalkoxy; Y is —O—, $C_1$-$C_4$-alkanediyl, —O—$CH_2$—, —$CH_2$—O—, —C(NOR″)—, —S—, —S(=O)—, —S(=O)$_2$— or —N(R″)—;

and the N-oxides, and salts thereof and their use for combating phytopathogenic harmful fungi, and also to compositions and seed comprising at least one such compound.

16 Claims, No Drawings

PYRIDYLMETHYL-SULFONAMIDE COMPOUNDS

This application is a National Stage application of International Application No. PCT/EP2008/065958 filed Nov. 21, 2008, the entire contents of which is hereby incorporated herein by reference. This application also claims the benefit under 35 U.S.C. §119 of European Patent Application Nos. 07122415.8 and 08102193.3 filed Dec. 5, 2007 and Feb. 29, 2008, the entire contents of each are hereby incorporated herein by reference.

The present invention relates to novel pyridylmethyl-sulfonamide compounds and the N-oxides, and salts thereof and their use for combating phytopathogenic harmful fungi, and also to compositions and seed comprising at least one such compound.

WO 05/033081 describes 4-pyridylmethyl sulfonamide compounds of formula

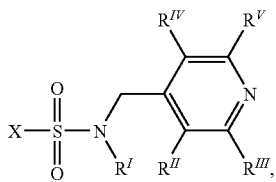

wherein X inter alia may represent an unsubstituted or substituted biphenyl ether, and the use of such compounds against plant pathogenic fungi. With respect to their fungicidal activity, some of said 4-pyridylmethyl sulfonamide are unsatisfactory, or they have unwanted properties such as low crop plant compatibility.

WO 06/097489 describes various 4-pyridylmethylamides of biphenylsulfonic acid, wherein the biphenyl moiety may carry substituents at the phenyl ring of the biphenyl moiety at the sulfonamide group. The compounds are used for combating arthropodal pests and for protecting materials against infestation and/or destruction by said pests.

WO 07/104,726 describes specific quinoline methylsulfonamides carrying a biphenyl moiety at the sulfonamide group wherein the phenylene moiety of biphenyl is unsubstituted.

Based on this, there is ongoing need to provide compounds which are useful for combating phytopathogenic harmful fungi.

This object is, surprisingly, achieved by pyridylmethyl-sulfonamide compounds of formula (I) as defined herein and by the N-oxides and their salts, in particular the agriculturally acceptable salts.

Accordingly, the present invention relates to pyridylmethyl-sulfonamide compounds of formula (I) and the N-oxides, the salts, in particular the agriculturally acceptable salts, thereof

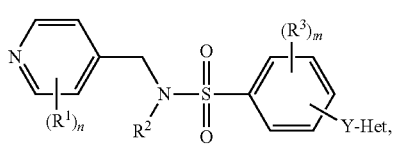

where:

n indicates the number of substituents $R^1$ on the pyridine ring and n is 0, 1, 2, 3 or 4;

m indicates the number of substituents $R^3$ on the phenyl ring and m is 0, 1, 2, 3 or 4;

$R^1$ is halogen, CN, $NO_2$, OH, SH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, $C_2$-$C_4$-alkenyl, $C_2$-$C_4$-alkynyl, $C_3$-$C_8$-cycloalkyl or $C_1$-$C_4$-alkyl-$C_3$-$C_8$-cycloalkyl; and/or two radicals $R^1$ that are bound to adjacent carbon atoms of the pyridine ring may form together with said carbon atoms a fused benzene ring, a fused saturated or partially unsaturated 5-, 6-, or 7-membered carbocycle or a fused 5-, 6-, or 7-membered heterocycle containing 1, 2 or 3 heteroatoms selected from the group consisting of 2 nitrogen, 1 oxygen and 1 sulfur atoms as ring members, it being possible for the fused ring to carry 1 or 2 radicals selected from the group consisting of halogen, $C_1$-$C_4$-alkyl, halomethyl, $C_1$-$C_4$-alkoxy and halomethoxy, it being possible for n=2, 3 or 4 that $R^1$ are identical or different;

$R^2$ is hydrogen, $C_1$-$C_4$-alkyl, $C_1$-$C_4$-haloalkyl, $C_2$-$C_4$-alkenyl, $C_2$-$C_4$-alkynyl, $C_3$-$C_8$-cycloalkyl, $C_1$-$C_4$-alkyl-$C_3$-$C_8$-cycloalkyl or benzyl wherein the phenyl moiety of benzyl is unsubstituted or carries 1, 2, 3, 4, or 5 substituents selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl;

$R^3$ is halogen, CN, $NO_2$, $C_1$-$C_4$-alkyl, $C_1$-$C_4$-haloalkyl, $C_1$-$C_4$-alkoxy or $C_1$-$C_4$-haloalkoxy, it being possible for m=2, 3 or 4 that $R^2$ are identical or different;

Y is a divalent group selected from —O—, $C_1$-$C_4$-alkanediyl, —O—$CH_2$—, —$CH_2$—O—, —C(NOR″)—, —S—, —S(=O)—, —S(=O)$_2$— and —N(R″)—, wherein R″ is hydrogen or $C_1$-$C_4$-alkyl and wherein the $C_1$-$C_4$-alkanediyl moiety is unsubstituted or carries 1 or 2 substituents selected from the group consisting of oxo, cyano, halogen, $C_1$-$C_4$-alkyl, $C_1$-$C_4$-alkoxy, $C_1$-$C_4$-haloalkyl and $C_1$-$C_4$-haloalkoxy;

Het is a 5- or 6-membered heteroaromatic radical, wherein the ring member atoms of the heteroaromatic radical include, besides carbon atoms 1, 2, 3 or 4 nitrogen atoms, or 1 oxygen atom and 0, 1 or 2 nitrogen atoms or 1 sulfur atom and 0, 1 or 2 nitrogen atoms and wherein the heteroaromatic radical is unsubstituted or carries 1, 2, 3 or 4 identical or different substituents $R^a$, wherein two radicals $R^a$ that are bound to adjacent ring member atoms may form a fused 5- or 6-membered carbocycle or heterocycle, wherein the fused carbocycle or heterocycle is unsubstituted or carries 1, 2, 3 or 4 identical or different substituents $R^b$;

$R^a$ is halogen, CN, $NO_2$, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_1$-$C_4$-alkylthio, $C_1$-$C_4$-alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, a radical C(=O)R, wherein R is H, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkoxy, $C_1$-$C_4$-haloalkoxy, amino, $C_1$-$C_4$-alkylamino or di($C_1$-$C_4$-alkyl)amino, a radical CR'(=NOR"), wherein R' is H or $C_1$-$C_4$-alkyl, and R" is $C_1$-$C_4$-alkyl, $C_1$-$C_4$-haloalkyl, $C_2$-$C_4$-alkenyl, $C_2$-$C_4$-alkynyl or $C_1$-$C_4$-alkoxy-$C_1$-$C_4$-alkyl, phenyl, pyridinyl, pyrimidinyl, phenoxy or phenoxyalkyl, where the five last mentioned radicals are unsubstituted or carry 1, 2, 3 or 4 identical or different substituents $R^c$;

$R^b$ and $R^c$ independently of each other are selected from halogen, CN, $NO_2$, OH, SH, $C_1$-$C_4$-alkyl, $C_1$-$C_4$-haloalkyl, $C_1$-$C_4$-alkoxy and $C_1$-$C_4$-haloalkoxy.

The present invention furthermore relates to a process and intermediates for preparing the pyridylmethyl-sulfonamide compounds of formula (I).

The present invention furthermore relates to intermediates such as compounds of formulae (II), (III), (IV) and (V).

The present invention furthermore relates to an agricultural composition which comprises a solvent or solid carrier and at least one compound of formula (I) or an N-oxide or an agriculturally acceptable salt thereof.

The compounds of the present invention are useful for combating phytopathogenic harmful fungi. Therefore the present invention furthermore relates to a method for combating phytopathogenic harmful fungi, which process comprises treating the fungi or the materials, plants, the soil or seeds to be protected against fungal attack, with an effective amount of at least one compound of formula (I) or an of an N-oxide or an agriculturally acceptable salt thereof.

Furthermore, the present invention also relates to seed comprising a compound of formula (I), or an N-oxide or an agriculturally acceptable salt thereof, as defined in any of claims 1 to 17, in an amount of from 0.1 g to 10 kg per 100 kg of seed.

Depending on the substitution pattern, the compounds (I) and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds of formula (I).

The term "compounds (I)" refers to compounds of formula (I). Likewise, this terminology applies to all subformulae, such as (I.1), (I.1A), (I.1B) or (I.1G), herein.

In the definitions of the variables given above, collective terms are used which are generally representative for the substituents in question. The term $C_n$-$C_m$ indicates the number of carbon atoms possible in each case in the substituent or substituent moiety in question.

The term "halogen" refers to fluorine, chlorine, bromine and iodine.

The term "oxo" refers to a double-bonded oxygen atom (=O).

The term "$C_1$-$C_4$-alkyl" refers to a straight-chained or branched saturated hydrocarbon group having 1 to 4 carbon atoms, for example methyl, ethyl, propyl, 1-methylethyl, butyl, 1-methylpropyl, 2-methylpropyl, and 1,1-dimethylethyl.

The term "$C_1$-$C_4$-haloalkyl" refers to a straight-chained or branched alkyl group having 1 to 4 carbon atoms, wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-fluoromethyl-2-fluoroethyl, 1-(chloromethyl)-2-chloroethyl, 1-bromomethyl-2-bromoethyl, 4-fluorobutyl, 4-chlorobutyl, 4-bromobutyl or nonafluorobutyl, and the like.

The term "$C_1$-$C_4$-alkoxy" refers to a straight-chain or branched alkyl group having 1 to 4 carbon atoms which is bonded via an oxygen, at any position in the alkyl group, e.g. methoxy, ethoxy, n-propoxy, 1-methylethoxy, butoxy, 1-methylpropoxy, 2-methylpropoxy or 1,1-dimethylethoxy.

The term "$C_1$-$C_4$-haloalkoxy" refers to a $C_1$-$C_4$-alkoxy radical as defined above, wherein some or all of the hydrogen atoms in these groups may be replaced by halogen atoms as mentioned above, e.g., $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "$C_1$-$C_4$-alkoxy-$C_1$-$C_4$-alkyl" refers to alkyl having 1 to 4 carbon atoms, wherein one hydrogen atom of the alkyl radical is replaced by a $C_1$-$C_4$-alkoxy group.

The term "$C_1$-$C_4$-alkoxy-$C_1$-$C_4$-alkoxy" refers to an $C_1$-$C_4$-alkoxy-$C_1$-$C_4$-alkyl group, which is bonded via an oxygen atom to the remainder of the molecule.

The term "$C_1$-$C_4$-alkylthio" as used herein refers to straight-chain or branched alkyl groups having 1 to 4 carbon atoms bonded through a sulfur atom, at any position in the alkyl group, for example methylthio, ethylthio, propylthio, isopropylthio, and n-butylthio.

Accordingly, the term "$C_1$-$C_4$-haloalkylthio" as used herein refers to straight-chain or branched haloalkyl groups having 1 to 4 carbon atoms bonded through a sulfur atom, at any position in the haloalkyl group.

The term "$C_1$-$C_4$-alkylsulfinyl" refers to straight-chain or branched alkyl group having 1 to 4 carbon atoms bonded through a —S(=O)— moiety, at any position in the alkyl group, for example methylsulfinyl and the like.

Accordingly, the term "$C_1$-$C_4$-haloalkylsulfinyl" refers to straight-chain or branched haloalkyl group having 1 to 4 carbon atoms bonded through a —S(=O)— moiety, at any position in the haloalkyl group.

The term "$C_1$-$C_4$-alkylsulfonyl" refers to straight-chain or branched alkyl group having 1 to 4 carbon atoms bonded through a —S(=O)$_2$— moiety, at any position in the alkyl group, for example methylsulfonyl.

Accordingly, the term "$C_1$-$C_4$-haloalkylsulfonyl" refers to straight-chain or branched haloalkyl group having 1 to 4 carbon atoms bonded through a —S(=O)$_2$— moiety, at any position in the haloalkyl group.

The term "$C_1$-$C_4$-alkylamino" refers to an amino radical carrying one $C_1$-$C_4$-alkyl group as substituent, for example methylamino, ethylamino, propylamino, 1-methylethylamino, butylamino, 1-methylpropylamino, 2-methylpropylamino, 1,1-dimethylethylamino and the like.

The term "di($C_1$-$C_4$-alkyl)amino" refers to an amino radical carrying two identical or different $C_1$-$C_4$-alkyl groups as substituents, for example dimethylamino, diethylamino, di-n-propylamino, diisopropylamino, N-ethyl-N-methylamino, N-(n-propyl)-N-methylamino, N-isopropyl-N methylamino, N-(n-butyl)-N-methylamino, N-(n-pentyl)-N-methylamino, N-(2-butyl)-N methylamino, N-isobutyl-N-methylamino, and the like.

The term "($C_1$-$C_4$-alkoxy)carbonyl" refers to a $C_1$-$C_4$-alkoxy radical which is attached via a carbonyl group.

The term "di($C_1$-$C_4$-alkyl)aminocarbonyl" refers to a di($C_1$-$C_4$)alkylamino radical which is attached via a carbonyl group.

The term "$C_2$-$C_4$-alkenyl" refers to a branched or unbranched unsaturated hydrocarbon radical having 2 to 4 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_4$-alkynyl" refers to a branched or unbranched unsaturated hydrocarbon radical having 2 to 4 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_1$-$C_4$-alkyl-$C_3$-$C_8$-cycloalkyl" refers to a cycloalkyl radical having 3 to 8 carbon atoms, wherein one hydrogen atom of the cycloalkyl radical is replaced by a $C_1$-$C_4$-alkyl group.

The term "5-, 6- or 7-membered carbocycle" is to be understood as meaning both saturated and partially unsaturated carbocycles having 5, 6 or 7 ring members as well as phenyl. Examples for non-aromatic rings include cyclopentyl, cyclopentenyl, cyclopentadienyl, cyclohexyl, cyclohexenyl, cyclohexadienyl, cycloheptyl, cycloheptenyl, cycloheptadienyl and the like.

The term "5-, 6-, or 7-membered heterocycle" which contains one, two, three or four heteroatoms from the group consisting of O, N and S, is to be understood as meaning both saturated and partially unsaturated as well as aromatic heterocycles having 5, 6 or 7 ring atoms. Examples include:

saturated and partially unsaturated 5-, 6-, or 7-membered heterocycle which contains 1, 2 or 3 nitrogen atoms and/or one oxygen or sulfur atom or 1 or 2 oxygen and/or sulfur atoms, and which is saturated or partially unsaturated, for example 2-tetrahydrofuranyl, 3-tetrahydrofuranyl, 2-tetrahydrothienyl, 3-tetrahydrothienyl, 2 pyrrolidinyl, 3-pyrrolidinyl, 3-isoxazolidinyl, 4-isoxazolidinyl, 5-isoxazolidinyl, 3 isothiazolidinyl, 4-isothiazolidinyl, 5-isothiazolidinyl, 3-pyrazolidinyl, 4-pyrazolidinyl, 5 pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3 hexahydropyridazinyl, 4-hexahydropyridazinyl, 2-hexahydropyrimidinyl, 4 hexahydropyrimidinyl, 5-hexahydropyrimidinyl and 2-piperazinyl;

5-membered aromatic heterocyclyl (heteroaromatic radical) which contains 1, 2, 3 or 4 nitrogen atoms or 1, 2 or 3 nitrogen atoms and one sulfur or oxygen atom: 5-membered heteroaryl groups which, in addition to carbon atoms, may contain 1 to 4 nitrogen atoms or one to three nitrogen atoms and one sulfur or oxygen atom as ring members, for example 2-thienyl, 3-thienyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl and 1,3,4-triazol-2-yl;

6-membered heterocycyl (heteroaromatic radical) which contains 1, 2, 3 or 4 nitrogen atoms: 6 membered heteroaryl groups which, in addition to carbon atoms, may contain 1, 2, 3 or 4 nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "$C_1$-$C_4$-alkanediyl" refers to a divalent, branched or straight-chain saturated hydrocarbon radical having 1 to 4 carbon atoms, derived from a $C_1$-$C_4$-alkyl group (as defined above) that has two points of attachment.

The term "two radicals $R^1$ that are bound to adjacent carbon atoms of the pyridine ring may form together with said carbon atoms a fused ring" refers to a bicyclic ring system, wherein pyridin-4-yl carries a fused-on 5-, 6- or 7-membered carbocyclic or heterocyclic ring. Examples of such fused bicyclic ring systems include benzo[b]pyridine (quinoline), pyrido[2,3-b]pyridine (1,8-naphthyridine), pyrido[3,4-b]pyridine (1,7-naphthyridine), pyrido[4,3-b]pyridine (1,6-naphthyridine), pyrido[3,2-b]pyridine (1,5-naphthyridine), pyrido[2,3-d]pyrimidine, pyrido[3,2-d]pyrimidine, pyrido[2,3-b]furane, pyrido[3,2-b]furane, pyrido[2,3-c]furane, pyrido[2,3-d]thiazole, pyrido[3,2-d]thiazole, pyrido[2,3-d]isoxazole, pyrido[3,2-d]isoxazole, pyrido[2,3-c]isoxazole and pyrido[3,2-c]isoxazole.

The fused-on ring can be unsubstituted or substituted by 1, 2, 3 radicals substituents selected, independently from one another, from the group consisting of halogen, $C_1$-$C_4$-alkyl, halomethyl, $C_1$-$C_4$-alkoxy and halomethoxy.

The term "two radicals $R^a$ that are bound to adjacent carbon atoms of the Het group may form together with said carbon atoms a fused ring" refers to a bicyclic ring system, wherein Het, carries a fused-on 5-, 6- or 7-membered carbocyclic or heterocyclic ring. Examples of such fused bicyclic rings include quinoline, quinazoline, benzofurane, isobenzofurane, phthalazine, cinnoline, quinoxaline, benzothiazole, benzoisothiazole, benzoxazole, benzoisoxazole, 1,5-naphthyridine, 1,6-naphthyridine, 1,7-naphthyridine, 1,8-naphthyridine, 2,6-naphtyridine, 2,7-naphtyridine, pyrido[2,3-d]pyrimidine, pyrido[3,2-d]pyrimidine, pyrido[3,4-d]pyrimidine, pyrido[4,3-d]pyrimidine, pyrido[2,3-b]-furane, pyrido[3,2-b]furane, pyrido[2,3-c]furane, pyrido[3,4-b]furane, pyrido[4,3-b]-furane, pyrido[3,4-c]furane, pyrido[2,3-d]thiazole, pyrido[3,2-d]thiazole, pyrido[3,4-d]-thiazole, pyrido[4,3-d]thiazole, pyrido[2,3-d]isoxazole, pyrido[3,2-d]isoxazole, pyrido[2,3-c]isoxazole, pyrido[3,2-c]isoxazole, pyrido[3,4-d]isoxazole, pyrido[4,3-d]isoxazole, pyrido[3,4-c]isoxazole, pyrido[4,3-c]isoxazole and the like. The fused-on ring can be unsubstituted or substituted by 1, 2, 3 or 4 radicals substituents selected, independently from one another, from the group consisting of halogen, cyano, nitro, OH, SH, $C_1$-$C_4$-alkyl, $C_1$-$C_4$-haloalkyl, $C_1$-$C_4$-alkoxy and $C_1$-$C_4$-haloalkoxy.

Agriculturally acceptable salts of the compounds (I) encompass especially the salts of those cations or the acid addition salts of those acids whose cations and anions, respectively, have no adverse effect on the fungicidal action of the compounds (I).

Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry 1 to 4 $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound (I) with an acid of the corresponding anion, preferably of hydrochloric acid, hydrobromic acid, sulfuric acid, phosphoric acid or nitric acid.

Preference is given to those compounds (I) and where applicable also to intermediates, e.g. compounds (II) and (III), and to compounds of all sub-formulae provided herein, e.g. formula (I.1) or formulae (I.1A), (I.1B) or (I.1G), wherein the variables n, m, Y, $R^1$, $R^2$, $R^3$, and Het have independently of each other or more preferably in combination the following meanings:

Preference is given to compounds (I), in which Het is selected from pyridinyl, pyrimidinyl, pyridazinyl, pyrazinyl, thiazolyl, oxazolyl, isothiazolyl, isoxazolyl, thienyl, furyl, 1,3,5-triazinyl, 1,2,4-triazinyl, thiadiazolyl, 1,2,3-triazolyl, 1,2,4-triazolyl, pyrazolyl, imidazolyl, where the aforementioned heteroaromatic radicals are unsubstituted or carry 1, 2, 3 or 4 substituents $R^a$ being identical or different.

Particular preference is given to compounds (I), in which Het is selected from pyridinyl, pyrimidinyl, pyridazinyl, pyrazinyl, thiazolyl, 1,3,5-triazinyl and 1,2,4-triazinyl, where the aforementioned heteroaromatic radicals are unsubstituted or carry 1 or 2 substituents $R^a$ being identical or different.
Preference is also given to compounds (I), wherein Het carries 1, 2, 3 or 4 radicals $R^a$ which are selected from F, Cl, Br, CN, $C_1$-$C_2$-alkylsulfonyl, $C_1$-$C_2$-alkoxycarbonyl, aminocarbonyl, $C_1$-$C_2$-alkylaminocarbonyl, di($C_1$-$C_2$-alkyl)aminocarbonyl, $C_1$-$C_2$-alkoxy, $C_1$-$C_2$-alkyl, $CF_3$, $CHF_2$, $OCF_3$ and $OCHF_2$.

Particular preference is given to compounds (I), wherein Het carries 1 or 2 radicals $R^a$ selected from F, Cl, Br, $CH_3$, $OCH_3$, $CF_3$, $CHF_2$, $OCF_3$ and $OCHF_2$.

Even more preference is given to compounds (I), wherein Het carries 1 or 2 radicals $R^a$ selected from F, Cl, Br, $CH_3$, $OCH_3$ and $CF_3$.

Preference is likewise given to compounds (I), wherein two radicals $R^a$ that are bound to adjacent ring member atoms form a fused 5- or 6-membered carbocycle or heterocycle selected from benzene, pyridine, pyrimidine, furane, thiazole and isoxazole, wherein the fused carbocycle or heterocycle is unsubstituted or carries 1, 2, 3 or 4 identical or different substituents $R^b$, as defined above.

In the case that two radicals $R^a$ that are bound to adjacent ring member atoms form a fused 5- or 6-membered carbocycle or heterocycle, particular preference is given to compounds (I), wherein the two radicals $R^a$ form a fused benzene ring.

Preference is also given to compounds (I), wherein the moiety Het-Y is located on the phenyl ring in the meta- or para-position with respect to the sulfonyl group.

Particular preference is given to compounds (I), wherein the moiety Het-Y is located on the phenyl ring in the para-position with respect to the sulfonyl group. In one preferred embodiment the group Het of the compounds (I) is pyridin-2-yl, which is unsubstituted or carries 1 or 2 radicals $R^a$.

Examples of compounds (I) are those, wherein Het is pyridin-2-yl are 3-trifluoromethylpyridin-2-yl, 5-trifluoromethylpyridin-2-yl, 4-trifluoromethylpyridin-2-yl, 3-chloropyridin-2-yl, 5-chloropyridin-2-yl, 4-chloropyridin-2-yl, 3-bromopyridin-2-yl, 5-bromopyridin-2-yl, 4-bromopyridin-2-yl, 3-trichloromethylpyridin-2-yl, 5-trichloromethylpyridin-2-yl, 4-trichloromethylpyridin-2-yl, 3-cyanopyridin-2-yl, 5-cyanopyridin-2-yl, 4-cyanopyridin-2-yl, 3-nitropyridin-2-yl, 5-nitropyridin-2-yl, 4-nitropyridin-2-yl, 3-methylsulfonylpyridin-2-yl, 5-methylsulfonylpyridin-2-yl, 4-methylsulfonylpyridin-2-yl, 3-ethylsulfonylpyridin-2-yl, 5-ethylsulfonylpyridin-2-yl, 4-ethylsulfonylpyridin-2-yl, 3-methoxycarbonylpyridin-2-yl, 5-methoxycarbonylpyridin-2-yl, 4-methoxycarbonylpyridin-2-yl, 5-aminocarbonylpyridin-2-yl, 4-aminocarbonylpyridin-2-yl, 3-aminocarbonylpyridin-2-yl, 5-N-methylaminocarbonylpyridin-2-yl, 4-N-methylaminocarbonylpyridin-2-yl, 3-N-methylaminocarbonylpyridin-2-yl, 3-methoxypyridin-2-yl, 3-ethoxypyridin-2-yl, 3-difluoromethoxypyridin-2-yl, 5-methoxypyridin-2-yl, 5-ethoxypyridin-2-yl, 5-difluoromethoxypyridin-2-yl, 3-chloro-5-trifluoromethylpyridin-2-yl, 3-fluoro-5-trifluoromethylpyridin-2-yl, 3-bromo-5-trifluoromethylpyridin-2-yl, 3-methyl-5-trifluoromethylpyridin-2-yl, 3-ethyl-5-trifluoromethylpyridin-2-yl, 3-chloro-5-difluoromethoxypyridin-2-yl, 3-fluoro-5-difluoromethoxypyridin-2-yl, 3-methyl-5-difluoromethoxypyridin-2-yl, 3-chloro-5-trichloromethylpyridin-2-yl, 3-fluoro-5-trichloromethylpyridin-2-yl, 3-chloro-5-cyanopyridin-2-yl, 3-fluoro-5-cyanopyridin-2-yl, 3-methyl-5-cyanopyridin-2-yl, 3-ethyl-5-cyanopyridin-2-yl, 3-chloro-5-nitropyridin-2-yl, 3-chloro-5-methoxycarbonylpyridin-2-yl, 3-chloro-5-aminocarbonylpyridin-2-yl, 3-chloro-5-methylaminocarbonylpyridin-2-yl, 3-fluoro-5-nitropyridin-2-yl, 3-fluoro-5-methoxycarbonylpyridin-2-yl, 3-fluoro-5-aminocarbonylpyridin-2-yl, 3-fluoro-5-methylaminocarbonylpyridin-2-yl, 4-chloro-5-trifluoromethylpyridin-2-yl, 4-fluoro-5-trifluoromethylpyridin-2-yl, 4-bromo-5-trifluoromethylpyridin-2-yl, 4-methyl-5-trifluoromethylpyridin-2-yl, 4-chloro-5-nitropyridin-2-yl, 4-chloro-5-cyanopyridin-2-yl, 3-chloro-6-trifluoromethylpyridin-2-yl, 3-fluoro-6-trifluoromethylpyridin-2-yl, 3-methyl-6-trifluoromethylpyridin-2-yl, 4-chloro-5-difluoromethoxypyridin-2-yl, 4-fluoro-5-difluoromethoxypyridin-2-yl, 3-chloro-5-bromopyridin-2-yl, 3,5-dichloropyridin-2-yl, 3,5-difluoropyridin-2-yl, 3,5-dibromopyridin-2-yl, 3-methyl-5-chloropyridin-2-yl, 3-methyl-5-fluoropyridin-2-yl, 3-methyl-5-bromopyridin-2-yl, 3-methoxy-5-trifluoromethylpyridin-2-yl, 3-methoxy-5-cyanopyridin-2-yl, 3-methoxy-5-nitropyridin-2-yl, 3-methoxy-5-difluoromethoxypyridin-2-yl, 3-ethoxy-5-trifluoromethylpyridin-2-yl, 3-ethoxy-5-cyanopyridin-2-yl, 3-ethoxy-5-nitropyridin-2-yl, 3-ethoxy-5-difluoromethoxypyridin-2-yl, 3-chloro-4-methyl-5-trifluoromethylpyridin-2-yl and 3,4-dichloro-5-trifluoromethylpyridin-2-yl.

In another preferred embodiment the group Het of the compounds (I) is selected from 2-pyrimidinyl, 3-pyrimidinyl, 4-pyrimidinyl, 3-pyridyl, 2-thiazolyl, 2-pyrazinyl, 3-pyridazinyl, 1,3,5-triazin-2-yl, and 1,2,4-triazin-3-yl, where the aforementioned heteroaromatic radicals are unsubstituted or carry 1, 2, 3 or 4 identical or different substituents $R^a$.

Examples of compounds (I) are those, wherein Het is selected from 2-pyrimidinyl, 3-pyrimidinyl, 4-pyrimidinyl, 3-pyridyl, 2-thiazolyl, 2-pyrazinyl, 3-pyridazinyl, 1,3,5-triazin-2-yl, and 1,2,4-triazin-3-yl are 2-pyrimidinyl, 4-trifluoromethylpyrimidin-2-yl, 5-trifluoromethylpyrimidin-2-yl, 2-trifluoromethylpyrimidin-4-yl, 2-trifluoromethylpyrimidin-5-yl, 4-trifluoromethylpyrimidin-6-yl, 4-cyanopyrimidin-2-yl, 5-cyanopyrimidin-2-yl, 4-(1,1,1-trifluoroethoxy)pyrimidin-2-yl, 5-chloro-6-trifluoromethylpyrimidin-4-yl, 5-fluoro-6-trifluoromethylpyrimidin-4-yl, 5-chloro-2-trifluoromethylpyrimidin-4-yl, 6-trifluoromethylpyridin-3-yl, 2-trifluoromethylpyridin-3-yl, 4-trifluoromethylpyridin-3-yl, 4-chloro-6-trifluoromethylpyridin-3-yl, 2-chloro-6-trifluoromethylpyridin-3-yl, 2-chloro-5-trifluoromethylpyridin-3-yl, 4-fluoro-6-trifluoromethylpyridin-3-yl, 4,6-bis(trifluoromethyl)pyridin-3-yl, 4,6-dichloropyridin-3-yl, 4-methyl-6-chloropyridin-3-yl, 5-cyanopyridin-3-yl, 5-fluoro-6-cyanopyridin-3-yl, 4-fluoro-6-cyanopyridin-3-yl, 6-methylsulfonylpyridin-3-yl, 5-chloro-6-methylsulfonylpyridin-3-yl, 5-methyl-6-methylsulfonylpyridin-3-yl, 2-thiazolyl, 5-trifluoromethylthiazol-2-yl, 4-trifluoromethylthiazol-2-yl, 6-trifluoromethylpyrazin-2-yl, 5-trifluoromethylpyrazin-2-yl, 3-trifluoromethylpyrazin-2-yl, 3-chloro-5-trifluoromethylpyrazin-2-yl, 3-fluoro-5-trifluoromethylpyrazin-2-yl, 5-chloro-6-trifluoromethylpyrazin-2-yl, 6-trifluoromethylpyridazin-3-yl, 5-trifluoromethylpyridazin-3-yl, 4-trifluoromethylpyridazin-3-yl, 4-methyl-6-trifluoromethylpyridazin-3-yl, 4-chloro-6-difluoromethoxypyridazin-3-yl, 4-fluoro-6-difluoromethoxypyridazin-3-yl, 4-methyl-6-difluoromethoxypyridazin-3-yl, 1,2,4-triazin-3-yl, 6-trifluoromethyl-1,2,4-triazin-3-yl, 5-trifluoromethyl-1,2,4-triazin-3-yl, 4,6-bis(trifluoromethyl)-1,3,5-triazin-2-yl, 4,6-bis(difluoromethoxy)-1,3,5-triazin-2-yl and 4,6-bis(methoxy)-1,3,5-triazin-2-yl.

Particularly preferred embodiments of the invention relate to compounds (I), wherein the group Het is one of the following radicals H-1 to H-9:

| No. | Het |
|---|---|
| H-1 | 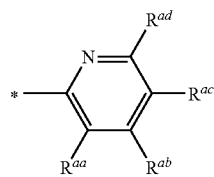 |
| H-2 | 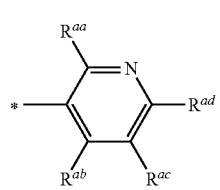 |
| H-3 | 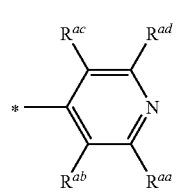 |
| H-4 | 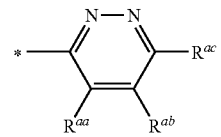 |
| H-5 | 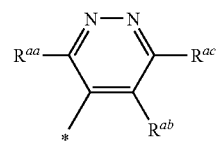 |
| H-6 | 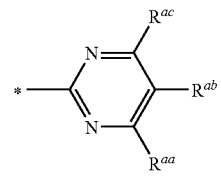 |
| H-7 | 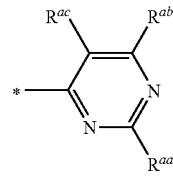 |
| H-8 | 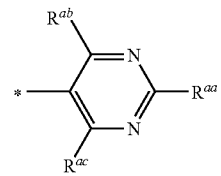 |
| H-9 | 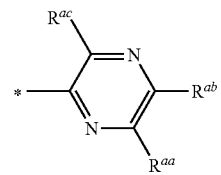 | wherein

*indicates the bond to Y; and $R^{aa}$, $R^{ab}$, $R^{ac}$ and $R^{ad}$ are each independently hydrogen or have one of the definitions specified for $R^a$, especially those being preferred.

Preference is also given to compounds (I), wherein n is 1 or 2.

Preference is also given to compounds (I), wherein $R^1$ is selected from F, Cl, Br, OH, SH, CN, $C_1$-$C_2$-alkyl, cyclopropyl, CH=CH$_2$, C≡CH, $C_1$-$C_2$-alkoxy, methylthio, methylamino, dimethylamino, $CF_3$, $CHF_2$, $OCF_3$ and $OCHF_2$.

More preference is given to compounds (I), wherein $R^1$ is selected from F, Cl, Br, CN, $C_1$-$C_2$-alkyl, $C_1$-$C_2$-alkoxy, $CF_3$, $CHF_2$, $OCF_3$ and $OCHF_2$.

Particular preference is given to compounds (I), wherein $R^1$ is selected from Cl, $CH_3$, and $OCH_3$.

Particular preference is given to compounds (I), wherein the moiety

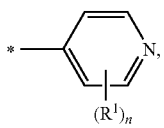

wherein * indicates the bond to the methylene bridge bound to the nitrogen atom of the sulfonamide group, is selected from pyridin-4-yl, 2-methylpyridin-4-yl, 3-methylpryridin-4-yl, 2-ethylpyridin-4-yl, 3-ethylpryridin-4-yl, 2,3-dimethylpyridin-4-yl, 2,3-diethylpyridin-4-yl, 2-methoxypyridin-4-yl, 3-methoxypryridin-4-yl, 2-difluoromethoxypyridin-4-yl, 2-cyanopyridin-4-yl, 2-chloropyridin-4-yl, 2-bromopyridin-4-yl, 2-chloro-3-methylpyridin-4-yl, 3-chloro-2-methylpyridin-4-yl, 2-chloro-3-ethylpyridin-4-yl, 3-chloro-2-ethylpyridin-4-yl, 2-methoxy-3-methylpyridin-4-yl and 3-methoxy-2-methylpyridin-4-yl.

One embodiment relates to compounds (I), wherein n is 2 and $R^1$ is in position 2 and 3 of the pyridine ring.

Another embodiment relates to compounds (I), wherein n is 2 and $R^1$ is in position 2 and 3 of the pyridine ring and is selected from halogen, $C_1$-$C_2$-alkyl, $C_1$-$C_2$-alkoxy, $C_1$-$C_2$-haloalkyl or $C_1$-$C_2$-haloalkoxy.

A further embodiment relates to compounds (I), wherein n is 2 and $R^1$ is in position 2 and 3 of the pyridine ring, wherein $R^1$ in position 2 is different from $R^1$ in position 3.

A further embodiment relates to compounds (I), wherein n is 2 and $R^1$ is in position 2 and 3 of the pyridine ring, wherein $R^1$ in position 2 is different from $R^1$ in position 3 and if one of both $R^1$ is $CH_3$, the other $R^1$ is not $OCH_3$.

A further embodiment relates to compounds (I), wherein n is 2 and $R^1$ is in position 2 and 3 of the pyridine ring, wherein $R^1$ in position 2 is different from $R^1$ in position 3 and is selected from halogen, $C_1$-$C_2$-alkyl, $C_1$-$C_2$-alkoxy, $C_1$-$C_2$-haloalkyl or $C_1$-$C_2$-haloalkoxy.

A further embodiment relates to compounds (I), wherein n is 2 and $R^1$ is in position 2 and 3 of the pyridine ring and is selected from Cl, F, $CH_3$, $OCH_3$ or $C_2H_5$.

A further embodiment relates to compounds (I), wherein n is 2, $R^1$ is in position 2 and 3 of the pyridine ring and $R^1$ is selected from Cl, F, $CH_3$, $OCH_3$ or $C_2H_5$, $R^1$ being different in position 2 from $R^1$ in position 3 and if one of both $R^1$ is $CH_3$, the other $R^1$ is not $OCH_3$.

A further embodiment relates to compounds (I), wherein n is 2 and $R^1$ is F in position 3 of the pyridine ring and $R^1$ is $OCH_3$, $CH_3$ or $C_2H_5$ in position 2.

A further embodiment relates to compounds (I), wherein n is 2 and $R^1$ is $C_2H_5$ in position 2 of the pyridine ring and $R^1$ is Cl, F, $CH_3$, $OCH_3$ or $C_2H_5$ in position 3.

A further embodiment relates to compounds (I), wherein n is 2 and $R^1$ is $CH_3$ in position 2 of the pyridine ring and $R^1$ is Cl, F, $CH_3$ or $C_2H_5$ in position 3.

A further embodiment relates to compounds (I), wherein n is 2 and $R^1$ is Cl in position 2 of the pyridine ring and $R^1$ is $CH_3$ or $C_2H_5$ in position 3.

A further embodiment relates to compounds (I) wherein n is 2 and $R^1$ is Cl in position 2 of the pyridine ring and $R^1$ is $CH_3$ or $C_2H_5$ in position 3.

A further embodiment relates to compounds (I) wherein n is 2 and $R^1$ is $OCH_3$ in position 2 of the pyridine ring and $R^1$ is Cl or F in position 3.

Preference is likewise given to compounds (I), wherein two radicals $R^1$ that are bound to adjacent carbon atoms of the pyridine ring may form together with said carbon atoms a fused benzene ring, a fused saturated or partially unsaturated 5-, 6-, or 7-membered carbocycle or a fused 5-, 6-, or 7-membered heterocycle selected from benzene, pyridine, pyrimidine, furane, thiazole and isoxazole, it being possible for the fused ring to carry 1 or 2 radicals selected from the group consisting of halogen, $C_1$-$C_4$-alkyl, halomethyl, $C_1$-$C_4$-alkoxy or halomethoxy.

More preference is given to compounds (I), wherein the moiety

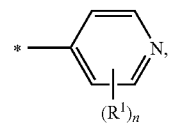

wherein * indicates the bond to the methylene bridge bound to the nitrogen atom of the sulfonamide group, is selected from quinolin-4-yl, 1,8-naphthyridin-4-yl, 1,7-naphthyridin-4-yl, 1,6-naphthyridin-4-yl, 1,5-naphthyridin-4-yl, pyrido-[2,3-d]pyrimidin-5-yl and pyrido[3,2-d]pyrimidin-8-yl, it being possible for the pyridin-4-yl ring to carry 1 or 2 further radicals $R^1$ and it being possible for the fused-on ring to carry 1 or 2 radicals selected from the group consisting of halogen, $C_1$-$C_4$-alkyl, halomethyl, $C_1$-$C_4$-alkoxy or halomethoxy. Particular preference is given to compounds (I), wherein the pyridin-4-yl moiety shown above is quinolin-4-yl. One embodiment relates to compounds (I), wherein the pyridin-4-yl moiety shown above is 5,6,7,8-tetrahydroquinolin-4-yl. Another embodiment relates to compounds (I), wherein the pyridin-4-yl moiety shown above is 2,3-dihydrofuro[2,3-b]pyridin-4-yl. A further embodiment relates to compounds (I), wherein the pyridin-4-yl moiety shown above is 2,3-dihydrofuro[3,2-b]pyridin-4-yl.

Preference is also given to compounds (I), wherein the moiety

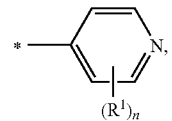

wherein * indicates the bond to the methylene bridge bound to the nitrogen atom of the sulfonamide group, is selected from pyrido[2,3-d]pyrimidin-5-yl, pyrido[2,3-b]pyrazin-8-yl, 3,4-dihydro-2H-pyrano[3,2-b]pyridin-8-yl, 3,4-dihydro-2H-pyrano[2,3-b]pyridin-5-yl, 3,4-dihydro-2H-pyrano[2,3-b]pyridin-5-yl, 1-methyl-1H-pyrrolo[2,3-b]pyridin-4-yl, 1-methyl-1H-pyrrolo[3,2-b]pyridin-7-yl, thieno[2,3-b]pyridin-4-yl, thieno[3,2-b]pyridin-7-yl, thiazolo[4,5-b]pyridin-7-yl, 2-methyl-thiazolo[4,5-b]pyridin-7-yl, thiazolo[5,4-b]pyridin-7-yl, 2-methyl-thiazolo[5,4-b]pyridin-7-yl, 1-ethyl-1H-imidazo[4,5-b]pyridin-7-yl, 1,2-dimethyl-1H-imidazo[4,5-b]pyridin-7-yl, 3-methyl-3H-imidazo[4,5-b]pyridin-7-yl, oxazolo[4,5-b]pyridin-7-yl, oxazolo[5,4-b]pyridin-7-yl, 2,3-dimethyl-3H-imidazo[4,5-b]-pyridin-7-yl, 2-methyl-oxazolo[4,5-b]pyridin-7-yl, 2-methyl-oxazolo[5,4-b]pyridin-7-yl, 2,3-dihydro-furo[2,3-b]pyridin-4-yl, 2,3-dihydro-furo[2,3-b]pyridin-4-yl, 2,3-dihydro-furo[3,2-b]pyridin-7-yl, 2,3-dihydro-furo[3,2-b]pyridin-7-yl, 2,3-dihydro-[1,4]dioxino[2,3-b]-pyridin-8-yl, 2,2-dimethyl-[1,3]dioxolo[4,5-b]pyridin-7-yl, 2-methyl-[1,3]dioxolo[4,5-b]pyridin-7-yl, [1,3]dioxolo[4,5-b]pyridin-7-yl, 2,2-dimethoxy-[1,3]dioxolo[4,5-b]pyridin-7-yl, it being possible for the pyridin-4-yl ring to carry 1 or 2 further radicals $R^1$ and it being possible for the fused-on ring to carry 1 or 2 radicals selected from the group consisting of halogen, $C_1$-$C_4$-alkyl, halomethyl, $C_1$-$C_4$-alkoxy or halomethoxy.

One embodiment of the invention relates to compounds (I), wherein the group Y-Het is bound to the phenylene moiety in the para-position with respect to the sulfonyl group, $R^2$ is hydrogen and $R^{1a}$, $R^{1b}$, $R^{1c}$ and $R^{1d}$ are each independently hydrogen or have one of the definitions specified for $R^1$, and $R^{3a}$, $R^{3b}$, $R^{3c}$ and $R^{3d}$ are each independently hydrogen or have one of the definitions specified for $R^3$, which compounds are of formula (I.1):

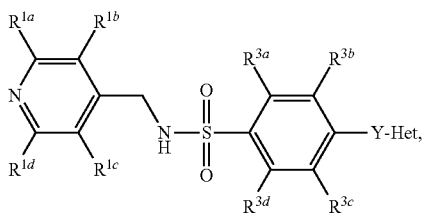

(I.1)

Particularly preferred embodiments of the invention relate to compounds (I.1), wherein the pyridin-4-yl group carries one of the following combinations of the radicals $R^{1a}$, $R^{1b}$, $R^{1c}$ and $R^{1d}$ as defined in Table P below.

TABLE P

| line | $R^{1a}$ | $R^{1b}$ | $R^{1c}$ | $R^{1d}$ |
|---|---|---|---|---|
| P-1 | H | H | H | H |
| P-2 | F | H | H | H |
| P-3 | Cl | H | H | H |
| P-4 | Br | H | H | H |
| P-5 | $CH_3$ | H | H | H |
| P-6 | $C_2H_5$ | H | H | H |
| P-7 | $C_3H_5$ | H | H | H |
| P-8 | $CF_3$ | H | H | H |
| P-9 | CN | H | H | H |
| P-10 | $OCH_3$ | H | H | H |
| P-11 | $OC_2H_5$ | H | H | H |
| P-12 | $OCF_3$ | H | H | H |
| P-13 | $OCHF_2$ | H | H | H |
| P-14 | C≡$CCH_3$ | H | H | H |
| P-15 | H | F | H | H |
| P-16 | H | Cl | H | H |
| P-17 | H | Br | H | H |
| P-18 | H | $CH_3$ | H | H |
| P-19 | H | $C_2H_5$ | H | H |
| P-20 | H | $C_3H_5$ | H | H |
| P-21 | H | $CF_3$ | H | H |
| P-22 | H | CN | H | H |
| P-23 | H | $OCH_3$ | H | H |
| P-24 | H | $OC_2H_5$ | H | H |
| P-25 | H | $OCF_3$ | H | H |
| P-26 | H | $OCHF_2$ | H | H |
| P-27 | H | C≡$CH_3$ | H | H |
| P-28 | $CH_3$ | $CH_3$ | H | H |
| P-29 | $C_2H_5$ | $CH_3$ | H | H |
| P-30 | $OCH_3$ | $CH_3$ | H | H |
| P-31 | $CH_3$ | $C_2H_5$ | H | H |
| P-32 | $C_2H_5$ | $C_2H_5$ | H | H |
| P-33 | $OCH_3$ | $C_2H_5$ | H | H |
| P-34 | $CH_3$ | $OCH_3$ | H | H |
| P-35 | $C_2H_5$ | $OCH_3$ | H | H |
| P-36 | $OCH_3$ | $OCH_3$ | H | H |
| P-37 | %—$(CH)_4$—# | | H | H | wherein
% indicates the point of attachment to the pyridine ring at the position of the $R^{1a}$ substituent; and
# indicates the point of attachment to the pyridine ring at the position of the $R^{1b}$ substituent.

Particularly preferred embodiments of the invention relate to compounds (I.1), wherein the 1,4-phenylene group carries one of the following combinations of the radicals $R^{3a}$, $R^{3b}$, $R^{3c}$ and $R^{3d}$ as defined in Table Q below.

TABLE Q

| line | $R^{3a}$ | $R^{3b}$ | $R^{3c}$ | $R^{3d}$ |
|---|---|---|---|---|
| Q-1 | H | H | H | H |
| Q-2 | $CH_3$ | H | H | H |
| Q-3 | H | $CH_3$ | H | H |
| Q-4 | $CH_3$ | $CH_3$ | H | H |
| Q-5 | $CH_3$ | H | H | $CH_3$ |
| Q-6 | H | $CH_3$ | $CH_3$ | H |
| Q-7 | $CH_3$ | H | $CH_3$ | H |

Preference is also given to compounds (I), wherein $R^2$ is hydrogen, $C_1$-$C_2$-alkyl, —CH=$CH_2$ or —$CH_2$—C≡CH.

Particular preference is given to compounds (I), wherein $R^2$ is hydrogen.

One embodiment relates to compounds (I), wherein $R^3$ is halogen, CN, $C_1$-$C_4$-alkyl, $C_1$-$C_4$-haloalkyl or $C_1$-$C_4$-alkoxy.

Another embodiment relates to compounds (I), wherein $R^3$ is halogen, CN, $C_1$-$C_2$-alkyl, $C_1$-$C_2$-haloalkyl or $C_1$-$C_2$-alkoxy.

A further embodiment relates to compounds (I), wherein $R^3$ is F, Cl, CN, $C_1$-$C_2$-alkyl, $C_1$-$C_2$-haloalkyl or $C_1$-$C_2$-alkoxy.

A further embodiment relates to compounds (I), wherein $R^3$ is F, Cl, CN, $CH_3$, $OCH_3$, $CF_3$ or $OCHF_2$.

A further embodiment relates to compounds (I), wherein $R^3$ is F or $CH_3$.

Preference is also given to compounds (I), wherein $R^3$ is hydrogen.

Preference is also given to compounds (I), wherein Y is a divalent group selected from —O—, —O—$CH_2$—, —$CH_2$—O—, —S—, —S(=O)—, —S(=O)$_2$— and —N($R''$)—, wherein $R''$ is hydrogen or $C_1$-$C_4$-alkyl.

Preference is also given to compounds (I), wherein Y is C-alkanediyl, wherein Y is unsubstituted or carries 1 or 2 substituents selected from oxo or $C_1$-$C_4$-alkyl, more preferably Y is —$CH_2$— or —C=O—.

Preference is also given to compounds (I), wherein Y is —O—, —S— or —NH—.

Particular preference is given to compounds (I), wherein Y is —O—.

A more specific embodiment relates to compounds (I), wherein the group Y-Het is bound to the phenylene moiety in the para-position with respect to the sulfonyl group, $R^2$ is hydrogen, Y is —O— and $R^{1a}$, $R^{1b}$, $R^{1c}$ and $R^{1d}$ are each independently hydrogen or have one of the definitions specified for $R^1$, and $R^{3a}$, $R^{3b}$, $R^{3c}$ and $R^{3d}$ are each independently hydrogen or have one of the definitions specified for $R^3$, which compounds are of formula (I.1A):

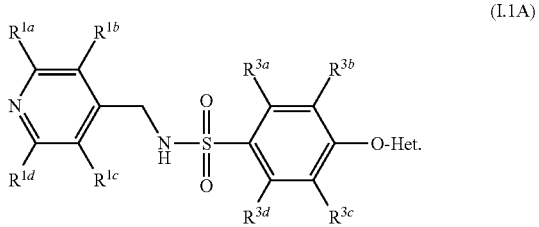

(I.1A)

A further embodiment relates to compounds (I), wherein Y is —N(R″)—, wherein R″ is hydrogen or $C_1$-$C_4$-alkyl. In one embodiment, R″ is $C_1$-$C_4$-alkyl, and preferably selected from methyl, ethyl, n-propyl and i-propyl, and in particular, R″ is methyl. In another embodiment, R″ is hydrogen.

A more preferred embodiment relates to compounds (I), wherein the group Y-Het is bound to the phenylene moiety in the para-position with respect to the sulfonyl group, $R^2$ is hydrogen, Y is —N(CH$_3$)— and $R^{1a}$, $R^{1b}$, $R^{1c}$ and $R^{1d}$ are each independently hydrogen or have one of the definitions specified for $R^1$, and $R^{3a}$, $R^{3b}$, $R^{3c}$ and $R^{3d}$ are each independently hydrogen or have one of the definitions specified for $R^3$, which compounds are of formula (I.1B):

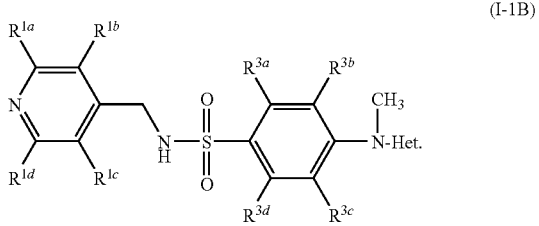

(I-1B)

A further embodiment relates to compounds (I), wherein Y is —CH$_2$—. A more preferred embodiment relates to compounds (I), wherein the group Y-Het is bound to the phenylene moiety in the para-position with respect to the sulfonyl group, $R^2$ is hydrogen, Y is —CH$_2$— and $R^{1a}$, $R^{1b}$, $R^{1c}$ and $R^{1d}$ are each independently hydrogen or have one of the definitions specified for $R^1$, and $R^{3a}$, $R^{3b}$, $R^{3c}$ and $R^{3d}$ are each independently hydrogen or have one of the definitions specified for $R^3$, which compounds are of formula (I.1G):

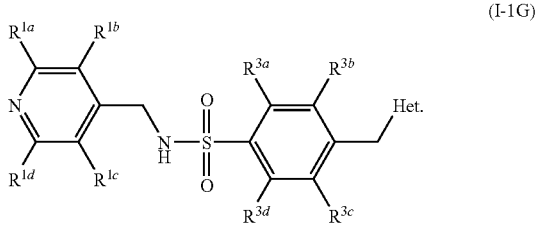

(I-1G)

One embodiment relates to compounds (I), wherein m is 0, 1, 2 or 3.

Another embodiment relates to compounds (I), wherein m is 1, 2, 3 or 4.

A further embodiment relates to compounds (I), wherein m is 1 or 2.

A further embodiment relates to compounds (I), wherein m is 0.

The preferences given in connection with compounds (I) also apply for compounds (I.1) and (I.1A), (I.1B) and (I.1G) as defined above as well as where applicable for intermediates such as compounds (II), (IV) and (V).

With respect to their use, particular preference is given to the compounds (I) compiled in the Tables 1 to 777 below, wherein the group Y-Het is bound to the phenylene moiety in the para-position with respect to the sulfonyl group, $R^2$ is hydrogen, and wherein the definitions for the substituents $R^1$ of the pyridine group are selected from P-1 to P-37 in Table P and the definitions for the substituents $R^3$ of the phenylene group are selected from Q-1 to Q-7 in Table Q and the definitions for the group Het are selected from H-1 and H-3 as described above. Here, the groups mentioned in the Tables for a substituent are furthermore, independently of the combination wherein they are mentioned, a particularly preferred embodiment of the substituent in question.

Table 1: Compounds (I.1A), wherein $R^{1a}$, $R^{1b}$, $R^{1c}$ and $R^{1d}$ are defined as in line P-1 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 2: Compounds (I.1A), wherein $R^{1a}$, $R^{1b}$, $R^{1c}$ and $R^{1d}$ are defined as in line P-2 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 3: Compounds (I.1A), wherein $R^{1a}$, $R^{1b}$, $R^{1c}$ and $R^{1d}$ are defined as in line P-3 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 4: Compounds (I.1A), wherein $R^{1a}$, $R^{1b}$, $R^{1c}$ and $R^{1d}$ are defined as in line P-4 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 5: Compounds (I.1A), wherein $R^{1a}$, $R^{1b}$, $R^{1c}$ and $R^{1d}$ are defined as in line P-5 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 6: Compounds (I.1A), wherein $R^{1a}$, $R^{1b}$, $R^{1c}$ and $R^{1d}$ are defined as in line P-6 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 7: Compounds (I.1A), wherein $R^{1a}$, $R^{1b}$, $R^{1c}$ and $R^{1d}$ are defined as in line P-7 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 8: Compounds (I.1A), wherein $R^{1a}$, $R^{1b}$, $R^{1c}$ and $R^{1d}$ are defined as in line P-8 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 9: Compounds (I.1A), wherein $R^{1a}$, $R^{1b}$, $R^{1c}$ and $R^{1d}$ are defined as in line P-9 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 10: Compounds (I.1A), wherein $R^{1a}$, $R^{1b}$, $R^{1c}$ and $R^{1d}$ are defined as in line P-10 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 11: Compounds (I.1A), wherein $R^{1a}$, $R^{1b}$, $R^{1c}$ and $R^{1d}$ are defined as in line P-11 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 12: Compounds (I.1A), wherein $R^{1a}$, $R^{1b}$, $R^{1c}$ and $R^{1d}$ are defined as in line P-12 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 13: Compounds (I.1A), wherein $R^{1a}$, $R^{1b}$, $R^{1c}$ and $R^{1d}$ are defined as in line P-13 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 14: Compounds (I.1A), wherein $R^{1a}$, $R^{1b}$, $R^{1c}$ and $R^{1d}$ are defined as in line P-14 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 15: Compounds (I.1A), wherein $R^{1a}$, $R^{1b}$, $R^{1c}$ and $R^{1d}$ are defined as in line P-15 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 16: Compounds (I.1A), wherein $R^{1a}$, $R^{1b}$, $R^{1c}$ and $R^{1d}$ are defined as in line P-16 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 17: Compounds (I.1A), wherein $R^{1a}$, $R^{1b}$, $R^{1c}$ and $R^{1d}$ are defined as in line P-17 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 18: Compounds (I.1A), wherein $R^{1a}$, $R^{1b}$, $R^{1c}$ and $R^{1d}$ are defined as in line P-18 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 19: Compounds (I.1A), wherein $R^{1a}$, $R^{1b}$, $R^{1c}$ and $R^{1d}$ are defined as in line P-19 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 20: Compounds (I.1A), wherein $R^{1a}$, $R^{1b}$, $R^{1c}$ and $R^{1d}$ are defined as in line P-20 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 21: Compounds (I.1A), wherein $R^{1a}$, $R^{1b}$, $R^{1c}$ and $R^{1d}$ are defined as in line P-21 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 22: Compounds (I.1A), wherein $R^{1a}$, $R^{1b}$, $R^{1c}$ and $R^{1d}$ are defined as in line P-22 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 23: Compounds (I.1A), wherein $R^{1a}$, $R^{1b}$, $R^{1c}$ and $R^{1d}$ are defined as in line P-23 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 24: Compounds (I.1A), wherein $R^{1a}$, $R^{1b}$, $R^{1c}$ and $R^{1d}$ are defined as in line P-24 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 25: Compounds (I.1A), wherein $R^{1a}$, $R^{1b}$, $R^{1c}$ and $R^{1d}$ are defined as in line P-25 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 26: Compounds (I.1A), wherein $R^{1a}$, $R^{1b}$, $R^{1c}$ and $R^{1d}$ are defined as in line P-26 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 27: Compounds (I.1A), wherein $R^{1a}$, $R^{1b}$, $R^{1c}$ and $R^{1d}$ are defined as in line P-27 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 28: Compounds (I.1A), wherein $R^{1a}$, $R^{1b}$, $R^{1c}$ and $R^{1d}$ are defined as in line P-28 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 29: Compounds (I.1A), wherein $R^{1M}$, $R^{1b}$, $R^{1c}$ and $R^{1d}$ are defined as in line P-29 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 30: Compounds (I.1A), wherein $R^{1a}$, $R^{1b}$, $R^{1c}$ and $R^{1d}$ are defined as in line P-30 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 31: Compounds (I.1A), wherein $R^{1a}$, $R^{1b}$, $R^{1c}$ and $R^{1d}$ are defined as in line P-31 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 32: Compounds (I.1A), wherein $R^{1M}$, $R^{1b}$, $R^{1c}$ and $R^{1d}$ are defined as in line P-32 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 33: Compounds (I.1A), wherein $R^{1a}$, $R^{1b}$, $R^{1c}$ and $R^{1d}$ are defined as in line P-33 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 34: Compounds (I.1A), wherein $R^{1M}$, $R^{1b}$, $R^{1c}$ and $R^{1d}$ are defined as in line P-34 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 35: Compounds (I.1A), wherein $R^{1M}$, $R^{1b}$, $R^{1c}$ and $R^{1d}$ are defined as in line P-35 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 36: Compounds (I.1A), wherein $R^{1a}$, $R^{1b}$, $R^{1c}$ and $R^{1d}$ are defined as in line P-36 of table P, $R^{3a}$, $R^{3b}$, $R^{3c}$ and $R^{3d}$ are defined as in line Q-1 of Table Q and the meaning of Het for each individual compound corresponds in each case to one line of table A.

Table 37: Compounds (I.1A), wherein $R^{1a}$, $R^{1b}$, $R^{1c}$ and $R^{1d}$ are defined as in line P-37 of table P, $R^{3a}$, $R^{3b}$, $R^{3c}$ and $R^{3d}$ are defined as in line Q-1 of Table Q and the meaning of Het for each individual compound corresponds in each case to one line of table A.

Tables 38 to 74: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-2 instead of line Q-1 of Table Q and the meaning of Het for each individual compound corresponds in each case to one line of table A.

Tables 75 to 111: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-3 instead of line Q-1 of Table Q and the meaning of Het for each individual compound corresponds in each case to one line of table A.

Tables 112 to 148: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-4 instead of line Q-1 of Table Q and the meaning of Het for each individual compound corresponds in each case to one line of table A.

Tables 149 to 185: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-5 instead of line Q-1 of Table Q and the meaning of Het for each individual compound corresponds in each case to one line of table A.

Tables 186 to 222: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-6 instead of line Q-1 of Table Q and the meaning of Het for each individual compound corresponds in each case to one line of table A.

Tables 223 to 259: Compounds (I.1A), wherein $R^{1a}$, $R^{1b}$, $R^{1c}$ and $R^{1d}$ are defined as in Tables 1 to 926 and $R^{3a}$, $R^{3b}$, $R^{3c}$ and $R^{3d}$ are defined as in line Q-7 instead of line Q-1 of Table Q and the meaning of Het for each individual compound corresponds in each case to one line of table A.

Tables 260 to 518: Compounds (I.1B), wherein $R^{1a}$, $R^{1b}$, $R^{1c}$ and $R^{1d}$ and $R^{3a}$, $R^{3b}$, $R^{3c}$ and $R^{3d}$ are defined as in Tables 1 to 259 and the meaning of Het for each individual compound corresponds in each case to one line of table A.

Tables 519 to 777: Compounds (I.1G), wherein $R^{1a}$, $R^{1b}$, $R^{1c}$ and $R^{11d}$ and $R^{3a}$, $R^{3b}$, $R^{3c}$ and $R^{3d}$ are defined as in Tables 1 to 259 and the meaning of Het for each individual compound corresponds in each case to one line of table A.

TABLE A

| line | Het | $R^{aa}$ | $R^{ab}$ | $R^{ac}$ | $R^{ad}$ |
|---|---|---|---|---|---|
| 1 | H-1 | H | H | H | H |
| 2 | H-1 | F | H | H | H |
| 3 | H-1 | Cl | H | H | H |
| 4 | H-1 | Br | H | H | H |
| 5 | H-1 | $CH_3$ | H | H | H |
| 6 | H-1 | $CF_3$ | H | H | H |
| 7 | H-1 | $CHF_2$ | H | H | H |
| 8 | H-1 | $OCH_3$ | H | H | H |
| 9 | H-1 | $OCF_3$ | H | H | H |
| 10 | H-1 | $OCHF_2$ | H | H | H |
| 11 | H-1 | $SCH_3$ | H | H | H |
| 12 | H-1 | H | F | H | H |
| 13 | H-1 | H | Cl | H | H |
| 14 | H-1 | H | Br | H | H |
| 15 | H-1 | H | $CH_3$ | H | H |
| 16 | H-1 | H | $CF_3$ | H | H |
| 17 | H-1 | H | $CHF_2$ | H | H |
| 18 | H-1 | H | $OCH_3$ | H | H |
| 19 | H-1 | H | $OCF_3$ | H | H |
| 20 | H-1 | H | $OCHF_2$ | H | H |
| 21 | H-1 | H | $SCH_3$ | H | H |
| 22 | H-1 | H | H | F | H |
| 23 | H-1 | H | H | Cl | H |
| 24 | H-1 | H | H | Br | H |
| 25 | H-1 | H | H | $CH_3$ | H |

TABLE A-continued

| line | Het | $R^{aa}$ | $R^{ab}$ | $R^{ac}$ | $R^{ad}$ |
|---|---|---|---|---|---|
| 26 | H-1 | H | H | $CF_3$ | H |
| 27 | H-1 | H | H | $CHF_2$ | H |
| 28 | H-1 | H | H | $OCH_3$ | H |
| 29 | H-1 | H | H | $OCF_3$ | H |
| 30 | H-1 | H | H | $OCHF_2$ | H |
| 31 | H-1 | H | H | $SCH_3$ | H |
| 32 | H-1 | H | H | H | F |
| 33 | H-1 | H | H | H | Cl |
| 34 | H-1 | H | H | H | Br |
| 35 | H-1 | H | H | H | $CH_3$ |
| 36 | H-1 | H | H | H | $CF_3$ |
| 37 | H-1 | H | H | H | $CHF_2$ |
| 38 | H-1 | H | H | H | $OCH_3$ |
| 39 | H-1 | H | H | H | $OCF_3$ |
| 40 | H-1 | H | H | H | $OCHF_2$ |
| 41 | H-1 | H | H | H | $SCH_3$ |
| 42 | H-1 | F | F | H | H |
| 43 | H-1 | Cl | F | H | H |
| 44 | H-1 | Br | F | H | H |
| 45 | H-1 | $CH_3$ | F | H | H |
| 46 | H-1 | $CF_3$ | F | H | H |
| 47 | H-1 | $CHF_2$ | F | H | H |
| 48 | H-1 | $OCH_3$ | F | H | H |
| 49 | H-1 | $OCF_3$ | F | H | H |
| 50 | H-1 | $OCHF_2$ | F | H | H |
| 51 | H-1 | $SCH_3$ | F | H | H |
| 52 | H-1 | F | Cl | H | H |
| 53 | H-1 | Cl | Cl | H | H |
| 54 | H-1 | Br | Cl | H | H |
| 55 | H-1 | $CH_3$ | Cl | H | H |
| 56 | H-1 | $CF_3$ | Cl | H | H |
| 57 | H-1 | $CHF_2$ | Cl | H | H |
| 58 | H-1 | $OCH_3$ | Cl | H | H |
| 59 | H-1 | $OCF_3$ | Cl | H | H |
| 60 | H-1 | $OCHF_2$ | Cl | H | H |
| 61 | H-1 | $SCH_3$ | Cl | H | H |
| 62 | H-1 | F | Br | H | H |
| 63 | H-1 | Cl | Br | H | H |
| 64 | H-1 | Br | Br | H | H |
| 65 | H-1 | $CH_3$ | Br | H | H |
| 66 | H-1 | $CF_3$ | Br | H | H |
| 67 | H-1 | $CHF_2$ | Br | H | H |
| 68 | H-1 | $OCH_3$ | Br | H | H |
| 69 | H-1 | $OCF_3$ | Br | H | H |
| 70 | H-1 | $OCHF_2$ | Br | H | H |
| 71 | H-1 | $SCH_3$ | Br | H | H |
| 72 | H-1 | F | $CH_3$ | H | H |
| 73 | H-1 | Cl | $CH_3$ | H | H |
| 74 | H-1 | Br | $CH_3$ | H | H |
| 75 | H-1 | $CH_3$ | $CH_3$ | H | H |
| 76 | H-1 | $CF_3$ | $CH_3$ | H | H |
| 77 | H-1 | $CHF_2$ | $CH_3$ | H | H |
| 78 | H-1 | $OCH_3$ | $CH_3$ | H | H |
| 79 | H-1 | $OCF_3$ | $CH_3$ | H | H |
| 80 | H-1 | $OCHF_2$ | $CH_3$ | H | H |
| 81 | H-1 | $SCH_3$ | $CH_3$ | H | H |
| 82 | H-1 | F | $CF_3$ | H | H |
| 83 | H-1 | Cl | $CF_3$ | H | H |
| 84 | H-1 | Br | $CF_3$ | H | H |
| 85 | H-1 | $CH_3$ | $CF_3$ | H | H |
| 86 | H-1 | $CF_3$ | $CF_3$ | H | H |
| 87 | H-1 | $CHF_2$ | $CF_3$ | H | H |
| 88 | H-1 | $OCH_3$ | $CF_3$ | H | H |
| 89 | H-1 | $OCF_3$ | $CF_3$ | H | H |
| 90 | H-1 | $OCHF_2$ | $CF_3$ | H | H |
| 91 | H-1 | $SCH_3$ | $CF_3$ | H | H |
| 92 | H-1 | F | $CHF_2$ | H | H |
| 93 | H-1 | Cl | $CHF_2$ | H | H |
| 94 | H-1 | Br | $CHF_2$ | H | H |
| 95 | H-1 | $CH_3$ | $CHF_2$ | H | H |
| 96 | H-1 | $CF_3$ | $CHF_2$ | H | H |
| 97 | H-1 | $CHF_2$ | $CHF_2$ | H | H |
| 98 | H-1 | $OCH_3$ | $CHF_2$ | H | H |
| 99 | H-1 | $OCF_3$ | $CHF_2$ | H | H |
| 100 | H-1 | $OCHF_2$ | $CHF_2$ | H | H |
| 101 | H-1 | $SCH_3$ | $CHF_2$ | H | H |
| 102 | H-1 | F | $OCH_3$ | H | H |
| 103 | H-1 | Cl | $OCH_3$ | H | H |

TABLE A-continued

| line | Het | R$^{aa}$ | R$^{ab}$ | R$^{ac}$ | R$^{ad}$ |
|---|---|---|---|---|---|
| 104 | H-1 | Br | OCH$_3$ | H | H |
| 105 | H-1 | CH$_3$ | OCH$_3$ | H | H |
| 106 | H-1 | CF$_3$ | OCH$_3$ | H | H |
| 107 | H-1 | CHF$_2$ | OCH$_3$ | H | H |
| 108 | H-1 | OCH$_3$ | OCH$_3$ | H | H |
| 109 | H-1 | OCF$_3$ | OCH$_3$ | H | H |
| 110 | H-1 | OCHF$_2$ | OCH$_3$ | H | H |
| 111 | H-1 | SCH$_3$ | OCH$_3$ | H | H |
| 112 | H-1 | F | OCF$_3$ | H | H |
| 113 | H-1 | Cl | OCF$_3$ | H | H |
| 114 | H-1 | Br | OCF$_3$ | H | H |
| 115 | H-1 | CH$_3$ | OCF$_3$ | H | H |
| 116 | H-1 | CF$_3$ | OCF$_3$ | H | H |
| 117 | H-1 | CHF$_2$ | OCF$_3$ | H | H |
| 118 | H-1 | OCH$_3$ | OCF$_3$ | H | H |
| 119 | H-1 | OCF$_3$ | OCF$_3$ | H | H |
| 120 | H-1 | OCHF$_2$ | OCF$_3$ | H | H |
| 121 | H-1 | SCH$_3$ | OCF$_3$ | H | H |
| 122 | H-1 | F | OCHF$_2$ | H | H |
| 123 | H-1 | Cl | OCHF$_2$ | H | H |
| 124 | H-1 | Br | OCHF$_2$ | H | H |
| 125 | H-1 | CH$_3$ | OCHF$_2$ | H | H |
| 126 | H-1 | CF$_3$ | OCHF$_2$ | H | H |
| 127 | H-1 | CHF$_2$ | OCHF$_2$ | H | H |
| 128 | H-1 | OCH$_3$ | OCHF$_2$ | H | H |
| 129 | H-1 | OCF$_3$ | OCHF$_2$ | H | H |
| 130 | H-1 | OCHF$_2$ | OCHF$_2$ | H | H |
| 131 | H-1 | SCH$_3$ | OCHF$_2$ | H | H |
| 132 | H-1 | F | SCH$_3$ | H | H |
| 133 | H-1 | Cl | SCH$_3$ | H | H |
| 134 | H-1 | Br | SCH$_3$ | H | H |
| 135 | H-1 | CH$_3$ | SCH$_3$ | H | H |
| 136 | H-1 | CF$_3$ | SCH$_3$ | H | H |
| 137 | H-1 | CHF$_2$ | SCH$_3$ | H | H |
| 138 | H-1 | OCH$_3$ | SCH$_3$ | H | H |
| 139 | H-1 | OCHF$_2$ | SCH$_3$ | H | H |
| 140 | H-1 | OCF$_3$ | SCH$_3$ | H | H |
| 141 | H-1 | SCH$_3$ | SCH$_3$ | H | H |
| 142 | H-1 | F | H | F | H |
| 143 | H-1 | Cl | H | F | H |
| 144 | H-1 | Br | H | F | H |
| 145 | H-1 | CH$_3$ | H | F | H |
| 146 | H-1 | CF$_3$ | H | F | H |
| 147 | H-1 | CHF$_2$ | H | F | H |
| 148 | H-1 | OCH$_3$ | H | F | H |
| 149 | H-1 | OCF$_3$ | H | F | H |
| 150 | H-1 | OCHF$_2$ | H | F | H |
| 151 | H-1 | SCH$_3$ | H | F | H |
| 152 | H-1 | F | H | Cl | H |
| 153 | H-1 | Cl | H | Cl | H |
| 154 | H-1 | Br | H | Cl | H |
| 155 | H-1 | CH$_3$ | H | Cl | H |
| 156 | H-1 | CF$_3$ | H | Cl | H |
| 157 | H-1 | CHF$_2$ | H | Cl | H |
| 158 | H-1 | OCH$_3$ | H | Cl | H |
| 159 | H-1 | OCF$_3$ | H | Cl | H |
| 160 | H-1 | OCHF$_2$ | H | Cl | H |
| 161 | H-1 | SCH$_3$ | H | Cl | H |
| 162 | H-1 | F | H | Br | H |
| 163 | H-1 | Cl | H | Br | H |
| 164 | H-1 | Br | H | Br | H |
| 165 | H-1 | CH$_3$ | H | Br | H |
| 166 | H-1 | CF$_3$ | H | Br | H |
| 167 | H-1 | CHF$_2$ | H | Br | H |
| 168 | H-1 | OCH$_3$ | H | Br | H |
| 169 | H-1 | OCF$_3$ | H | Br | H |
| 170 | H-1 | OCHF$_2$ | H | Br | H |
| 171 | H-1 | SCH$_3$ | H | Br | H |
| 172 | H-1 | F | H | CH$_3$ | H |
| 173 | H-1 | Cl | H | CH$_3$ | H |
| 174 | H-1 | Br | H | CH$_3$ | H |
| 175 | H-1 | CH$_3$ | H | CH$_3$ | H |
| 176 | H-1 | CF$_3$ | H | CH$_3$ | H |
| 177 | H-1 | CHF$_2$ | H | CH$_3$ | H |
| 178 | H-1 | OCH$_3$ | H | CH$_3$ | H |
| 179 | H-1 | OCF$_3$ | H | CH$_3$ | H |
| 180 | H-1 | OCHF$_2$ | H | CH$_3$ | H |
| 181 | H-1 | SCH$_3$ | H | CH$_3$ | H |
| 182 | H-1 | F | H | CF$_3$ | H |
| 183 | H-1 | Cl | H | CF$_3$ | H |
| 184 | H-1 | Br | H | CF$_3$ | H |
| 185 | H-1 | CH$_3$ | H | CF$_3$ | H |
| 186 | H-1 | CF$_3$ | H | CF$_3$ | H |
| 187 | H-1 | CHF$_2$ | H | CF$_3$ | H |
| 188 | H-1 | OCH$_3$ | H | CF$_3$ | H |
| 189 | H-1 | OCF$_3$ | H | CF$_3$ | H |
| 190 | H-1 | OCHF$_2$ | H | CF$_3$ | H |
| 191 | H-1 | SCH$_3$ | H | CF$_3$ | H |
| 192 | H-1 | F | H | CHF$_2$ | H |
| 193 | H-1 | Cl | H | CHF$_2$ | H |
| 194 | H-1 | Br | H | CHF$_2$ | H |
| 195 | H-1 | CH$_3$ | H | CHF$_2$ | H |
| 196 | H-1 | CF$_3$ | H | CHF$_2$ | H |
| 197 | H-1 | CHF$_2$ | H | CHF$_2$ | H |
| 198 | H-1 | OCH$_3$ | H | CHF$_2$ | H |
| 199 | H-1 | OCF$_3$ | H | CHF$_2$ | H |
| 200 | H-1 | OCHF$_2$ | H | CHF$_2$ | H |
| 201 | H-1 | SCH$_3$ | H | CHF$_2$ | H |
| 202 | H-1 | F | H | OCH$_3$ | H |
| 203 | H-1 | Cl | H | OCH$_3$ | H |
| 204 | H-1 | Br | H | OCH$_3$ | H |
| 205 | H-1 | CH$_3$ | H | OCH$_3$ | H |
| 206 | H-1 | CF$_3$ | H | OCH$_3$ | H |
| 207 | H-1 | CHF$_2$ | H | OCH$_3$ | H |
| 208 | H-1 | OCH$_3$ | H | OCH$_3$ | H |
| 209 | H-1 | OCF$_3$ | H | OCH$_3$ | H |
| 210 | H-1 | OCHF$_2$ | H | OCH$_3$ | H |
| 211 | H-1 | SCH$_3$ | H | OCH$_3$ | H |
| 212 | H-1 | F | H | OCF$_3$ | H |
| 213 | H-1 | Cl | H | OCF$_3$ | H |
| 214 | H-1 | Br | H | OCF$_3$ | H |
| 215 | H-1 | CH$_3$ | H | OCF$_3$ | H |
| 216 | H-1 | CF$_3$ | H | OCF$_3$ | H |
| 217 | H-1 | CHF$_2$ | H | OCF$_3$ | H |
| 218 | H-1 | OCH$_3$ | H | OCF$_3$ | H |
| 219 | H-1 | OCF$_3$ | H | OCF$_3$ | H |
| 220 | H-1 | OCHF$_2$ | H | OCF$_3$ | H |
| 221 | H-1 | SCH$_3$ | H | OCF$_3$ | H |
| 222 | H-1 | F | H | OCHF$_2$ | H |
| 223 | H-1 | Cl | H | OCHF$_2$ | H |
| 224 | H-1 | Br | H | OCHF$_2$ | H |
| 225 | H-1 | CH$_3$ | H | OCHF$_2$ | H |
| 226 | H-1 | CF$_3$ | H | OCHF$_2$ | H |
| 227 | H-1 | CHF$_2$ | H | OCHF$_2$ | H |
| 228 | H-1 | OCH$_3$ | H | OCHF$_2$ | H |
| 229 | H-1 | OCF$_3$ | H | OCHF$_2$ | H |
| 230 | H-1 | OCHF$_2$ | H | OCHF$_2$ | H |
| 231 | H-1 | SCH$_3$ | H | OCHF$_2$ | H |
| 232 | H-1 | F | H | SCH$_3$ | H |
| 233 | H-1 | Cl | H | SCH$_3$ | H |
| 234 | H-1 | Br | H | SCH$_3$ | H |
| 235 | H-1 | CH$_3$ | H | SCH$_3$ | H |
| 236 | H-1 | CF$_3$ | H | SCH$_3$ | H |
| 237 | H-1 | CHF$_2$ | H | SCH$_3$ | H |
| 238 | H-1 | OCH$_3$ | H | SCH$_3$ | H |
| 239 | H-1 | OCF$_3$ | H | SCH$_3$ | H |
| 240 | H-1 | OCHF$_2$ | H | SCH$_3$ | H |
| 241 | H-1 | SCH$_3$ | H | SCH$_3$ | H |
| 242 | H-1 | F | H | H | F |
| 243 | H-1 | Cl | H | H | F |
| 244 | H-1 | Br | H | H | F |
| 245 | H-1 | CH$_3$ | H | H | F |
| 246 | H-1 | CF$_3$ | H | H | F |
| 247 | H-1 | CHF$_2$ | H | H | F |
| 248 | H-1 | OCH$_3$ | H | H | F |
| 249 | H-1 | OCF$_3$ | H | H | F |
| 250 | H-1 | OCHF$_2$ | H | H | F |
| 251 | H-1 | SCH$_3$ | H | H | F |
| 252 | H-1 | F | H | H | Cl |
| 253 | H-1 | Cl | H | H | Cl |
| 254 | H-1 | Br | H | H | Cl |
| 255 | H-1 | CH$_3$ | H | H | Cl |
| 256 | H-1 | CF$_3$ | H | H | Cl |
| 257 | H-1 | CHF$_2$ | H | H | Cl |
| 258 | H-1 | OCH$_3$ | H | H | Cl |
| 259 | H-1 | OCF$_3$ | H | H | Cl |

TABLE A-continued

| line | Het | $R^{aa}$ | $R^{ab}$ | $R^{ac}$ | $R^{ad}$ |
|---|---|---|---|---|---|
| 260 | H-1 | OCHF$_2$ | H | H | Cl |
| 261 | H-1 | SCH$_3$ | H | H | Cl |
| 262 | H-1 | F | H | H | Br |
| 263 | H-1 | Cl | H | H | Br |
| 264 | H-1 | Br | H | H | Br |
| 265 | H-1 | CH$_3$ | H | H | Br |
| 266 | H-1 | CF$_3$ | H | H | Br |
| 267 | H-1 | CHF$_2$ | H | H | Br |
| 268 | H-1 | OCH$_3$ | H | H | Br |
| 269 | H-1 | OCF$_3$ | H | H | Br |
| 270 | H-1 | OCHF$_2$ | H | H | Br |
| 271 | H-1 | SCH$_3$ | H | H | Br |
| 272 | H-1 | F | H | H | CH$_3$ |
| 273 | H-1 | Cl | H | H | CH$_3$ |
| 274 | H-1 | Br | H | H | CH$_3$ |
| 275 | H-1 | CH$_3$ | H | H | CH$_3$ |
| 276 | H-1 | CF$_3$ | H | H | CH$_3$ |
| 277 | H-1 | CHF$_2$ | H | H | CH$_3$ |
| 278 | H-1 | OCH$_3$ | H | H | CH$_3$ |
| 279 | H-1 | OCF$_3$ | H | H | CH$_3$ |
| 280 | H-1 | OCHF$_2$ | H | H | CH$_3$ |
| 281 | H-1 | SCH$_3$ | H | H | CH$_3$ |
| 282 | H-1 | F | H | H | CF$_3$ |
| 283 | H-1 | Cl | H | H | CF$_3$ |
| 284 | H-1 | Br | H | H | CF$_3$ |
| 285 | H-1 | CH$_3$ | H | H | CF$_3$ |
| 286 | H-1 | CF$_3$ | H | H | CF$_3$ |
| 287 | H-1 | CHF$_2$ | H | H | CF$_3$ |
| 288 | H-1 | OCH$_3$ | H | H | CF$_3$ |
| 289 | H-1 | OCF$_3$ | H | H | CF$_3$ |
| 290 | H-1 | OCHF$_2$ | H | H | CF$_3$ |
| 291 | H-1 | SCH$_3$ | H | H | CF$_3$ |
| 292 | H-1 | F | H | H | CHF$_2$ |
| 293 | H-1 | Cl | H | H | CHF$_2$ |
| 294 | H-1 | Br | H | H | CHF$_2$ |
| 295 | H-1 | CH$_3$ | H | H | CHF$_2$ |
| 296 | H-1 | CF$_3$ | H | H | CHF$_2$ |
| 297 | H-1 | CHF$_2$ | H | H | CHF$_2$ |
| 298 | H-1 | OCH$_3$ | H | H | CHF$_2$ |
| 299 | H-1 | OCF$_3$ | H | H | CHF$_2$ |
| 300 | H-1 | OCHF$_2$ | H | H | CHF$_2$ |
| 301 | H-1 | SCH$_3$ | H | H | CHF$_2$ |
| 302 | H-1 | F | H | H | OCH$_3$ |
| 303 | H-1 | Cl | H | H | OCH$_3$ |
| 304 | H-1 | Br | H | H | OCH$_3$ |
| 305 | H-1 | CH$_3$ | H | H | OCH$_3$ |
| 306 | H-1 | CF$_3$ | H | H | OCH$_3$ |
| 307 | H-1 | CHF$_2$ | H | H | OCH$_3$ |
| 308 | H-1 | OCH$_3$ | H | H | OCH$_3$ |
| 309 | H-1 | OCF$_3$ | H | H | OCH$_3$ |
| 310 | H-1 | OCHF$_2$ | H | H. | OCH$_3$ |
| 311 | H-1 | SCH$_3$ | H | H | OCH$_3$ |
| 312 | H-1 | F | H | H | OCF$_3$ |
| 313 | H-1 | Cl | H | H | OCF$_3$ |
| 314 | H-1 | Br | H | H | OCF$_3$ |
| 315 | H-1 | CH$_3$ | H | H | OCF$_3$ |
| 316 | H-1 | CF$_3$ | H | H | OCF$_3$ |
| 317 | H-1 | CHF$_2$ | H | H | OCF$_3$ |
| 318 | H-1 | OCH$_3$ | H | H | OCF$_3$ |
| 319 | H-1 | OCF$_3$ | H | H | OCF$_3$ |
| 320 | H-1 | OCHF$_2$ | H | H | OCF$_3$ |
| 321 | H-1 | SCH$_3$ | H | H | OCF$_3$ |
| 322 | H-1 | F | H | H | OCHF$_2$ |
| 323 | H-1 | Cl | H | H | OCHF$_2$ |
| 324 | H-1 | Br | H | H | OCHF$_2$ |
| 325 | H-1 | CH$_3$ | H | H | OCHF$_2$ |
| 326 | H-1 | CF$_3$ | H | H | OCHF$_2$ |
| 327 | H-1 | CHF$_2$ | H | H | OCHF$_2$ |
| 328 | H-1 | OCH$_3$ | H | H | OCHF$_2$ |
| 329 | H-1 | OCF$_3$ | H | H | OCHF$_2$ |
| 330 | H-1 | OCHF$_2$ | H | H | OCHF$_2$ |
| 331 | H-1 | SCH$_3$ | H | H | OCHF$_2$ |
| 332 | H-1 | F | H | H | SCH$_3$ |
| 333 | H-1 | Cl | H | H | SCH$_3$ |
| 334 | H-1 | Br | H | H | SCH$_3$ |
| 335 | H-1 | CH$_3$ | H | H | SCH$_3$ |
| 336 | H-1 | CF$_3$ | H | H | SCH$_3$ |
| 337 | H-1 | CHF$_2$ | H | H | SCH$_3$ |
| 338 | H-1 | OCH$_3$ | H | H | SCH$_3$ |
| 339 | H-1 | OCF$_3$ | H | H | SCH$_3$ |
| 340 | H-1 | OCHF$_2$ | H | H | SCH$_3$ |
| 341 | H-1 | SCH$_3$ | H | H | SCH$_3$ |
| 342 | H-1 | H | F | F | H |
| 343 | H-1 | H | Cl | F | H |
| 344 | H-1 | H | Br | F | H |
| 345 | H-1 | H | CH$_3$ | F | H |
| 346 | H-1 | H | CF$_3$ | F | H |
| 347 | H-1 | H | CHF$_2$ | F | H |
| 348 | H-1 | H | OCH$_3$ | F | H |
| 349 | H-1 | H | OCF$_3$ | F | H |
| 350 | H-1 | H | OCHF$_2$ | F | H |
| 351 | H-1 | H | SCH$_3$ | F | H |
| 352 | H-1 | H | F | Cl | H |
| 353 | H-1 | H | Cl | Cl | H |
| 354 | H-1 | H | Br | Cl | H |
| 355 | H-1 | H | CH$_3$ | Cl | H |
| 356 | H-1 | H | CF$_3$ | Cl | H |
| 357 | H-1 | H | CHF$_2$ | Cl | H |
| 358 | H-1 | H | OCH$_3$ | Cl | H |
| 359 | H-1 | H | OCF$_3$ | Cl | H |
| 360 | H-1 | H | OCHF$_2$ | Cl | H |
| 361 | H-1 | H | SCH$_3$ | Cl | H |
| 362 | H-1 | H | F | Br | H |
| 363 | H-1 | H | Cl | Br | H |
| 364 | H-1 | H | Br | Br | H |
| 365 | H-1 | H | CH$_3$ | Br | H |
| 366 | H-1 | H | CF$_3$ | Br | H |
| 367 | H-1 | H | CHF$_2$ | Br | H |
| 368 | H-1 | H | OCH$_3$ | Br | H |
| 369 | H-1 | H | OCF$_3$ | Br | H |
| 370 | H-1 | H | OCHF$_2$ | Br | H |
| 371 | H-1 | H | SCH$_3$ | Br | H |
| 372 | H-1 | H | F | CH$_3$ | H |
| 373 | H-1 | H | Cl | CH$_3$ | H |
| 374 | H-1 | H | Br | CH$_3$ | H |
| 375 | H-1 | H | CH$_3$ | CH$_3$ | H |
| 376 | H-1 | H | CF$_3$ | CH$_3$ | H |
| 377 | H-1 | H | CHF$_2$ | CH$_3$ | H |
| 378 | H-1 | H | OCH$_3$ | CH$_3$ | H |
| 379 | H-1 | H | OCF$_3$ | CH$_3$ | H |
| 380 | H-1 | H | OCHF$_2$ | CH$_3$ | H |
| 381 | H-1 | H | SCH$_3$ | CH$_3$ | H |
| 382 | H-1 | H | F | CF$_3$ | H |
| 383 | H-1 | H | Cl | CF$_3$ | H |
| 384 | H-1 | H | Br | CF$_3$ | H |
| 385 | H-1 | H | CH$_3$ | CF$_3$ | H |
| 386 | H-1 | H | CF$_3$ | CF$_3$ | H |
| 387 | H-1 | H | CHF$_2$ | CF$_3$ | H |
| 388 | H-1 | H | OCH$_3$ | CF$_3$ | H |
| 389 | H-1 | H | OCF$_3$ | CF$_3$ | H |
| 390 | H-1 | H | OCHF$_2$ | CF$_3$ | H |
| 391 | H-1 | H | SCH$_3$ | CF$_3$ | H |
| 392 | H-1 | H | F | CHF$_2$ | H |
| 393 | H-1 | H | Cl | CHF$_2$ | H |
| 394 | H-1 | H | Br | CHF$_2$ | H |
| 395 | H-1 | H | CH$_3$ | CHF$_2$ | H |
| 396 | H-1 | H | CF$_3$ | CHF$_2$ | H |
| 397 | H-1 | H | CHF$_2$ | CHF$_2$ | H |
| 398 | H-1 | H | OCH$_3$ | CHF$_2$ | H |
| 399 | H-1 | H | OCF$_3$ | CHF$_2$ | H |
| 400 | H-1 | H | OCHF$_2$ | CHF$_2$ | H |
| 401 | H-1 | H | SCH$_3$ | CHF$_2$ | H |
| 402 | H-1 | H | F | OCH$_3$ | H |
| 403 | H-1 | H | Cl | OCH$_3$ | H |
| 404 | H-1 | H | Br | OCH$_3$ | H |
| 405 | H-1 | H | CH$_3$ | OCH$_3$ | H |
| 406 | H-1 | H | CF$_3$ | OCH$_3$ | H |
| 407 | H-1 | H | CHF$_2$ | OCH$_3$ | H |
| 408 | H-1 | H | OCH$_3$ | OCH$_3$ | H |
| 409 | H-1 | H | OCF$_3$ | OCH$_3$ | H |
| 410 | H-1 | H | OCHF$_2$ | OCH$_3$ | H |
| 411 | H-1 | H | SCH$_3$ | OCH$_3$ | H |
| 412 | H-1 | H | F | OCF$_3$ | H |
| 413 | H-1 | H | Cl | OCF$_3$ | H |
| 414 | H-1 | H | Br | OCF$_3$ | H |
| 415 | H-1 | H | CH$_3$ | OCF$_3$ | H |

TABLE A-continued

| line | Het | $R^{aa}$ | $R^{ab}$ | $R^{ac}$ | $R^{ad}$ |
|---|---|---|---|---|---|
| 416 | H-1 | H | CF$_3$ | OCF$_3$ | H |
| 417 | H-1 | H | CHF$_2$ | OCF$_3$ | H |
| 418 | H-1 | H | OCH$_3$ | OCF$_3$ | H |
| 419 | H-1 | H | OCF$_3$ | OCF$_3$ | H |
| 420 | H-1 | H | OCHF$_2$ | OCF$_3$ | H |
| 421 | H-1 | H | SCH$_3$ | OCF$_3$ | H |
| 422 | H-1 | H | F | OCHF$_2$ | H |
| 423 | H-1 | H | Cl | OCHF$_2$ | H |
| 424 | H-1 | H | Br | OCHF$_2$ | H |
| 425 | H-1 | H | CH$_3$ | OCHF$_2$ | H |
| 426 | H-1 | H | CF$_3$ | OCHF$_2$ | H |
| 427 | H-1 | H | CHF$_2$ | OCHF$_2$ | H |
| 428 | H-1 | H | OCH$_3$ | OCHF$_2$ | H |
| 429 | H-1 | H | OCF$_3$ | OCHF$_2$ | H |
| 430 | H-1 | H | OCHF$_2$ | OCHF$_2$ | H |
| 431 | H-1 | H | SCH$_3$ | OCHF$_2$ | H |
| 432 | H-1 | H | F | SCH$_3$ | H |
| 433 | H-1 | H | Cl | SCH$_3$ | H |
| 434 | H-1 | H | Br | SCH$_3$ | H |
| 435 | H-1 | H | CH$_3$ | SCH$_3$ | H |
| 436 | H-1 | H | CF$_3$ | SCH$_3$ | H |
| 437 | H-1 | H | CHF$_2$ | SCH$_3$ | H |
| 438 | H-1 | H | OCH$_3$ | SCH$_3$ | H |
| 439 | H-1 | H | OCF$_3$ | SCH$_3$ | H |
| 440 | H-1 | H | OCHF$_2$ | SCH$_3$ | H |
| 441 | H-1 | H | SCH$_3$ | SCH$_3$ | H |
| 442 | H-1 | H | F | H | F |
| 443 | H-1 | H | Cl | H | F |
| 444 | H-1 | H | Br | H | F |
| 445 | H-1 | H | CH$_3$ | H | F |
| 446 | H-1 | H | CF$_3$ | H | F |
| 447 | H-1 | H | CHF$_2$ | H | F |
| 448 | H-1 | H | OCH$_3$ | H | F |
| 449 | H-1 | H | OCF$_3$ | H | F |
| 450 | H-1 | H | OCHF$_2$ | H | F |
| 451 | H-1 | H | SCH$_3$ | H | F |
| 452 | H-1 | H | F | H | Cl |
| 453 | H-1 | H | Cl | H | Cl |
| 454 | H-1 | H | Br | H | Cl |
| 455 | H-1 | H | CH$_3$ | H | Cl |
| 456 | H-1 | H | CF$_3$ | H | Cl |
| 457 | H-1 | H | CHF$_2$ | H | Cl |
| 458 | H-1 | H | OCH$_3$ | H | Cl |
| 459 | H-1 | H | OCF$_3$ | H | Cl |
| 460 | H-1 | H | OCHF$_2$ | H | Cl |
| 461 | H-1 | H | SCH$_3$ | H | Cl |
| 462 | H-1 | H | F | H | Br |
| 463 | H-1 | H | Cl | H | Br |
| 464 | H-1 | H | Br | H | Br |
| 465 | H-1 | H | CH$_3$ | H | Br |
| 466 | H-1 | H | CF$_3$ | H | Br |
| 467 | H-1 | H | CHF$_2$ | H | Br |
| 468 | H-1 | H | OCH$_3$ | H | Br |
| 469 | H-1 | H | OCF$_3$ | H | Br |
| 470 | H-1 | H | OCHF$_2$ | H | Br |
| 471 | H-1 | H | SCH$_3$ | H | Br |
| 472 | H-1 | H | F | H | CH$_3$ |
| 473 | H-1 | H | Cl | H | CH$_3$ |
| 474 | H-1 | H | Br | H | CH$_3$ |
| 475 | H-1 | H | CH$_3$ | H | CH$_3$ |
| 476 | H-1 | H | CF$_3$ | H | CH$_3$ |
| 477 | H-1 | H | CHF$_2$ | H | CH$_3$ |
| 478 | H-1 | H | OCH$_3$ | H | CH$_3$ |
| 479 | H-1 | H | OC$_2$H$_5$ | H | CH$_3$ |
| 480 | H-1 | H | OCF$_3$ | H | CH$_3$ |
| 481 | H-1 | H | SCH$_3$ | H | CH$_3$ |
| 482 | H-1 | H | F | H | CF$_3$ |
| 483 | H-1 | H | Cl | H | CF$_3$ |
| 484 | H-1 | H | Br | H | CF$_3$ |
| 485 | H-1 | H | CH$_3$ | H | CF$_3$ |
| 486 | H-1 | H | CF$_3$ | H | CF$_3$ |
| 487 | H-1 | H | CHF$_2$ | H | CF$_3$ |
| 488 | H-1 | H | OCH$_3$ | H | CF$_3$ |
| 489 | H-1 | H | OC$_2$H$_5$ | H | CF$_3$ |
| 490 | H-1 | H | OCF$_3$ | H | CF$_3$ |
| 491 | H-1 | H | SCH$_3$ | H | CF$_3$ |
| 492 | H-1 | H | F | H | CHF$_2$ |
| 493 | H-1 | H | Cl | H | CHF$_2$ |
| 494 | H-1 | H | Br | H | CHF$_2$ |
| 495 | H-1 | H | CH$_3$ | H | CHF$_2$ |
| 496 | H-1 | H | CF$_3$ | H | CHF$_2$ |
| 497 | H-1 | H | CHF$_2$ | H | CHF$_2$ |
| 498 | H-1 | H | OCH$_3$ | H | CHF$_2$ |
| 499 | H-1 | H | OCHF$_2$ | H | CHF$_2$ |
| 500 | H-1 | H | OCF$_3$ | H | CHF$_2$ |
| 501 | H-1 | H | SCH$_3$ | H | CHF$_2$ |
| 502 | H-1 | H | F | H | OCH$_3$ |
| 503 | H-1 | H | Cl | H | OCH$_3$ |
| 504 | H-1 | H | Br | H | OCH$_3$ |
| 505 | H-1 | H | CH$_3$ | H | OCH$_3$ |
| 506 | H-1 | H | CF$_3$ | H | OCH$_3$ |
| 507 | H-1 | H | CHF$_2$ | H | OCH$_3$ |
| 508 | H-1 | H | OCH$_3$ | H | OCH$_3$ |
| 509 | H-1 | H | OCF$_3$ | H | OCH$_3$ |
| 510 | H-1 | H | OCHF$_2$ | H | OCH$_3$ |
| 511 | H-1 | H | SCH$_3$ | H | OCH$_3$ |
| 512 | H-1 | H | F | H | OCF$_3$ |
| 513 | H-1 | H | Cl | H | OCF$_3$ |
| 514 | H-1 | H | Br | H | OCF$_3$ |
| 515 | H-1 | H | CH$_3$ | H | OCF$_3$ |
| 516 | H-1 | H | CF$_3$ | H | OCF$_3$ |
| 517 | H-1 | H | CHF$_2$ | H | OCF$_3$ |
| 518 | H-1 | H | OCH$_3$ | H | OCF$_3$ |
| 519 | H-1 | H | OCF$_3$ | H | OCF$_3$ |
| 520 | H-1 | H | OCHF$_2$ | H | OCF$_3$ |
| 521 | H-1 | H | SCH$_3$ | H | OCF$_3$ |
| 522 | H-1 | H | F | H | OCHF$_2$ |
| 523 | H-1 | H | Cl | H | OCHF$_2$ |
| 524 | H-1 | H | Br | H | OCHF$_2$ |
| 525 | H-1 | H | CH$_3$ | H | OCHF$_2$ |
| 526 | H-1 | H | CF$_3$ | H | OCHF$_2$ |
| 527 | H-1 | H | CHF$_2$ | H | OCHF$_2$ |
| 528 | H-1 | H | OCH$_3$ | H | OCHF$_2$ |
| 529 | H-1 | H | OCF$_3$ | H | OCHF$_2$ |
| 530 | H-1 | H | OCHF$_2$ | H | OCHF$_2$ |
| 531 | H-1 | H | SCH$_3$ | H | OCHF$_2$ |
| 532 | H-1 | H | F | H | SCH$_3$ |
| 533 | H-1 | H | Cl | H | SCH$_3$ |
| 534 | H-1 | H | Br | H | SCH$_3$ |
| 535 | H-1 | H | CH$_3$ | H | SCH$_3$ |
| 536 | H-1 | H | CF$_3$ | H | SCH$_3$ |
| 537 | H-1 | H | CHF$_2$ | H | SCH$_3$ |
| 538 | H-1 | H | OCH$_3$ | H | SCH$_3$ |
| 539 | H-1 | H | OCF$_3$ | H | SCH$_3$ |
| 540 | H-1 | H | OCHF$_2$ | H | SCH$_3$ |
| 541 | H-1 | H | SCH$_3$ | H | SCH$_3$ |
| 542 | H-1 | H | H | F | F |
| 543 | H-1 | H | H | Cl | F |
| 544 | H-1 | H | H | Br | F |
| 545 | H-1 | H | H | CH$_3$ | F |
| 546 | H-1 | H | H | CF$_3$ | F |
| 547 | H-1 | H | H | CHF$_2$ | F |
| 548 | H-1 | H | H | OCH$_3$ | F |
| 549 | H-1 | H | H | OCF$_3$ | F |
| 550 | H-1 | H | H | OCHF$_2$ | F |
| 551 | H-1 | H | H | SCH$_3$ | F |
| 552 | H-1 | H | H | F | Cl |
| 553 | H-1 | H | H | Cl | Cl |
| 554 | H-1 | H | H | Br | Cl |
| 555 | H-1 | H | H | CH$_3$ | Cl |
| 556 | H-1 | H | H | CF$_3$ | Cl |
| 557 | H-1 | H | H | CHF$_2$ | Cl |
| 558 | H-1 | H | H | OCH$_3$ | Cl |
| 559 | H-1 | H | H | OCF$_3$ | Cl |
| 560 | H-1 | H | H | OCHF$_2$ | Cl |
| 561 | H-1 | H | H | SCH$_3$ | Cl |
| 562 | H-1 | H | H | F | Br |
| 563 | H-1 | H | H | Cl | Br |
| 564 | H-1 | H | H | Br | Br |
| 565 | H-1 | H | H | CH$_3$ | Br |
| 566 | H-1 | H | H | CF$_3$ | Br |
| 567 | H-1 | H | H | CHF$_2$ | Br |
| 568 | H-1 | H | H | OCH$_3$ | Br |
| 569 | H-1 | H | H | OCF$_3$ | Br |
| 570 | H-1 | H | H | OCHF$_2$ | Br |
| 571 | H-1 | H | H | SCH$_3$ | Br |

TABLE A-continued

| line | Het | $R^{aa}$ | $R^{ab}$ | $R^{ac}$ | $R^{ad}$ |
|---|---|---|---|---|---|
| 572 | H-1 | H | H | F | $CH_3$ |
| 573 | H-1 | H | H | Cl | $CH_3$ |
| 574 | H-1 | H | H | Br | $CH_3$ |
| 575 | H-1 | H | H | $CH_3$ | $CH_3$ |
| 576 | H-1 | H | H | $CF_3$ | $CH_3$ |
| 577 | H-1 | H | H | $CHF_2$ | $CH_3$ |
| 578 | H-1 | H | H | $OCH_3$ | $CH_3$ |
| 579 | H-1 | H | H | $OCF_3$ | $CH_3$ |
| 580 | H-1 | H | H | $OCHF_2$ | $CH_3$ |
| 581 | H-1 | H | H | $SCH_3$ | $CH_3$ |
| 582 | H-1 | H | H | F | $CF_3$ |
| 583 | H-1 | H | H | Cl | $CF_3$ |
| 584 | H-1 | H | H | Br | $CF_3$ |
| 585 | H-1 | H | H | $CH_3$ | $CF_3$ |
| 586 | H-1 | H | H | $CF_3$ | $CF_3$ |
| 587 | H-1 | H | H | $CHF_2$ | $CF_3$ |
| 588 | H-1 | H | H | $OCH_3$ | $CF_3$ |
| 589 | H-1 | H | H | $OCF_3$ | $CF_3$ |
| 590 | H-1 | H | H | $OCHF_2$ | $CF_3$ |
| 591 | H-1 | H | H | $SCH_3$ | $CF_3$ |
| 592 | H-1 | H | H | F | $CHF_2$ |
| 593 | H-1 | H | H | Cl | $CHF_2$ |
| 594 | H-1 | H | H | Br | $CHF_2$ |
| 595 | H-1 | H | H | $CH_3$ | $CHF_2$ |
| 596 | H-1 | H | H | $CF_3$ | $CHF_2$ |
| 597 | H-1 | H | H | $CHF_2$ | $CHF_2$ |
| 598 | H-1 | H | H | $OCH_3$ | $CHF_2$ |
| 599 | H-1 | H | H | $OCF_3$ | $CHF_2$ |
| 600 | H-1 | H | H | $OCHF_2$ | $CHF_2$ |
| 601 | H-1 | H | H | $SCH_3$ | $CHF_2$ |
| 602 | H-1 | H | H | F | $OCH_3$ |
| 603 | H-1 | H | H | Cl | $OCH_3$ |
| 604 | H-1 | H | H | Br | $OCH_3$ |
| 605 | H-1 | H | H | $CH_3$ | $OCH_3$ |
| 606 | H-1 | H | H | $CF_3$ | $OCH_3$ |
| 607 | H-1 | H | H | $CHF_2$ | $OCH_3$ |
| 608 | H-1 | H | H | $OCH_3$ | $OCH_3$ |
| 609 | H-1 | H | H | $OCF_3$ | $OCH_3$ |
| 610 | H-1 | H | H | $OCHF_2$ | $OCH_3$ |
| 611 | H-1 | H | H | $SCH_3$ | $OCH_3$ |
| 612 | H-1 | H | H | F | $OCF_3$ |
| 613 | H-1 | H | H | Cl | $OCF_3$ |
| 614 | H-1 | H | H | Br | $OCF_3$ |
| 615 | H-1 | H | H | $CH_3$ | $OCF_3$ |
| 616 | H-1 | H | H | $CF_3$ | $OCF_3$ |
| 617 | H-1 | H | H | $CHF_2$ | $OCF_3$ |
| 618 | H-1 | H | H | $OCH_3$ | $OCF_3$ |
| 619 | H-1 | H | H | $OCF_3$ | $OCF_3$ |
| 620 | H-1 | H | H | $OCHF_2$ | $OCF_3$ |
| 621 | H-1 | H | H | $SCH_3$ | $OCF_3$ |
| 622 | H-3 | H | H | H | H |
| 623 | H-3 | F | H | H | H |
| 624 | H-3 | Cl | H | H | H |
| 625 | H-3 | Br | H | H | H |
| 626 | H-3 | $CH_3$ | H | H | H |
| 627 | H-3 | $CF_3$ | H | H | H |
| 628 | H-3 | $CHF_2$ | H | H | H |
| 629 | H-3 | $OCH_3$ | H | H | H |
| 630 | H-3 | $OCF_3$ | H | H | H |
| 631 | H-3 | $OCHF_2$ | H | H | H |
| 632 | H-3 | $SCH_3$ | H | H | H |
| 633 | H-3 | H | F | H | H |
| 634 | H-3 | H | Cl | H | H |
| 635 | H-3 | H | Br | H | H |
| 636 | H-3 | H | $CH_3$ | H | H |
| 637 | H-3 | H | $CF_3$ | H | H |
| 638 | H-3 | H | $CHF_2$ | H | H |
| 639 | H-3 | H | $OCH_3$ | H | H |
| 640 | H-3 | H | $OCF_3$ | H | H |
| 641 | H-3 | H | $OCHF_2$ | H | H |
| 642 | H-3 | H | $SCH_3$ | H | H |
| 643 | H-3 | F | F | H | H |
| 644 | H-3 | Cl | F | H | H |
| 645 | H-3 | Br | F | H | H |
| 646 | H-3 | $CH_3$ | F | H | H |
| 647 | H-3 | $CF_3$ | F | H | H |
| 648 | H-3 | $CHF_2$ | F | H | H |
| 649 | H-3 | $OCH_3$ | F | H | H |
| 650 | H-3 | $OCF_3$ | F | H | H |
| 651 | H-3 | $OCHF_2$ | F | H | H |
| 652 | H-3 | $SCH_3$ | F | H | H |
| 653 | H-3 | F | Cl | H | H |
| 654 | H-3 | Cl | Cl | H | H |
| 655 | H-3 | Br | Cl | H | H |
| 656 | H-3 | $CH_3$ | Cl | H | H |
| 657 | H-3 | $CF_3$ | Cl | H | H |
| 658 | H-3 | $CHF_2$ | Cl | H | H |
| 659 | H-3 | $OCH_3$ | Cl | H | H |
| 660 | H-3 | $OCF_3$ | Cl | H | H |
| 661 | H-3 | $OCHF_2$ | Cl | H | H |
| 662 | H-3 | $SCH_3$ | Cl | H | H |
| 663 | H-3 | F | Br | H | H |
| 664 | H-3 | Cl | Br | H | H |
| 665 | H-3 | Br | Br | H | H |
| 666 | H-3 | $CH_3$ | Br | H | H |
| 667 | H-3 | $CF_3$ | Br | H | H |
| 668 | H-3 | $CHF_2$ | Br | H | H |
| 669 | H-3 | $OCH_3$ | Br | H | H |
| 670 | H-3 | $OCF_3$ | Br | H | H |
| 671 | H-3 | $OCHF_2$ | Br | H | H |
| 672 | H-3 | $SCH_3$ | Br | H | H |
| 673 | H-3 | F | $CH_3$ | H | H |
| 674 | H-3 | Cl | $CH_3$ | H | H |
| 675 | H-3 | Br | $CH_3$ | H | H |
| 676 | H-3 | $CH_3$ | $CH_3$ | H | H |
| 677 | H-3 | $CF_3$ | $CH_3$ | H | H |
| 678 | H-3 | $CHF_2$ | $CH_3$ | H | H |
| 679 | H-3 | $OCH_3$ | $CH_3$ | H | H |
| 680 | H-3 | $OCF_3$ | $CH_3$ | H | H |
| 681 | H-3 | $OCHF_2$ | $CH_3$ | H | H |
| 682 | H-3 | $SCH_3$ | $CH_3$ | H | H |
| 683 | H-3 | F | $CF_3$ | H | H |
| 684 | H-3 | Cl | $CF_3$ | H | H |
| 685 | H-3 | Br | $CF_3$ | H | H |
| 686 | H-3 | $CH_3$ | $CF_3$ | H | H |
| 687 | H-3 | $CF_3$ | $CF_3$ | H | H |
| 688 | H-3 | $CHF_2$ | $CF_3$ | H | H |
| 689 | H-3 | $OCH_3$ | $CF_3$ | H | H |
| 690 | H-3 | $OCF_3$ | $CF_3$ | H | H |
| 691 | H-3 | $OCHF_2$ | $CF_3$ | H | H |
| 692 | H-3 | $SCH_3$ | $CF_3$ | H | H |
| 693 | H-3 | F | $CHF_2$ | H | H |
| 694 | H-3 | Cl | $CHF_2$ | H | H |
| 695 | H-3 | Br | $CHF_2$ | H | H |
| 696 | H-3 | $CH_3$ | $CHF_2$ | H | H |
| 697 | H-3 | $CF_3$ | $CHF_2$ | H | H |
| 698 | H-3 | $CHF_2$ | $CHF_2$ | H | H |
| 699 | H-3 | $OCH_3$ | $CHF_2$ | H | H |
| 700 | H-3 | $OCF_3$ | $CHF_2$ | H | H |
| 701 | H-3 | $OCHF_2$ | $CHF_2$ | H | H |
| 702 | H-3 | $SCH_3$ | $CHF_2$ | H | H |
| 703 | H-3 | F | $OCH_3$ | H | H |
| 704 | H-3 | Cl | $OCH_3$ | H | H |
| 705 | H-3 | Br | $OCH_3$ | H | H |
| 706 | H-3 | $CH_3$ | $OCH_3$ | H | H |
| 707 | H-3 | $CF_3$ | $OCH_3$ | H | H |
| 708 | H-3 | $CHF_2$ | $OCH_3$ | H | H |
| 709 | H-3 | $OCH_3$ | $OCH_3$ | H | H |
| 710 | H-3 | $OCF_3$ | $OCH_3$ | H | H |
| 711 | H-3 | $OCHF_2$ | $OCH_3$ | H | H |
| 712 | H-3 | $SCH_3$ | $OCH_3$ | H | H |
| 713 | H-3 | F | $OCF_3$ | H | H |
| 714 | H-3 | Cl | $OCF_3$ | H | H |
| 715 | H-3 | Br | $OCF_3$ | H | H |
| 716 | H-3 | $CH_3$ | $OCF_3$ | H | H |
| 717 | H-3 | $CF_3$ | $OCF_3$ | H | H |
| 718 | H-3 | $CHF_2$ | $OCF_3$ | H | H |
| 719 | H-3 | $OCH_3$ | $OCF_3$ | H | H |
| 720 | H-3 | $OCF_3$ | $OCF_3$ | H | H |
| 721 | H-3 | $OCHF_2$ | $OCF_3$ | H | H |
| 722 | H-3 | $SCH_3$ | $OCF_3$ | H | H |
| 723 | H-3 | F | $OCHF_2$ | H | H |
| 724 | H-3 | Cl | $OCHF_2$ | H | H |
| 725 | H-3 | Br | $OCHF_2$ | H | H |
| 726 | H-3 | $CH_3$ | $OCHF_2$ | H | H |
| 727 | H-3 | $CF_3$ | $OCHF_2$ | H | H |

TABLE A-continued

| line | Het | $R^{aa}$ | $R^{ab}$ | $R^{ac}$ | $R^{ad}$ |
|---|---|---|---|---|---|
| 728 | H-3 | CHF$_2$ | OCHF$_2$ | H | H |
| 729 | H-3 | OCH$_3$ | OCHF$_2$ | H | H |
| 730 | H-3 | OCF$_3$ | OCHF$_2$ | H | H |
| 731 | H-3 | OCHF$_2$ | OCHF$_2$ | H | H |
| 732 | H-3 | SCH$_3$ | OCHF$_2$ | H | H |
| 733 | H-3 | F | SCH$_3$ | H | H |
| 734 | H-3 | Cl | SCH$_3$ | H | H |
| 735 | H-3 | Br | SCH$_3$ | H | H |
| 736 | H-3 | CH$_3$ | SCH$_3$ | H | H |
| 737 | H-3 | CF$_3$ | SCH$_3$ | H | H |
| 738 | H-3 | CHF$_2$ | SCH$_3$ | H | H |
| 739 | H-3 | OCH$_3$ | SCH$_3$ | H | H |
| 740 | H-3 | OCF$_3$ | SCH$_3$ | H | H |
| 741 | H-3 | OCHF$_2$ | SCH$_3$ | H | H |
| 742 | H-3 | SCH$_3$ | SCH$_3$ | H | H |
| 743 | H-3 | F | H | F | H |
| 744 | H-3 | Cl | H | F | H |
| 745 | H-3 | Br | H | F | H |
| 746 | H-3 | CH$_3$ | H | F | H |
| 747 | H-3 | CF$_3$ | H | F | H |
| 748 | H-3 | CHF$_2$ | H | F | H |
| 749 | H-3 | OCH$_3$ | H | F | H |
| 750 | H-3 | OCF$_3$ | H | F | H |
| 751 | H-3 | OCHF$_2$ | H | F | H |
| 752 | H-3 | SCH$_3$ | H | F | H |
| 753 | H-3 | F | H | Cl | H |
| 754 | H-3 | Cl | H | Cl | H |
| 755 | H-3 | Br | H | Cl | H |
| 756 | H-3 | CH$_3$ | H | Cl | H |
| 757 | H-3 | CF$_3$ | H | Cl | H |
| 758 | H-3 | CHF$_2$ | H | Cl | H |
| 759 | H-3 | OCH$_3$ | H | Cl | H |
| 760 | H-3 | OCF$_3$ | H | Cl | H |
| 761 | H-3 | OCHF$_2$ | H | Cl | H |
| 762 | H-3 | SCH$_3$ | H | Cl | H |
| 763 | H-3 | F | H | Br | H |
| 764 | H-3 | Cl | H | Br | H |
| 765 | H-3 | Br | H | Br | H |
| 766 | H-3 | CH$_3$ | H | Br | H |
| 767 | H-3 | CF$_3$ | H | Br | H |
| 768 | H-3 | CHF$_2$ | H | Br | H |
| 769 | H-3 | OCH$_3$ | H | Br | H |
| 770 | H-3 | OCF$_3$ | H | Br | H |
| 771 | H-3 | OCHF$_2$ | H | Br | H |
| 772 | H-3 | SCH$_3$ | H | Br | H |
| 773 | H-3 | F | H | CH$_3$ | H |
| 774 | H-3 | Cl | H | CH$_3$ | H |
| 775 | H-3 | Br | H | CH$_3$ | H |
| 776 | H-3 | CH$_3$ | H | CH$_3$ | H |
| 777 | H-3 | CF$_3$ | H | CH$_3$ | H |
| 778 | H-3 | CHF$_2$ | H | CH$_3$ | H |
| 779 | H-3 | OCH$_3$ | H | CH$_3$ | H |
| 780 | H-3 | OCF$_3$ | H | CH$_3$ | H |
| 781 | H-3 | OCHF$_2$ | H | CH$_3$ | H |
| 782 | H-3 | SCH$_3$ | H | CH$_3$ | H |
| 783 | H-3 | F | H | CF$_3$ | H |
| 784 | H-3 | Cl | H | CF$_3$ | H |
| 785 | H-3 | Br | H | CF$_3$ | H |
| 786 | H-3 | CH$_3$ | H | CF$_3$ | H |
| 787 | H-3 | CF$_3$ | H | CF$_3$ | H |
| 788 | H-3 | CHF$_2$ | H | CF$_3$ | H |
| 789 | H-3 | OCH$_3$ | H | CF$_3$ | H |
| 790 | H-3 | OCF$_3$ | H | CF$_3$ | H |
| 791 | H-3 | OCHF$_2$ | H | CF$_3$ | H |
| 792 | H-3 | SCH$_3$ | H | CF$_3$ | H |
| 793 | H-3 | F | H | CHF$_2$ | H |
| 794 | H-3 | Cl | H | CHF$_2$ | H |
| 795 | H-3 | Br | H | CHF$_2$ | H |
| 796 | H-3 | CH$_3$ | H | CHF$_2$ | H |
| 797 | H-3 | CF$_3$ | H | CHF$_2$ | H |
| 798 | H-3 | CHF$_2$ | H | CHF$_2$ | H |
| 799 | H-3 | OCH$_3$ | H | CHF$_2$ | H |
| 800 | H-3 | OCF$_3$ | H | CHF$_2$ | H |
| 801 | H-3 | OCHF$_2$ | H | CHF$_2$ | H |
| 802 | H-3 | SCH$_3$ | H | CHF$_2$ | H |
| 803 | H-3 | F | H | OCH$_3$ | H |
| 804 | H-3 | Cl | H | OCH$_3$ | H |
| 805 | H-3 | Br | H | OCH$_3$ | H |
| 806 | H-3 | CH$_3$ | H | OCH$_3$ | H |
| 807 | H-3 | CF$_3$ | H | OCH$_3$ | H |
| 808 | H-3 | CHF$_2$ | H | OCH$_3$ | H |
| 809 | H-3 | OCH$_3$ | H | OCH$_3$ | H |
| 810 | H-3 | OCF$_3$ | H | OCH$_3$ | H |
| 811 | H-3 | OCHF$_2$ | H | OCH$_3$ | H |
| 812 | H-3 | SCH$_3$ | H | OCH$_3$ | H |
| 813 | H-3 | F | H | OCF$_3$ | H |
| 814 | H-3 | Cl | H | OCF$_3$ | H |
| 815 | H-3 | Br | H | OCF$_3$ | H |
| 816 | H-3 | CH$_3$ | H | OCF$_3$ | H |
| 817 | H-3 | CF$_3$ | H | OCF$_3$ | H |
| 818 | H-3 | CHF$_2$ | H | OCF$_3$ | H |
| 819 | H-3 | OCH$_3$ | H | OCF$_3$ | H |
| 820 | H-3 | OCF$_3$ | H | OCF$_3$ | H |
| 821 | H-3 | OCHF$_2$ | H | OCF$_3$ | H |
| 822 | H-3 | SCH$_3$ | H | OCF$_3$ | H |
| 823 | H-3 | F | H | OCHF$_2$ | H |
| 824 | H-3 | Cl | H | OCHF$_2$ | H |
| 825 | H-3 | Br | H | OCHF$_2$ | H |
| 826 | H-3 | CH$_3$ | H | OCHF$_2$ | H |
| 827 | H-3 | CF$_3$ | H | OCHF$_2$ | H |
| 828 | H-3 | CHF$_2$ | H | OCHF$_2$ | H |
| 829 | H-3 | OCH$_3$ | H | OCHF$_2$ | H |
| 830 | H-3 | OCF$_3$ | H | OCHF$_2$ | H |
| 831 | H-3 | OCHF$_2$ | H | OCHF$_2$ | H |
| 832 | H-3 | SCH$_3$ | H | OCHF$_2$ | H |
| 833 | H-3 | F | H | SCH$_3$ | H |
| 834 | H-3 | Cl | H | SCH$_3$ | H |
| 835 | H-3 | Br | H | SCH$_3$ | H |
| 836 | H-3 | CH$_3$ | H | SCH$_3$ | H |
| 837 | H-3 | CF$_3$ | H | SCH$_3$ | H |
| 838 | H-3 | CHF$_2$ | H | SCH$_3$ | H |
| 839 | H-3 | OCH$_3$ | H | SCH$_3$ | H |
| 840 | H-3 | OCF$_3$ | H | SCH$_3$ | H |
| 841 | H-3 | OCHF$_2$ | H | SCH$_3$ | H |
| 842 | H-3 | SCH$_3$ | H | SCH$_3$ | H |
| 843 | H-3 | F | H | H | F |
| 844 | H-3 | Cl | H | H | F |
| 845 | H-3 | Br | H | H | F |
| 846 | H-3 | CH$_3$ | H | H | F |
| 847 | H-3 | CF$_3$ | H | H | F |
| 848 | H-3 | CHF$_2$ | H | H | F |
| 849 | H-3 | OCH$_3$ | H | H | F |
| 850 | H-3 | OCF$_3$ | H | H | F |
| 851 | H-3 | OCHF$_2$ | H | H | F |
| 852 | H-3 | SCH$_3$ | H | H | F |
| 853 | H-3 | Cl | H | H | Cl |
| 854 | H-3 | Br | H | H | Cl |
| 855 | H-3 | CH$_3$ | H | H | Cl |
| 856 | H-3 | CF$_3$ | H | H | Cl |
| 857 | H-3 | CHF$_2$ | H | H | Cl |
| 858 | H-3 | OCH$_3$ | H | H | Cl |
| 859 | H-3 | OCF$_3$ | H | H | Cl |
| 860 | H-3 | OCHF$_2$ | H | H | Cl |
| 861 | H-3 | SCH$_3$ | H | H | Cl |
| 862 | H-3 | Br | H | H | Br |
| 863 | H-3 | CH$_3$ | H | H | Br |
| 864 | H-3 | CF$_3$ | H | H | Br |
| 865 | H-3 | CHF$_2$ | H | H | Br |
| 866 | H-3 | OCH$_3$ | H | H | Br |
| 867 | H-3 | OCF$_3$ | H | H | Br |
| 868 | H-3 | OCHF$_2$ | H | H | Br |
| 869 | H-3 | SCH$_3$ | H | H | Br |
| 870 | H-3 | CH$_3$ | H | H | CH$_3$ |
| 871 | H-3 | CF$_3$ | H | H | CH$_3$ |
| 872 | H-3 | CHF$_2$ | H | H | CH$_3$ |
| 873 | H-3 | OCH$_3$ | H | H | CH$_3$ |
| 874 | H-3 | OCF$_3$ | H | H | CH$_3$ |
| 875 | H-3 | OCHF$_2$ | H | H | CH$_3$ |
| 876 | H-3 | SCH$_3$ | H | H | CH$_3$ |
| 877 | H-3 | CF$_3$ | H | H | CF$_3$ |
| 878 | H-3 | CHF$_2$ | H | H | CF$_3$ |
| 879 | H-3 | OCH$_3$ | H | H | CF$_3$ |
| 880 | H-3 | OCHF$_2$ | H | H | CF$_3$ |
| 881 | H-3 | SCH$_3$ | H | H | CF$_3$ |
| 882 | H-3 | CHF$_2$ | H | H | CHF$_2$ |
| 883 | H-3 | OCH$_3$ | H | H | CHF$_2$ |

TABLE A-continued

| line | Het | $R^{aa}$ | $R^{ab}$ | $R^{ac}$ | $R^{ad}$ |
|---|---|---|---|---|---|
| 884 | H-3 | $OCF_3$ | H | H | $CHF_2$ |
| 885 | H-3 | $OCHF_2$ | H | H | $CHF_2$ |
| 886 | H-3 | $SCH_3$ | H | H | $CHF_2$ |
| 887 | H-3 | $OCH_3$ | H | H | $OCH_3$ |
| 888 | H-3 | $OCF_3$ | H | H | $OCH_3$ |
| 889 | H-3 | $OCHF_2$ | H | H | $OCH_3$ |
| 890 | H-3 | $SCH_3$ | H | H | $OCH_3$ |
| 891 | H-3 | $OCF_3$ | H | H | $OCF_3$ |
| 892 | H-3 | $OCHF_2$ | H | H | $OCF_3$ |
| 893 | H-3 | $SCH_3$ | H | H | $OCF_3$ |
| 894 | H-3 | $OCHF_2$ | H | H | $OCHF_2$ |
| 895 | H-3 | $SCH_3$ | H | H | $OCHF_2$ |
| 896 | H-3 | $SCH_3$ | H | H | $SCH_3$ |
| 897 | H-3 | H | F | F | H |
| 898 | H-3 | H | Cl | F | H |
| 899 | H-3 | H | Br | F | H |
| 900 | H-3 | H | $CH_3$ | F | H |
| 901 | H-3 | H | $CF_3$ | F | H |
| 902 | H-3 | H | $CHF_2$ | F | H |
| 903 | H-3 | H | $OCH_3$ | F | H |
| 904 | H-3 | H | $OCF_3$ | F | H |
| 905 | H-3 | H | $OCHF_2$ | F | H |
| 906 | H-3 | H | $SCH_3$ | F | H |
| 907 | H-3 | H | Cl | Cl | H |
| 908 | H-3 | H | Br | Cl | H |
| 909 | H-3 | H | $CH_3$ | Cl | H |
| 910 | H-3 | H | $CF_3$ | Cl | H |
| 911 | H-3 | H | $CHF_2$ | Cl | H |
| 912 | H-3 | H | $OCH_3$ | Cl | H |
| 913 | H-3 | H | $OCF_3$ | Cl | H |
| 914 | H-3 | H | $OCHF_2$ | Cl | H |
| 915 | H-3 | H | $SCH_3$ | Cl | H |
| 916 | H-3 | H | Br | Br | H |
| 917 | H-3 | H | $CH_3$ | Br | H |
| 918 | H-3 | H | $CF_3$ | Br | H |
| 919 | H-3 | H | $CHF_2$ | Br | H |
| 920 | H-3 | H | $OCH_3$ | Br | H |
| 921 | H-3 | H | $OCF_3$ | Br | H |
| 922 | H-3 | H | $OCHF_2$ | Br | H |
| 923 | H-3 | H | $SCH_3$ | Br | H |
| 924 | H-3 | H | $CH_3$ | $CH_3$ | H |
| 925 | H-3 | H | $CF_3$ | $CH_3$ | H |
| 926 | H-3 | H | $CHF_2$ | $CH_3$ | H |
| 927 | H-3 | H | $OCH_3$ | $CH_3$ | H |
| 928 | H-3 | H | $OCF_3$ | $CH_3$ | H |
| 929 | H-3 | H | $OCHF_2$ | $CH_3$ | H |
| 930 | H-3 | H | $SCH_3$ | $CH_3$ | H |
| 931 | H-3 | H | $CF_3$ | $CF_3$ | H |
| 932 | H-3 | H | $CHF_2$ | $CF_3$ | H |
| 933 | H-3 | H | $OCH_3$ | $CF_3$ | H |
| 934 | H-3 | H | $OCF_3$ | $CF_3$ | H |
| 935 | H-3 | H | $OCHF_2$ | $CF_3$ | H |
| 936 | H-3 | H | $SCH_3$ | $CF_3$ | H |
| 937 | H-3 | H | $CHF_2$ | $CHF_2$ | H |
| 938 | H-3 | H | $OCH_3$ | $CHF_2$ | H |
| 939 | H-3 | H | $OCF_3$ | $CHF_2$ | H |
| 940 | H-3 | H | $OCHF_2$ | $CHF_2$ | H |
| 941 | H-3 | H | $SCH_3$ | $CHF_2$ | H |
| 942 | H-3 | H | $OCH_3$ | $OCH_3$ | H |
| 943 | H-3 | H | $OCF_3$ | $OCH_3$ | H |
| 944 | H-3 | H | $OCHF_2$ | $OCH_3$ | H |
| 945 | H-3 | H | $SCH_3$ | $OCH_3$ | H |
| 946 | H-3 | H | $OCF_3$ | $OCF_3$ | H |
| 947 | H-3 | H | $OCHF_2$ | $OCF_3$ | H |
| 948 | H-3 | H | $SCH_3$ | $OCF_3$ | H |
| 949 | H-3 | H | $OCHF_2$ | $OCHF_2$ | H |
| 950 | H-3 | H | $SCH_3$ | $OCHF_2$ | H |
| 951 | H-3 | H | $SCH_3$ | $SCH_3$ | H |

The compounds (I) can be prepared by various routes in analogy to prior art processes known per se for preparing sulfonamide compounds and, advantageously, by the synthesis shown in the following schemes and in the experimental part of this application.

Compounds (II), wherein n, $R^1$, and $R^2$ are as defined above, can be reacted with compounds (III), wherein m, $R^3$, Y and Het are as defined above, and L is a leaving group such as halogen, hydroxy, azido, optionally substituted heteroaryl, optionally substituted heteroaryloxy or optionally substituted phenoxy, preferably chloro, fluoro or optionally substituted heteroaryl such as optionally substituted pyrazol-1-yl, imidazol-1-yl, 1,2,3-triazol-1-yl and 1,2,4-triazol-1-yl, pentafluorphenoxy or hydroxybenzotriazoloxy, to obtain compounds (I) as shown below:

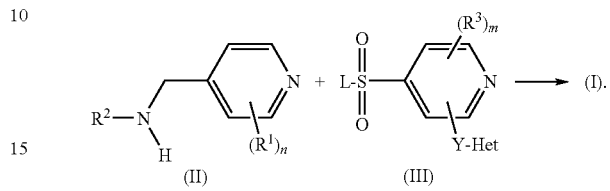

This reaction can be performed in accordance with standard methods of organic chemistry, see e.g. Lieb. Ann. Chem. P. 641, 1990, or WO 2005/033081 and is usually carried out in an inert organic solvent. Suitable solvents are aliphatic hydrocarbons, such as pentane, hexane, cyclohexane and petroleum ether, aromatic hydrocarbons, such as toluene, o-, m- and p-xylene, halogenated hydrocarbons, such as dichloromethane (DCM), chloroform and chlorobenzene, ethers, such as diethyl ether, diisopropyl ether, methyl tert.-butyl ether (MTBE), dioxane, anisole and tetrahydrofuran (THF), nitriles, such as acetonitrile and propionitrile, ketones, such as acetone, methyl ethyl ketone, diethyl ketone and tert.-butyl methyl ketone, and also dimethyl sulfoxide (DMSO), dimethylformamide (DMF) and dimethylacetamide, preferably THF, MTBE, dichloromethane, chloroform, acetonitrile, toluene or DMF. It is also possible to use mixtures of the solvents mentioned.

The reaction is usually carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, e.g. tertiary amines such as trimethylamine, triethylamine, diisopropylethylamine and N-methylpiperidine (NMP), pyridine, substituted pyridines, such as collidine, lutidine and 4-dimethylaminopyridine, and also bicyclic amines. Particular preference is given to triethylamine, pyridine, triethylamine and potassium carbonate. The bases are generally employed in catalytic amounts; however, they can also be used in equimolar amounts, in excess or, if appropriate, as solvent. The amount of base is typically 0.5 to 5 molar equivalents relative to 1 mole of compounds (II).

Generally, the reaction is carried out at temperatures of from −30 to 120° C., preferably from −10 to 100° C.

The starting materials, i.e. compounds (II) and compounds (III), are generally reacted with one another in equimolar amounts. In terms of yield it may be advantageous to employ an excess of compound (II) based on compound (III).

Accordingly a further aspect of the present invention relates to a process for preparing compounds (I) as defined before, which comprises reacting compounds (II), wherein n, $R^1$ and $R^2$ have one of the meanings given above, under basic conditions with compounds (III), wherein Y, Het, m and $R^3$ have one of the meanings given above and L is leaving group such as halogen, hydroxy, azido, optionally substituted heteroaryl, optionally substituted heteroaryloxy or optionally substituted phenoxy, preferably chloro, fluoro, optionally substituted heteroaryl such as optionally substituted pyrazol-1-yl, imidazol-1-yl, 1,2,3-triazol-1-yl and 1,2,4-triazol-1-yl, pentafluorphenoxy or hydroxybenzotriazoloxy.

Alternatively, compounds (IV), wherein L' is a leaving group such as methylsulfonyl, toluenesulfonyl or as defined for L in formula (III), preferably halogen, azido, methylsulfonyl or toluenesulfonyl, can be reacted with compounds (III.a) to obtain directly compounds (I) as shown below:

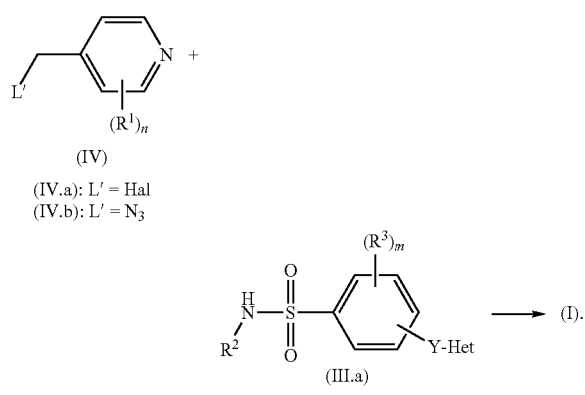

(IV)
(IV.a): L' = Hal
(IV.b): L' = $N_3$ (III.a)

→ (I).

This reaction can be conducted under similar conditions as described for reacting compounds (II) with compounds (III).

Some compounds (II) are known from the literature (e.g. from WO 06/097489, WO 02/066470, U.S. Pat. No. 4,482,437 or JP 04243867) or are commercially available or they can be prepared by appropriate methods known to those skilled in the art, e.g. by reduction of the corresponding oximes V.a, nitriles V.b, or amides V.c as described below:

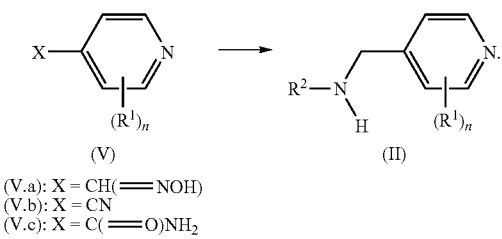

(V)
(V.a): X = CH(=NOH)
(V.b): X = CN
(V.c): X = C(=O)$NH_2$ (II)

Methods suitable for the reduction of oximes (V.a) to the corresponding amines (II) have been described in the literature e.g. in March J.: Reactions, mechanisms and structure, fourth edition, 1992, Wiley & Sons, New York, 1218-1219.

Methods suitable for the reduction of nitriles (V.b) to the corresponding amines (II) have been described in the literature, e.g. in March J.: Reactions, mechanisms and structure, fourth edition, 1992, Wiley & Sons, New York, 918-919.

Methods suitable for the reduction of amides (V.c) to the corresponding amines (II) have been described in the literature, e.g. in March J.: Reactions, mechanisms and structure, fourth edition, 1992, Wiley & Sons, New York, 1212-1213.

The oximes (V.a) can be prepared e.g. from either the respective aldehydes (compounds (V.d): X=CHO) or the methyl derivatives (compounds (V.e): X=$CH_3$), in analogy to Houben-Weyl, vol. 10/4, Thieme, Stuttgart, 1968; vol. 11/2, 1957; vol E5, 1985; J. Prakt. Chem./Chem. Ztg. 336(8), pp. 695-697, 1994; Tetrahedron Lett. 42(39), pp. 6815-6818, 2001; or Heterocycles, 29(9), pp. 1741-1760, 1989.

The nitriles (V.b) are either commercially available or can be prepared in analogy to methods described in Heterocycles, 41(4), 675 (1995), Chem. Pharm. Bull., 21, 1927 (1973) or J. Chem. Soc., 426 (1942), e.g. from the corresponding halides (compounds (V.f): X=halogen) by reaction with cyanides such as CuCN, NaCN or KCN. Halides (V.f) are commercially available or can be prepared according to standard methods.

The amides (V.c) can be prepared, e.g. from the corresponding carboxylic acid chlorides by reaction with ammonia.

The aldehydes (V.d) can be synthesized from the methyl derivatives (V.e) in analogy to J. Org. Chem. 51(4), pp. 536-537, 1986, or from halides (V.f): as shown in Eur. J. Org. Chem., 2003, (8), pp. 1576-1588; Tetrahedron Lett., 1999, 40 (19), pp. 3719-3722; Tetrahedron Lett., 1999, 55 (41), pp. 12149-12156.

A further method to obtain compounds (II), wherein $R^2$ is H, by reacting compounds (IV.a), wherein Hal is halogen, preferably chloro, with ammonia is shown below:

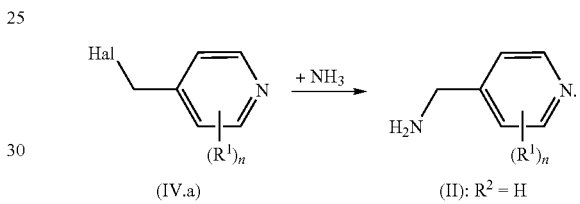

(IV.a)

(II): $R^2$ = H

Compounds (IV.a) are either commercially available or can be prepared in analogy to known procedures (cf. March, J. "Advanced Organic Chemistry: Reactions, Mechanisms, and Structure" (Wiley & Sons, New York, $3^{rd}$ edition, 1985, p. 1151)). In one alternative, this reaction can be carried out in aequeous ammonia.

In another alternative, this reaction can be carried out in condensed ammonia.

In a third alternative, the reaction can be carried out in an inert organic solvent using aequeous ammonia or by introduction of gaseous ammonia. Suitable solvents are alcohols such as methanol, ethanol, n-propanol, isopropanol, n-butanol and tert.-butanol; ethers such as diethyl ether, diisopropyl ether, MTBE, dioxane, anisole and THF; nitriles, such as acetonitrile and propionitrile; and also DMSO, DMF, dimethyl acetamide and NMP, preferably methanol, ethanol, isopropanol, dioxane, THF, acetonitrile, DMF, DMSO, NMP and mixtures thereof.

This reaction is usually carried out at temperatures of from −60 to 120° C., preferably from −10 to 50° C., in the presence of a base or with an excess of ammonia. Suitable bases are, in general, alkali metal and alkaline earth metal hydroxides such as lithium hydroxide, sodium hydroxide, potassium hydroxide and calcium hydroxide; alkali metal and alkaline earth metal oxides such as lithium oxide, sodium oxide, calcium oxide and magnesium oxide; alkali metal and alkaline earth metal hydrides such as lithium hydride, sodium hydride, potassium hydride and calcium hydride; alkali metal and alkaline earth metal carbonates such as lithium carbonate, potassium carbonate and calcium carbonate; and also alkali metal bicarbonates such as sodium bicarbonate; organic bases, e.g. tertiary amines such as trimethylamine, triethylamine, diisopropylethylamine and NMP; pyridine, substituted pyridines such as collidine, lutidine and 4-dimethylaminopyridine; and also bicyclic amines. The bases are generally employed in catalytic amounts; however, they can also be used in equimolar amounts, in excess or, if appropriate, as solvent. The amount of base is typically 0.5 to 5 molar equivalents, preferably 0.5 to 2 molar equivalents relative to 1 mole of compound (IV.a).

Generally, the starting materials are reacted with one another in equimolar amounts. In terms of yield it may be advantageous to employ an excess of ammonia, based on compound (IV.a).

A further method to obtain compounds (II) using protection groups is shown below. Compounds (IV.a) can be reacted with protected amines (VI), wherein Z is hydrogen or a protection group such as methylcarbamate, t-butylcarbamate or 2,2,2-trichlorethylcarbamate, to obtain after deprotection (cf. Greene T. W., Wits P. G. "Protective groups in organic synthesis", Wiley & Sons, New York, 1999, p. 494 et sqq.) the compounds (II), wherein $R^2$ is hydrogen.

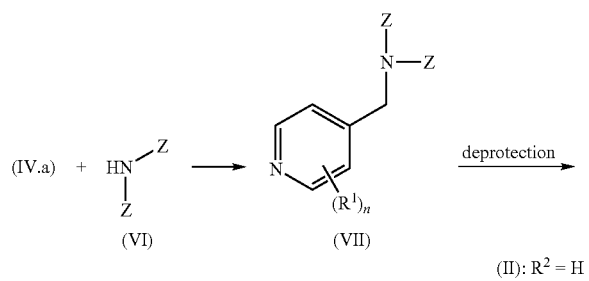

The first reaction introducing a protection group is generally carried out in an inert organic solvent. Suitable solvents, in general, are alcohols such as methanol, ethanol, n-propanol, isopropanol, n-butanol and tert.-butanol; ethers such as diethyl ether, diisopropyl ether, MTBE, dioxane, anisole and THF; nitriles, such as acetonitrile and propionitrile; ketones such as acetone, methylethyl-ketone, diethyl-ketone and tert.-butyl methyl ketone; and also DMSO, DMF, dimethyl acetamide, NMP and acetic acid ethyl ester, preferably methanol, ethanol, isopropanol, dioxane, THF, acetonitrile, acetone, DMF, DMSO, NMP and acetic acid ethyl ester and mixtures thereof.

This reaction is usually carried out at temperatures of from −20 to 100° C., preferably from 0 to 60° C., in the presence of a base where appropriate using a catalyst such as dimethylaminopyridine. Suitable bases are, in general, inorganic compounds, such as alkali metal and alkaline earth metal hydrides, such as lithium hydride, sodium hydride, potassium hydride and calcium hydride, alkali metal and alkaline earth metal carbonates, such as sodium carbonate, lithium carbonate, potassium carbonate and calcium carbonate, and also alkali metal and alkaline earth metal alcoholates such as sodium methanolate, potassium methanolate, potassium tert.-butanolate and dimethoxy-magnesium, moreover organic bases, e.g. tertiary amines, such as trimethylamine, triethylamine, diisopropylethylamine and NMP, pyridine, substituted pyridines, such as collidine, lutidine and 4-dimethylaminopyridine, and also bicyclic amines, preferably sodium hydride, sodium carbonate, potassium methanolate, potassium tert.-butanolate, potassium ethanolate, triethylamine and pyridine. The bases are generally employed in catalytic amounts; however they can also be used in equimolar amounts, in excess or, if appropriate, as solvent. The amount of base is typically 0.1 to 5 molar equivalents, preferably 1 to 2 molar equivalents, relative to 1 mole of compound (IV.a).

The cleavage of the protection groups depicted in the deprotection step may be found in Greene T. W. and Wits P. G. "Protective groups in organic synthesis" (Wiley & Sons, New York, 1999, p. 494 et sqq.).

A further method to obtain compounds (II), wherein $R^2$ is hydrogen and where PG is a protection group as defined above, is shown below:

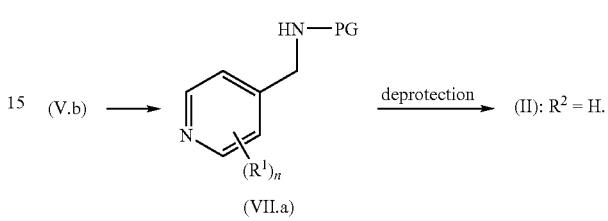

The hydrogenation of the nitriles (V.b) preferably in the presence of suitables catalysts such as Raney nickel or palladium-on-carbon and suitable protection reagents such as di-t-butyl dicarbonate, chloroformate, 2,2,2-trichloroethyl formate, preferably di-t-butyl dicarbonate affords the N-protected compounds (VII.a). On treating with hydrogen bromide/glacial acetic acid or with trifluoroacetic acid/water mixtures or iodotrimethylsilane under neutral, nonhydrolytic conditions or zinc in THF/water mixtures, the compounds (VII.a) can be deprotected to yield compounds (II), wherein $R^2$ is hydrogen.

Compounds (II), wherein $R^1$ is alkoxy, haloalkoxy, alkylthio or haloalkylthio, can be prepared in analogy to standard processes from compounds (VII.a), wherein $R^1$ is halogen, especially chlorine, e.g. in analogy to methods described in J. Heterocycl. Chem. (2005), 42(7), 1369-1379, Tetrahedron Lett. 47(26), 4415-4418, 2006 or Chem. Pharm. Bull. 31(12), 4533-8, 1983. This synthesis route is shown below:

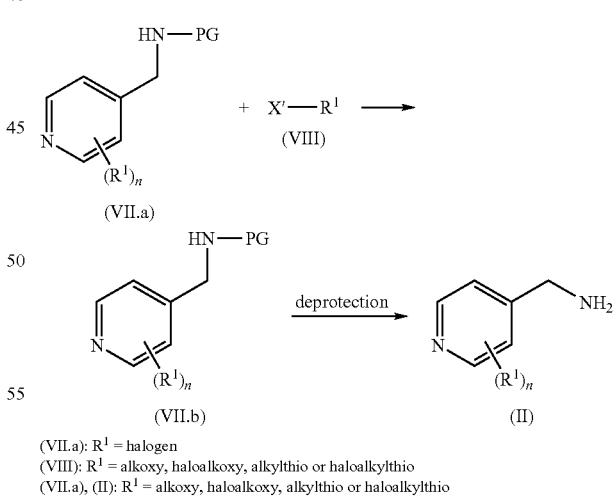

(VII.a): $R^1$ = halogen
(VIII): $R^1$ = alkoxy, haloalkoxy, alkylthio or haloalkylthio
(VII.a), (II): $R^1$ = alkoxy, haloalkoxy, alkylthio or haloalkylthio Compounds (VII.a) are reacted with compounds X'—$R^1$ (also referred to hereinbelow as compounds (VIII)) to obtain compounds (VII.b). Depending on the $R^1$ group to be introduced, the compounds (VIII) are inorganic alkoxides, haloalkoxides, thiolates or halothiolates. The reaction is effected advantageously in an inert solvent. The cation X' in formula (VIII) is of little importance; for practical reasons, ammonium salts, tetraalkylammonium salts such as tetramethylammonium or tetraethylammonium salts, or alkali metal salts or alkaline earth metal salts are typically preferred. Suitable solvents comprise ethers such as dioxane, diethyl ether, MTBE and preferably THF, halogenated hydrocarbons such as DCM or dichloroethane, aromatic hydrocarbons such as toluene, and mixtures thereof. Deprotection of the amino group in formula (VII.b) to obtain compounds (II) can be accomplished as described in for the deprotection of compounds (VII.a) above.

Compounds (II), wherein $R^1$ is alkyl, haloalkyl, alkenyl, alkynyl, cycloalkyl or alkyl-cycloalkyl, can advantageously be prepared by reacting compounds (II), wherein $R^1$ is halogen with organometallic compounds $R^1$-Mt, wherein $R^1$ is alkyl, haloalkyl, alkenyl, alkynyl, cycloalkyl or alkyl-cycloalkyl and Mt is lithium, magnesium or zinc. The reaction is effected preferably in the presence of catalytic or, in particular, at least equimolar amounts of transition metal salts and/or compounds, in particular in the presence of Cu salts such as Cu(I) halides and especially Cu(I) iodide, or Pd-catalyzed. The reaction is effected generally in an inert organic solvent, e.g. one of the aforementioned ethers, in particular THF, an aliphatic or cycloaliphatic hydrocarbon such as hexane, cyclohexane and the like; an aromatic hydrocarbon such as toluene, or in a mixture thereof. The temperatures required for this purpose are in the range of from −100 to +100° C. and especially in the range from −80 to +40° C.

Compounds (III) are known from prior art or can be obtained according to procedures known in the art. A suitable method to obtain compounds (III), wherein L is a leaving group, preferably chlorine, from compounds (IX), wherein m, $R^3$, Het any Y are as above and Hal means halogen, is shown below:

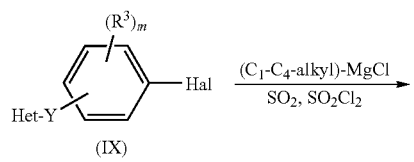

(IX)

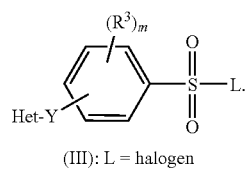

(III): L = halogen

A suitable method to obtain compounds (III) wherein the moiety Het-O is located in para position with respect to the sulfonyl group, from compounds (X), wherein m, $R^3$, Het any Y are as above, is shown below:

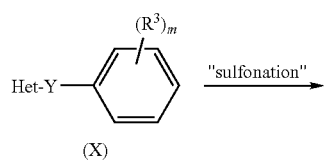

(X)

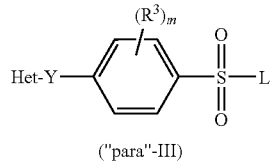

("para"-III)

Sulfonation of the compounds (X) with pyridine-SO$_3$ or dioxane-SO$_3$ complex affords mainly compounds ("para"-III), wherein L is OH (for sulfonation procedure cf. Mizuno, A. et. al., Tetrahedron Lett. 2000, 41, 6605.). Sulfonation of the compounds (X) with oleum under heating affords mainly compounds ("para"-III), wherein L is OH, as well (cf. U.S. Pat. No. 4,874,894). Sulfonation of the compounds (X) with chlorosulfonic acid affords mainly compounds ("para"-III), wherein L is Cl (cf. WO 2003/055857, WO 2003/016313 or WO 2002/64593).

Compounds (X) are known from prior art or can be obtained according to procedures known in the art. A suitable method to obtain compounds (X), wherein Y is —O—, from compounds (XI), wherein Het and Hal are as above, and compounds (XII), wherein m and $R^3$ are as above is shown below:

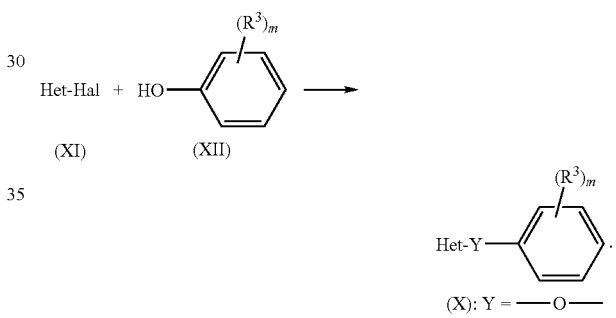

Generally, this reaction is carried out at temperatures from 20 to 210° C., preferably from 40 to 180° C., in an inert organic solvent in the presence of a base and preferably in the presence of a catalyst, such as e.g. KF, KI, 1,4-diazabicyclo[2.2.2]octane (DABCO) or a copper(I) salt such as CuCl or CuI.

Suitable bases are, in general, inorganic compounds such as alkali metal and alkaline earth metal hydrides such as lithium hydride, sodium hydride, potassium hydride and calcium hydride; alkali metal and alkaline earth metal carbonates such as sodium carbonate, lithium carbonate, potassium carbonate and calcium carbonate; and alkali metal and alkaline earth metal alcoholates such as sodium methanolate, potassium methanolate, potassium tert.-butanolate and dimethoxy-magnesium; moreover organic bases, e.g. tertiary amines such as trimethylamine, triethylamine, diisopropylethylamine and NMP; pyridine, substituted pyridines such as collidine, lutidine and 4-dimethylaminopyridine; and also bicyclic amines, preferably sodium hydride, sodium carbonate, potassium methanolate, potassium tert.-butanolate, potassium ethanolate, triethylamine and pyridine. The bases are generally employed in catalytic amounts; however they can also be used in equimolar amounts, in excess or, if appropriate, as solvent. The amount of base is typically 0.1 to 5 molar equivalents, preferably 1 to 2 molar equivalents, relative to 1 mole of compound (XII).

Compounds (XI) and compounds (XII) are known from prior art or can be obtained according to procedures known in the art.

Compounds (I), wherein $R^2$ is hydrogen, can be converted to compounds (I) by conventional processes such as alkylation. Examples of suitable alkylating agents include alkyl halides, such as alkyl chloride, alkyl bromide or alkyl iodide, examples being methyl chloride, methyl bromide or methyl iodide, or dialkyl sulfates such as dimethyl sulfate or diethyl sulfate. The reaction with the alkylating agent is carried out advantageously in the presence of a solvent. Solvents used for these reactions are depending on temperature range—aliphatic, cycloaliphatic or aromatic hydrocarbons such as hexane, cyclohexane, toluene, xylene, chlorinated aliphatic and aromatic hydrocarbons such as DCM, chlorobenzene, open-chain dialkyl ethers such as diethyl ether, di-n-propyl ether, MTBE, cyclic ethers such as THF, 1,4-dioxane, glycol ethers such as dimethyl glycol ether, or mixtures of these solvents.

With respect to their use as intermediates, particular preference is given to the compounds (II), (IV), (V) and (V.a) to (V.e) compiled in the Tables 778 to 789 below, wherein $R^{1a}$, $R^{1b}$, $R^{1c}$ and $R^{1d}$ are each independently hydrogen or have one of the definitions specified for $R^1$ and are selected from lines P-1 to P-37 as described in Table P. In these Tables, $R^{1a}$ denotes the substituent of the pyridin-4-yl group in position 2, $R^{1b}$ denotes the substituent of the pyridin-4-yl group in position 3, $R^{11}$ denotes the substituent of the pyridin-4-yl group in position 5 and $R^{1d}$ denotes the substituent of the pyridin-4-yl group in position 6:

Table 778: Compounds (II), wherein $R^2$ is hydrogen and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 779: Compounds (IV), wherein L is chloro and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 780: Compounds (IV), wherein L is fluoro and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 781: Compounds (IV), wherein L is azido and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 782: Compounds (IV), wherein L is methylsulfonyl and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 783: Compounds (IV), wherein L is toluenesulfonyl and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 784: Compounds (V), wherein X is CH(=NOH) (herein referred to as compounds (V.a)) and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 785: Compounds (V), wherein X is CN (herein referred to as compounds (V.b)) and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 786: Compounds (V), wherein X is C(=O)NH$_2$ (herein referred to as compounds (V.c)) and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 787: Compounds (V), wherein X is CHO (herein referred to as compounds (V.d)) and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 788: Compounds (V), wherein X is $CH_3$ (herein referred to as compounds (V.e)) and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{1d}$ for each individual compound corresponds in each case to one line of Table P.

Table 789: Compounds (V), wherein X is C(=O)OCH$_3$ and $R^{1a}$, $R^{1b}$, $R^{1c}$ and $R^{1d}$ are each independently hydrogen or have one of the definitions specified for $R^1$ and the meaning of $R^{1a}$, $R^{1b}$, $R^{1c}$ and $R^{11d}$ for each individual compound corresponds in each case to one line of Table P.

With respect to their use as intermediates, preference is given to the compounds (III), wherein $R^3$, Y and Het are defined as in claim 1, L is halogen and m is 1, 2, 3 or 4, more preferably m is 1 or 2.

Another embodiment relates to compounds (III), wherein L is chlorine and m is 1, 2, 3 or 4.

A further embodiment relates to compounds (III), wherein Y and Het are defined as in claim 1, L is halogen and $R^3$ is methyl and m is 1 or 2, more preferable L is chlorine.

The N-oxides may be prepared from the compounds (I) according to conventional oxidation methods, e.g. by treating compounds (I) with an organic peracid such as metachloroperbenzoic acid (cf. J. Med. Chem. 38, 1892-1903 (1995) or WO 03/64572); or with inorganic oxidizing agents, e.g. hydrogen peroxide (cf. J. Heterocycl. Chem. 18, 1305-8 (1981)) or oxone (potassium peroxomonosulfate) (cf. J. Am. Chem. Soc. 123, 5962-73 (2001)). The oxidation may lead to pure mono-N-oxides or to a mixture of different N-oxides, which can be separated by conventional methods such as chromatography.

If individual compounds (I) cannot be obtained by the routes described above, they can be prepared by derivatization of other compounds (I).

If the synthesis yields mixtures of isomers, a separation is generally not necessarily required since in some cases the individual isomers can be interconverted during workup for use or during application (e.g. under the action of light, acids or bases). Such conversions may also take place after use, e.g. in the treatment of plants in the treated plant, or in the harmful fungus to be controlled.

The compounds (I) can be present in different crystal modifications whose biological activity may differ. They also form part of the subject matter of the present invention.

The compounds (I) and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds (I) and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

Preferably, compounds (I) and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds (I) and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted posttranstional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinatetolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maizeRIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (*Lepidoptera*) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S. A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia* amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce healthpromoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds (I) and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (Alternaria leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes* black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. Iiriodendri*, teleomorph: *Neonectria liriodendri* Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis* tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*, *Elsinoe* spp. on pome fruits (*E. pyri*), soft fruits (*E. veneta* anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. vertcillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia bidwelli* (black rot) on vines; *Gymnosporangium* spp. on rosaceous plants and junipers, e.g. *G. sabi-*

*nae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Mocrosphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*, stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsic*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimnum* or *P. aphanidermatum*); *Ramularia* spp., e.g. *R. collo-cygno* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. scerotiorum*); *Septoria* spp. on various plants, e.g. *S. glycines* (brown spot) on soybeans, *S. tritici*(*Septoria* blotch) on wheat and *S.* (syn. *Stagonospora*) *nodorum* (*Stagonospora* blotch) on cereals; *Uncinula* (syn. *Erysiphe*) *necator*(powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*, corn smut) and sugar cane; *Venturia* spp. (scab) on apples (e.g. *V. inaequalis*) and pears; and *Verticilium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are particularly suitable for controlling the abovementioned plant diseases in a protective, curative, eradicative, systemic (acropetal and/or basipetal movement) and translaminar manner.

The compounds (I) and compositions thereof, respectively, are also suitable for controlling harmful fungi in the protection of materials (e.g. wood, paper, paint dispersions, fiber or fabrics) and in the protection of stored products. As to the protection of wood and construction materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products the following yeast fungi are worthy of note: *Candida* spp. and *Saccharomyces cerevisae*.

The compounds (I) and compositions thereof, respectively, may be used for improving the health of a plant. The invention also relates to a method for improving plant health by treating a plant, its propagation material and/or the locus where the plant is growing or is to grow with an effective amount of compounds (I) and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect"), quality (e.g. improved content or composition of certain ingredients) and tolerance to abiotic and/or biotic stress. The above identified indicators for the health condition of a plant may be interdependent or may result from each other.

The compounds (I) can be present in different crystal modifications whose biological activity may differ. They are likewise subject matter of the present invention.

The compounds (I) are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds (I) as such or a composition comprising at least one compound (I) prophylactically either at or before planting or transplanting.

The invention also relates to agrochemical compositions comprising a solvent or solid carrier and at least one compound (I) and to the use for controlling harmful fungi.

An agrochemical composition comprises a fungicidally effective amount of a compound (I). The term "effective amount" denotes an amount of the composition or of the compounds (I), which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound (I) used.

The compounds (I), their N-oxides and salts can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 und ff. WO 91/13546, U.S. Pat. No. 4,172,714, U.S. Pat. No. 4,144, 050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as lignin-soulfonic acid (Borrespersе® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol®types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol®23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RSlfrom Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned und the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds (I) and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:
1. Composition Types for Dilution with Water
   i) Water-Soluble Concentrates (SL, LS)
   10 parts by weight of a compound (I) according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.
   ii) Dispersible Concentrates (DC)
   20 parts by weight of a compound (I) according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.
   iii) Emulsifiable Concentrates (EC)
   15 parts by weight of a compound (I) according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
   iv) Emulsions (EW, EO, ES)
   25 parts by weight of a compound (I) according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.
   v) Suspensions (SC, OD, FS)
   In an agitated ball mill, 20 parts by weight of a compound (I) according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.
   vi) Water-dispersible granules and water-soluble granules (WG, SG)
   50 parts by weight of a compound (I) according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.
   vii) Water-dispersible powders and water-soluble powders (WP, SP, SS, WS)
   75 parts by weight of a compound (I) according to the invention are ground in a rotor-stator mill with addition of 25 parts by weight of dispersants, wetting agents and silica gel. Dilution with water gives a stable dispersion or solution of the active substance. The active substance content of the composition is 75% by weight.
   viii) Gel (GF)
   In an agitated ball mill, 20 parts by weight of a compound (I) according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.
2. Composition Types to be Applied Undiluted
   ix) Dustable Powders (DP, DS)
   5 parts by weight of a compound (I) according to the invention are ground finely and mixed intimately with 95 parts by weight of finely divided kaolin. This gives a dustable composition having an active substance content of 5% by weight.
   x) Granules (GR, FG, GG, MG)
   0.5 parts by weight of a compound (I) according to the invention is ground finely and associated with 99.5 parts by weight of carriers. Current methods are extrusion, spraydrying or the fluidized bed. This gives granules to be applied undiluted having an active substance content of 0.5% by weight.
   xi) ULV solutions (UL)
   10 parts by weight of a compound (I) according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-totenfold dilution, active substance concentrations of from 0.01 to 60% by weight, preferably from 0.1 to 40% by weight, in the ready-to-use preparations. Application can be carried out before or during sowing.

Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typcially, a FS comrrposition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e.g. with herbicides, insecticides, growth regulators, fungicides or else with fertilizers, as pre-mix or, if appropriate, not until immeadiately prior to use (tank mix).

Mixing the compounds (I) or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds according to the invention can be used, is intended to illustrate the possible combinations but does not limit them:

A) Strobilurins
   azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxyphenyl)-cyclopropanecarboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) Carboxamides
   carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-3-difluoromethyl-1-methyl-1H-pyrazole-4-carboxamide, N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-3-difluoromethyl-1-methyl-1H-pyrazole-4-carboxamide, N-(2'-chlorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(1,1,2,2- tetrafluoroethoxy)-phenyl]-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide, N-(2-(1,3,3-trimethyl-butyl)-phenyl)-1,3-dimethyl-5-fluoro-1H-pyrazole-4-carboxamide, N-(4'-chloro-3',5'-difluoro-biphenyl-2-yl)-3-difluoromethyl-1-methyl-1H-pyrazole-4-carboxamide, N-(4'-chloro-3',5'-difluoro-biphenyl-2-yl)-3-trifluoromethyl-1-methyl-1H-pyrazole-4-carboxamide, N-(3',4'-dichloro-5'-fluoro-biphenyl-2-yl)-3-trifluoromethyl-1-methyl-1H-pyrazole-4-carboxamide, N-(3',5'-difluoro-4'-methyl-biphenyl-2-yl)-3-difluoromethyl-1-methyl-1H-pyrazole-4-carboxamide, N-(3',5'-difluoro-4'-methyl-biphenyl-2-yl)-3-trifluoromethyl-1-methyl-1H-pyrazole-4-carboxamide, N-[1,2,3,4-tetrahydro-9-(1-methylethyl)-1,4-methanonaphthalen-5-yl]-3-(difluoromethyl)-1-methyl-1H-pyrazole-4-carboxamide;

carboxylic morpholides: dimethomorph, flumorph;

benzoic acid amides: flumetover, fluopicolde, fluopyram, zoxamide, N-(3-Ethyl-3,5,5-trimethyl-cyclohexyl)-3-formylamino-2-hydroxy-benzamide;

other carboxamides: carpropamid, dicyclomet, mandiproamid, oxytetracyclin, silthiofarm and N-(6-methoxy-pyridin-3-yl)cyclopropanecarboxylic acid amide;

C) Azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) Heterocyclic Compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloro-nicotinamide, N-[(5-bromo-3-chloro-pyridin-2-yl)-methyl]-2,4-dichloro-nicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydropyrazole-1-carbothioic acid S-allyl ester;

others: acibenzolar-5-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine, 6-(3,4-dichloro-phenyl)-5-methyl-[1,2,4]triazolo[1,5-a]pyrimidine-7-ylamine, 6-(4-tert-butylphenyl)-5-methyl-[1,2,4]triazolo[1,5-a]pyrimidine-7-ylamine, 5-methyl-6-(3,5,5-trimethyl-hexyl)-[1,2,4]triazolo[1,5-a]pyrimidine-7-ylamine, 5-methyl-6-octyl-[1,2,4]triazolo[1,5-a]pyrimidine-7-ylamine, 6-methyl-5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethyl-hexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl-[1,2,4]triazolo[1,5-a]pyrimidine-7-ylamine and 5-trifluoromethyl-6-(3,5,5-trimethyl-hexyl)-[1,2,4]triazolo[1,5-a]pyrimidine-7-ylamine;

E) carbamates thio- and dithiocarbamates: ferbam, mancozeb, maneb, metam, methasulphocarb, metiram, propineb, thiram, zineb, ziram;

carbamates: benthiavalicarb, diethofencarb, benthiavalicarb, iprovalicarb, propamocarb, propamocarb hydrochlorid, valiphenal and N-(1-(1-(4-cyano-phenyl)ethanesulfonyl)-but-2-yl)carbamic acid-(4-fluorophenyl)ester;

F) Other Active Substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methylbenzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethylN-methyl formamidine, N'-(4-(4- fluoro-3-trifluoromethyl-phenoxy)-2,5-dimethylphenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester.

G) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

H) herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cynalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluorophenyl)-pyridine-2-carboxylic acid methyl ester.

I) insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound (I) (component 1) and at least one further active substance useful for plant protection, e.g. selected from the groups A) to I) (component 2), in particular one further fungicide, e.g. one or more fungicide from the groups A) to F), as described above, and if desired one suitable solvent or solid carrier. Those mixtures are of particular interest, since many of them at the same application rate show higher efficiencies against harmful fungi. Furthermore, combating harmful fungi with a mixture of compounds (I) and at least one fungicide from groups A) to F), as described above, is more efficient than combating those fungi with individual compounds (I) or individual fungicides from groups A) to F). By applying compounds (I) together with at least one active substance from groups A) to I) a synergistic effect can be obtained, i.e. more then simple addition of the individual effects is obtained (synergistic mixtures).

According to this invention, applying the compounds (I) together with at least one further active substance is to be understood to denote, that at least one compound (I) and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying the compounds (I) and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound (I) (component 1) and one further active substance (component 2), e.g. one active substance from groups A) to I), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound (I) (component 1) and a first further active substance (component 2) and a second further active substance (component 3), e.g. two active substances from groups A) to I), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include one or more fungicide component(s) and/or an adjuvant component and/or a insecticide component and/or a growth regulator component and/or a herbicde. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e.g. components comprising compounds (I) and/or active substances from the groups A) to I), may be mixed by the user in a spray tank and further auxiliaries and additives may be added, if appropriate (tank mix).

In a further embodiment, either individual components of the composition according to the invention or partially premixed components, e.g. components comprising compounds (I) and/or active substances from the groups A) to I), can be applied jointly (e.g. after tankmix) or consecutively.

Preference is also given to mixtures comprising a compound (I) (component 1) and at least one active substance selected from the strobilurines of group A) (component 2) and particularly selected from azoxystrobin, dimoxystrobin, fluoxastrobin, kresoxim-methyl, orysastrobin, picoxystrobin, pyraclostrobin and trifloxystrobin.

Preference is also given to mixtures comprising a compound (I) (component 1) and at least one active substance selected from the carboxamides of group B) (component 2) and particularly selected from bixafen, boscalid, sedaxane, fenhexamid, metalaxyl, mefenoxam, ofurace, dimethomorph, flumorph, fluopicolid (picobenzamid), zoxamide, carpropamid and mandipropamid.

Preference is given to mixtures comprising a compound (I) (component 1) and at least one active substance selected from the azoles of group C) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Preference is also given to mixtures comprising a compound (I) (component 1) and at least one active substance selected from the heterocyclic compounds of group D) (component 2) and particularly selected from fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil and quinoxyfen.

Preference is also given to mixtures comprising a compound (I) (component 1) and at least one active substance selected from the carbamates of group E) (component 2) and particularly selected from mancozeb, metiram, propineb, thiram, iprovalicarb, benthiavalicarb and propamocarb.

Preference is also given to mixtures comprising a compound (I) (component 1) and at least one active substance selected from the fungicides given in group F) (component 2) and particularly selected from dithianon, fentin salts, such as fentin acetate, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone, spiroxamine and 5-chloro-7-(4-methylpiperidin-1-yl)-6-(2,4,6-trifluorophenyl)-[1,2,4]-triazolo[1,5-a]pyrimidine.

Accordingly, the present invention furthermore relates to compositions comprising one compound (I) (component 1) and one further active substance (component 2), which further active substance is selected from the column "Component 2" of the lines B-1 to B-375 of Table B.

A further embodiment relates to the compositions B-1 to B-375 listed in Table B, where a row of Table B corresponds in each case to a fungicidal composition comprising one of the in the present specification individualized compounds (I) (component I) and the respective further active substance (component 2) stated in the row in question. Preferably, the compositions described comprise the active substances in synergistically effective amounts.

TABLE B

Composition comprising one indiviualized compound (I) and one further active substance from groups A) bis F)

| Mixture | Component 1 | Component 2 |
| --- | --- | --- |
| B-1 | one individualized compound (I) | Azoxystrobin |
| B-2 | one individualized compound (I) | Dimoxystrobin |
| B-3 | one individualized compound (I) | Enestroburin |
| B-4 | one individualized compound (I) | Fluoxastrobin |
| B-5 | one individualized compound (I) | Kresoxim-methyl |
| B-6 | one individualized compound (I) | Metominostrobin |
| B-7 | one individualized compound (I) | Orysastrobin |
| B-8 | one individualized compound (I) | Picoxystrobin |
| B-9 | one individualized compound (I) | Pyraclostrobin |
| B-10 | one individualized compound (I) | Pyribencarb |
| B-11 | one individualized compound (I) | Trifloxystrobin |
| B-12 | one individualized compound (I) | 2-(2-(6-(3-Chloro-2-methyl-phenoxy)-5-fluoro-pyrimidin-4-yloxy)-phenyl)-2-methoxyimino-N-methyl-acetamide |
| B-13 | one individualized compound (I) | 2-(ortho-((2,5-Dimethylphenyl-oxy-methylen)phenyl)-3-methoxy-acrylsauremethylester |
| B-14 | one individualized compound (I) | 3-Methoxy-2-(2-(N-(4-methoxy-phenyl)-cyclopropanecarboximidoylsulfanylmethyl)-phenyl)-acrylic acid methyl ester |
| B-15 | one individualized compound (I) | 2-(2-(3-(2,6-dichlorophenyl)-1-methyl-allylideneaminooxymethyl)-phenyl)-2-methoxyimino-N-methyl-acetamide |
| B-16 | one individualized compound (I) | Benalaxyl |
| B-17 | one individualized compound (I) | Benalaxyl-M |
| B-18 | one individualized compound (I) | Benodanil |
| B-19 | one individualized compound (I) | Bixafen |
| B-20 | one individualized compound (I) | Boscalid |
| B-21 | one individualized compound (I) | Carboxin |

TABLE B-continued

Composition comprising one indiviualized compound (I) and one further active substance from groups A) bis F)

| Mixture | Component 1 | Component 2 |
|---|---|---|
| B-22 | one individualized compound (I) | Fenfuram |
| B-23 | one individualized compound (I) | Fenhexamid |
| B-24 | one individualized compound (I) | Flutolanil |
| B-25 | one individualized compound (I) | Furametpyr |
| B-26 | one individualized compound (I) | Isopyrazam |
| B-27 | one individualized compound (I) | Isotianil |
| B-28 | one individualized compound (I) | Kiralaxyl |
| B-29 | one individualized compound (I) | Mepronil |
| B-30 | one individualized compound (I) | Metalaxyl |
| B-31 | one individualized compound (I) | Metalaxyl-M |
| B-32 | one individualized compound (I) | Ofurace |
| B-33 | one individualized compound (I) | Oxadixyl |
| B-34 | one individualized compound (I) | Oxycarboxin |
| B-35 | one individualized compound (I) | Penthiopyrad |
| B-36 | one individualized compound (I) | Sedaxane |
| B-37 | one individualized compound (I) | Tecloftalam |
| B-38 | one individualized compound (I) | Thifluzamide |
| B-39 | one individualized compound (I) | Tiadinil |
| B-40 | one individualized compound (I) | 2-Amino-4-methyl-thiazole-5-carboxylic acid anilide |
| B-41 | one individualized compound (I) | 2-Chloro-N-(1,1,3-trimethyl-indan-4-yl)-nicotinamide |
| B-42 | one individualized compound (I) | N-(2',4'-difluorobiphenyl-2-yl)-3-difluoromethyl-1-methyl-1H-pyrazole-4-carboxamide |
| B-43 | one individualized compound (I) | N-(2',4'-dichlorobiphenyl-2-yl)-3-difluoromethyl-1-methyl-1H-pyrazole-4-carboxamide |
| B-44 | one individualized compound (I) | N-(2',5'-difluorobiphenyl-2-yl)-3-difluoromethyl-1-methyl-1H-pyrazole-4-carboxamide |
| B-45 | one individualized compound (I) | N-(2',5'-dichlorobiphenyl-2-yl)-3-difluoromethyl-1-methyl-1H-pyrazole-4-carboxamide |
| B-46 | one individualized compound (I) | N-(3',5'-difluorobiphenyl-2-yl)-3-difluoromethyl-1-methyl-1H-pyrazole-4-carboxamide |
| B-47 | one individualized compound (I) | N-(3',5'-dichlorobiphenyl-2-yl)-3-difluoromethyl-1-methyl-1H-pyrazole-4-carboxamide |
| B-48 | one individualized compound (I) | N-(3'-fluorobiphenyl-2-yl)-3-difluoromethyl-1-methyl-1H-pyrazole-4-carboxamide |
| B-49 | one individualized compound (I) | N-(3'-chlorobiphenyl-2-yl)-3-difluoromethyl-1-methyl-1H-pyrazole-4-carboxamide |
| B-50 | one individualized compound (I) | N-(2'-fluorobiphenyl-2-yl)-3-difluoromethyl-1-methyl-1H-pyrazole-4-carboxamide |
| B-51 | one individualized compound (I) | N-(2'-chlorobiphenyl-2-yl)-3-difluoromethyl-1-methyl-1H-pyrazole-4-carboxamide |
| B-52 | one individualized compound (I) | N-(3',4',5'-trifluorobiphenyl-2-yl)-3-difluoromethyl-1-methyl-1H-pyrazole-4-carboxamide |
| B-53 | one individualized compound (I) | N-(2',4',5'-trifluorobiphenyl-2-yl)-3-difluoromethyl-1-methyl-1H-pyrazole-4-carboxamide |
| B-54 | one individualized compound (I) | N-[2-(1,1,2,3,3,3-hexafluoropropoxy)-phenyl]-3-difluoromethyl-1-methyl-1H-pyrazole-4-carboxamide |
| B-55 | one individualized compound (I) | N-[2-(1,1,2,2-tetrafluoroethoxy)-phenyl]-3-difluoromethyl-1-methyl-1H-pyrazole-4-carboxamide |
| B-56 | one individualized compound (I) | N-(4'-trifluoromethylthiobiphenyl-2-yl)-3-difluoromethyl-1-methyl-1H-pyrazole-4-carboxamide |
| B-57 | one individualized compound (I) | N-(2-(1,3-dimethyl-butyl)-phenyl)-1,3-dimethyl-5-fluoro-1H-pyrazole-4-carboxamide |
| B-58 | one individualized compound (I) | N-(2-(1,3,3-trimethyl-butyl)-phenyl)-1,3-dimethyl-5-fluoro-1H-pyrazole-4-carboxamide |

TABLE B-continued

Composition comprising one indiviualized compound (I) and one further active substance from groups A) bis F)

| Mixture | Component 1 | Component 2 |
|---|---|---|
| B-59 | one individualized compound (I) | N-(4'-chloro-3',5'-difluoro-biphenyl-2-yl)-3-difluoromethyl-1-methyl-1H-pyrazole-4-carboxamide |
| B-60 | one individualized compound (I) | N-(4'-chloro-3',5'-difluoro-biphenyl-2-yl)-3-trifluoromethyl-1-methyl-1H-pyrazole-4-carboxamide |
| B-61 | one individualized compound (I) | N-(3',4'-dichloro-5'-fluoro-biphenyl-2-yl)-3-trifluoromethyl-1-methyl-1H-pyrazole-4-carboxamide |
| B-62 | one individualized compound (I) | N-(3',5'-difluoro-4'-methyl-biphenyl-2-yl)-3-difluoromethyl-1-methyl-1H-pyrazole-4-carboxamide |
| B-63 | one individualized compound (I) | N-(3',5'-difluoro-4'-methyl-biphenyl-2-yl)-3-trifluoromethyl-1-methyl-1H-pyrazole-4-carboxamide |
| B-64 | one individualized compound (I) | N-[1,2,3,4-tetrahydro-9-(1-methylethyl)-1,4-methanonaphthalen-5-yl]-3-(difluoromethyl)-1-methyl-1H-pyrazole-4-carboxamide |
| B-65 | one individualized compound (I) | Dimethomorph |
| B-66 | one individualized compound (I) | Flumorph |
| B-67 | one individualized compound (I) | Flumetover |
| B-68 | one individualized compound (I) | Fluopicolide |
| B-69 | one individualized compound (I) | Fluopyram |
| B-70 | one individualized compound (I) | Zoxamide |
| B-71 | one individualized compound (I) | N-(3-Ethyl-3,5,5-trimethyl-cyclohexyl)-3-formylamino-2-hydroxy-benzamide |
| B-72 | one individualized compound (I) | Carpropamid |
| B-73 | one individualized compound (I) | Diclocymet |
| B-74 | one individualized compound (I) | Mandipropamid |
| B-75 | one individualized compound (I) | Oxytetracyclin |
| B-76 | one individualized compound (I) | Silthiofam |
| B-77 | one individualized compound (I) | N-(6-methoxy-pyridin-3-yl)cyclopropanecarboxylic acid amide |
| B-78 | one individualized compound (I) | Azaconazole |
| B-79 | one individualized compound (I) | Bitertanol |
| B-80 | one individualized compound (I) | Bromuconazole |
| B-81 | one individualized compound (I) | Cyproconazole |
| B-82 | one individualized compound (I) | Difenoconazole |
| B-83 | one individualized compound (I) | Diniconazole |
| B-84 | one individualized compound (I) | Diniconazole-M |
| B-85 | one individualized compound (I) | Epoxiconazole |
| B-86 | one individualized compound (I) | Fenbuconazole |
| B-87 | one individualized compound (I) | Fluquinconazole |
| B-88 | one individualized compound (I) | Flusilazole |
| B-89 | one individualized compound (I) | Flutriafol |
| B-90 | one individualized compound (I) | Hexaconazol |
| B-91 | one individualized compound (I) | Imibenconazole |
| B-92 | one individualized compound (I) | Ipconazole |
| B-93 | one individualized compound (I) | Metconazole |
| B-94 | one individualized compound (I) | Myclobutanil |
| B-95 | one individualized compound (I) | Oxpoconazol |
| B-96 | one individualized compound (I) | Paclobutrazol |
| B-97 | one individualized compound (I) | Penconazole |
| B-98 | one individualized compound (I) | Propiconazole |
| B-99 | one individualized compound (I) | Prothioconazole |
| B-100 | one individualized compound (I) | Simeconazole |
| B-101 | one individualized compound (I) | Tebuconazole |
| B-102 | one individualized compound (I) | Tetraconazole |
| B-103 | one individualized compound (I) | Triadimefon |
| B-104 | one individualized compound (I) | Triadimenol |
| B-105 | one individualized compound (I) | Triticonazole |
| B-106 | one individualized compound (I) | Uniconazole |
| B-107 | one individualized compound (I) | 1-(4-Chloro-phenyl)-2-([1,2,4]triazol-1-yl)-cycloheptanol |
| B-108 | one individualized compound (I) | Cyazofamid |
| B-109 | one individualized compound (I) | Imazalil |
| B-110 | one individualized compound (I) | Imazalil-sulfate |
| B-111 | one individualized compound (I) | Pefurazoate |
| B-112 | one individualized compound (I) | Prochloraz |
| B-113 | one individualized compound (I) | Triflumizole |
| B-114 | one individualized compound (I) | Benomyl |
| B-115 | one individualized compound (I) | Carbendazim |
| B-116 | one individualized compound (I) | Fuberidazole |
| B-117 | one individualized compound (I) | Thiabendazole |

TABLE B-continued

Composition comprising one indiviualized compound (I) and one further active substance from groups A) bis F)

| Mixture | Component 1 | Component 2 |
|---|---|---|
| B-118 | one individualized compound (I) | Ethaboxam |
| B-119 | one individualized compound (I) | Etridiazole |
| B-120 | one individualized compound (I) | Hymexazole |
| B-121 | one individualized compound (I) | 2-(4-Chloro-phenyl)-N-[4-(3,4-dimethoxy-phenyl)-isoxazol-5-yl]-2-prop-2-yn-yloxy-acetamide |
| B-122 | one individualized compound (I) | Fluazinam |
| B-123 | one individualized compound (I) | Pyrifenox |
| B-124 | one individualized compound (I) | 3-[5-(4-Chloro-phenyl)-2,3-dimethyl-isoxazolidin-3-yl]-pyridine |
| B-125 | one individualized compound (I) | 3-[5-(4-Methyl-phenyl)-2,3-dimethyl-isoxazolidin-3-yl]-pyridine |
| B-126 | one individualized compound (I) | 2,3,5,6-Tetrachloro-4-methanesulfonyl-pyridine |
| B-127 | one individualized compound (I) | 3,4,5-Trichloro-pyridine-2,6-dicarbonitrile |
| B-128 | one individualized compound (I) | N-(1-(5-Bromo-3-chloro-pyridin-2-yl)-ethyl)-2,4-dichloro-nicotinamide |
| B-129 | one individualized compound (I) | N-((5-Bromo-3-chloro-pyridin-2-yl)-methyl)-2,4-dichloro-nicotinamide |
| B-130 | one individualized compound (I) | Bupirimate |
| B-131 | one individualized compound (I) | Cyprodinil |
| B-132 | one individualized compound (I) | Diflumetorim |
| B-133 | one individualized compound (I) | Fenarimol |
| B-134 | one individualized compound (I) | Ferimzone |
| B-135 | one individualized compound (I) | Mepanipyrim |
| B-136 | one individualized compound (I) | Nitrapyrin |
| B-137 | one individualized compound (I) | Nuarimol |
| B-138 | one individualized compound (I) | Pyrimethanil |
| B-139 | one individualized compound (I) | Triforine |
| B-140 | one individualized compound (I) | Fenpiclonil |
| B-141 | one individualized compound (I) | Fludioxonil |
| B-142 | one individualized compound (I) | Aldimorph |
| B-143 | one individualized compound (I) | Dodemorph |
| B-144 | one individualized compound (I) | Dodemorph-acetate |
| B-145 | one individualized compound (I) | Fenpropimorph |
| B-146 | one individualized compound (I) | Tridemorph |
| B-147 | one individualized compound (I) | Fenpropidin |
| B-148 | one individualized compound (I) | Fluoroimid |
| B-149 | one individualized compound (I) | Iprodione |
| B-150 | one individualized compound (I) | Procymidone |
| B-151 | one individualized compound (I) | Vinclozolin |
| B-152 | one individualized compound (I) | Famoxadone |
| B-153 | one individualized compound (I) | Fenamidone |
| B-154 | one individualized compound (I) | Flutianil |
| B-155 | one individualized compound (I) | Octhilinone |
| B-156 | one individualized compound (I) | Probenazole |
| B-157 | one individualized compound (I) | 5-Amino-2-iso-propyl-4-ortho-tolyl-2,3-dihydro-pyrazole-1-carbothioic acid S-allyl ester |
| B-158 | one individualized compound (I) | Acibenzolar-S-methyl |
| B-159 | one individualized compound (I) | Amisulbrom |
| B-160 | one individualized compound (I) | Anilazin |
| B-161 | one individualized compound (I) | Blasticidin-S |
| B-162 | one individualized compound (I) | Captafol |
| B-163 | one individualized compound (I) | Captan |
| B-164 | one individualized compound (I) | Chinomethionat |
| B-165 | one individualized compound (I) | Dazomet |
| B-166 | one individualized compound (I) | Debacarb |
| B-167 | one individualized compound (I) | Diclomezine |
| B-168 | one individualized compound (I) | Difenzoquat, |
| B-169 | one individualized compound (I) | Difenzoquat-methylsulfate |
| B-170 | one individualized compound (I) | Fenoxanil |
| B-171 | one individualized compound (I) | Folpet |
| B-172 | one individualized compound (I) | Oxolinsaure |
| B-173 | one individualized compound (I) | Piperalin |
| B-174 | one individualized compound (I) | Proquinazid |
| B-175 | one individualized compound (I) | Pyroquilon |
| B-176 | one individualized compound (I) | Quinoxyfen |
| B-177 | one individualized compound (I) | Triazoxid |
| B-178 | one individualized compound (I) | Tricyclazole |
| B-179 | one individualized compound (I) | 2-Butoxy-6-iodo-3-propyl-chromen-4-one |
| B-180 | one individualized compound (I) | 5-Chloro-1-(4,6-dimethoxy-pyrimidin-2-yl)-2-methyl-1H-benzoimidazole |

TABLE B-continued

Composition comprising one indiviualized compound (I) and one further active substance from groups A) bis F)

| Mixture | Component 1 | Component 2 |
|---|---|---|
| B-181 | one individualized compound (I) | 5-Chloro-7-(4-methyl-piperidin-1-yl)-6-(2,4,6-trifluoro-phenyl)-[1,2,4]triazolo[1,5-a]pyrimidine |
| B-182 | one individualized compound (I) | 6-(3,4-dichloro-phenyl)-5-methyl-[1,2,4]triazolo[1,5-a]pyrimidine-7-ylamine |
| B-183 | one individualized compound (I) | 6-(4-tert-butylphenyl)-5-methyl-[1,2,4]triazolo[1,5-a]pyrimidine-7-ylamine |
| B-184 | one individualized compound (I) | 5-methyl-6-(3,5,5-trimethyl-hexyl)-[1,2,4]triazolo[1,5-a]pyrimidine-7-ylamine |
| B-185 | one individualized compound (I) | 5-methyl-6-octyl-[1,2,4]triazolo[1,5-a]-pyrimidine-7-ylamine |
| B-186 | one individualized compound (I) | 6-methyl-5-octyl-[1,2,4]triazolo[1,5-a]pyrimidine-7-ylamine |
| B-187 | one individualized compound (I) | 6-ethyl-5-octyl-[1,2,4]triazolo[1,5-a]pyrimidine-7-ylamine |
| B-188 | one individualized compound (I) | 5-ethyl-6-octyl-[1,2,4]triazolo[1,5-a]pyrimidine-7-ylamine |
| B-189 | one individualized compound (I) | 5-ethyl-6-(3,5,5-trimethyl-hexyl)-[1,2,4]triazolo[1,5-a]pyrimidine-7-ylamine |
| B-190 | one individualized compound (I) | 6-octyl-5-propyl-[1,2,4]triazolo[1,5-a]pyrimidine-7-ylamine |
| B-191 | one individualized compound (I) | 5-methoxymethyl-6-octyl-[1,2,4]triazolo[1,5-a]pyrimidine-7-ylamine |
| B-192 | one individualized compound (I) | 6-octyl-5-trifluoromethyl-[1,2,4]triazolo[1,5-a]pyrimidine-7-ylamine |
| B-193 | one individualized compound (I) | 5-trifluoromethyl-6-(3,5,5-trimethyl-hexyl)-[1,2,4]triazolo[1,5-a]pyrimidine-7-ylamine, |
| B-194 | one individualized compound (I) | Ferbam |
| B-195 | one individualized compound (I) | Mancozeb |
| B-196 | one individualized compound (I) | Maneb |
| B-197 | one individualized compound (I) | Metam |
| B-198 | one individualized compound (I) | Methasulphocarb |
| B-199 | one individualized compound (I) | Metiram |
| B-200 | one individualized compound (I) | Propineb |
| B-201 | one individualized compound (I) | Thiram |
| B-202 | one individualized compound (I) | Zineb |
| B-203 | one individualized compound (I) | Ziram |
| B-204 | one individualized compound (I) | Diethofencarb |
| B-205 | one individualized compound (I) | Benthiavalicarb |
| B-206 | one individualized compound (I) | Iprovalicarb |
| B-207 | one individualized compound (I) | Propamocarb |
| B-208 | one individualized compound (I) | Propamocarb hydrochlorid |
| B-209 | one individualized compound (I) | Valiphenal |
| B-210 | one individualized compound (I) | N-(1-(1-(4-cyanophenyl)ethanesulfonyl)-but-2-yl)carbamic acid-(4-fluorophenyl) ester |
| B-211 | one individualized compound (I) | Dodine |
| B-212 | one individualized compound (I) | Dodine free base |
| B-213 | one individualized compound (I) | Guazatine |
| B-214 | one individualized compound (I) | Guazatine-acetate |
| B-215 | one individualized compound (I) | Iminoctadine |
| B-216 | one individualized compound (I) | Iminoctadine-triacetate |
| B-217 | one individualized compound (I) | Iminoctadine-tris(albesilate) |
| B-218 | one individualized compound (I) | Kasugamycin |
| B-219 | one individualized compound (I) | Kasugamycin-hydrochloride-hydrate |
| B-220 | one individualized compound (I) | Polyoxine |
| B-221 | one individualized compound (I) | Streptomycin |
| B-222 | one individualized compound (I) | Validamycin A |
| B-223 | one individualized compound (I) | Binapacryl |
| B-224 | one individualized compound (I) | Dicloran |
| B-225 | one individualized compound (I) | Dinobuton |
| B-226 | one individualized compound (I) | Dinocap |
| B-227 | one individualized compound (I) | Nitrothal-isopropyl |
| B-228 | one individualized compound (I) | Tecnazen |
| B-229 | one individualized compound (I) | Fentin salts |
| B-230 | one individualized compound (I) | Dithianon |
| B-231 | one individualized compound (I) | Isoprothiolane |
| B-232 | one individualized compound (I) | Edifenphos |
| B-233 | one individualized compound (I) | Fosetyl, Fosetyl-aluminium |
| B-234 | one individualized compound (I) | Iprobenfos |

TABLE B-continued

Composition comprising one indiviualized compound (I) and one further active substance from groups A) bis F)

| Mixture | Component 1 | Component 2 |
|---|---|---|
| B-235 | one individualized compound (I) | Phosphorous acid ($H_3PO_3$) and derivatives |
| B-236 | one individualized compound (I) | Pyrazophos |
| B-237 | one individualized compound (I) | Tolclofos-methyl |
| B-238 | one individualized compound (I) | Chlorothalonil |
| B-239 | one individualized compound (I) | Dichlofluanid |
| B-240 | one individualized compound (I) | Dichlorophen |
| B-241 | one individualized compound (I) | Flusulfamide |
| B-242 | one individualized compound (I) | Hexachlorbenzene |
| B-243 | one individualized compound (I) | Pencycuron |
| B-244 | one individualized compound (I) | Pentachlorophenol and salts |
| B-245 | one individualized compound (I) | Phthalide |
| B-246 | one individualized compound (I) | Quintozene |
| B-247 | one individualized compound (I) | Thiophanate Methyl |
| B-248 | one individualized compound (I) | Tolylfluanid |
| B-249 | one individualized compound (I) | N-(4-chloro-2-nitro-phenyl)-N-ethyl-4-methyl-benzenesulfonamide |
| B-250 | one individualized compound (I) | Bordeaux mixture |
| B-251 | one individualized compound (I) | Copper acetate |
| B-252 | one individualized compound (I) | Copper hydroxide |
| B-253 | one individualized compound (I) | Copper oxychloride |
| B-254 | one individualized compound (I) | basic Copper sulfate |
| B-255 | one individualized compound (I) | Sulfur |
| B-256 | one individualized compound (I) | Biphenyl |
| B-257 | one individualized compound (I) | Bronopol |
| B-258 | one individualized compound (I) | Cyflufenamid |
| B-259 | one individualized compound (I) | Cymoxanil |
| B-260 | one individualized compound (I) | Diphenylamin |
| B-261 | one individualized compound (I) | Metrafenone |
| B-262 | one individualized compound (I) | Mildiomycin |
| B-263 | one individualized compound (I) | Oxin-copper |
| B-264 | one individualized compound (I) | Prohexadione calcium |
| B-265 | one individualized compound (I) | Spiroxamine |
| B-266 | one individualized compound (I) | Tolylfluanid |
| B-267 | one individualized compound (I) | N-(Cyclopropylmethoxyimino-(6-difluoromethoxy-2,3-difluoro-phenyl)-methyl)-2-phenyl acetamide |
| B-268 | one individualized compound (I) | N'-(4-(4-chloro-3-trifluoromethyl-phenoxy)-2,5-dimethyl-phenyl)-N-ethyl-N-methyl formamidine |
| B-269 | one individualized compound (I) | N'-(4-(4-fluoro-3-trifluoromethyl-phenoxy)-2,5-dimethyl-phenyl)-N-ethyl-N-methyl formamidine |
| B-270 | one individualized compound (I) | N'-(2-methyl-5-trifluoromethyl-4-(3-tri-methylsilanyl-propoxy)-phenyl)-N-ethyl-N-methyl formamidine |
| B-271 | one individualized compound (I) | N'-(5-difluoromethyl-2-methyl-4-(3-tri-methylsilanyl-propoxy)-phenyl)-N-ethyl-N-methyl formamidine |
| B-272 | one individualized compound (I) | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-273 | one individualized compound (I) | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-274 | one individualized compound (I) | Acetic acid 6-tert.-butyl-8-fluoro-2,3-dimethyl-quinolin-4-yl ester |
| B-275 | one individualized compound (I) | Methoxy-acetic acid 6-tert-butyl-8-fluoro-2,3-dimethyl-quinolin-4-yl ester |
| B-276 | one individualized compound (I) | Carbaryl |
| B-277 | one individualized compound (I) | Carbofuran |
| B-278 | one individualized compound (I) | Carbosulfan |
| B-279 | one individualized compound (I) | Methomylthiodicarb |
| B-280 | one individualized compound (I) | Bifenthrin |
| B-281 | one individualized compound (I) | Cyfluthrin |
| B-282 | one individualized compound (I) | Cypermethrin |
| B-283 | one individualized compound (I) | alpha-Cypermethrin |
| B-284 | one individualized compound (I) | zeta-Cypermethrin |
| B-285 | one individualized compound (I) | Deltamethrin |
| B-286 | one individualized compound (I) | Esfenvalerate |
| B-287 | one individualized compound (I) | Lambda-cyhalothrin |

TABLE B-continued

Composition comprising one indiviualized compound (I) and one further active substance from groups A) bis F)

| Mixture | Component 1 | Component 2 |
|---|---|---|
| B-288 | one individualized compound (I) | Permethrin |
| B-289 | one individualized compound (I) | Tefluthrin |
| B-290 | one individualized compound (I) | Diflubenzuron |
| B-291 | one individualized compound (I) | Flufenoxuron |
| B-292 | one individualized compound (I) | Lufenuron |
| B-293 | one individualized compound (I) | Teflubenzuron |
| B-294 | one individualized compound (I) | Spirotetramate |
| B-295 | one individualized compound (I) | Clothianidin |
| B-296 | one individualized compound (I) | Dinotefuran |
| B-297 | one individualized compound (I) | Imidacloprid |
| B-298 | one individualized compound (I) | Thiamethoxam |
| B-299 | one individualized compound (I) | Acetamiprid |
| B-300 | one individualized compound (I) | Thiacloprid |
| B-301 | one individualized compound (I) | Endosulfan |
| B-302 | one individualized compound (I) | Fipronil |
| B-303 | one individualized compound (I) | Abamectin |
| B-304 | one individualized compound (I) | Emamectin |
| B-305 | one individualized compound (I) | Spinosad |
| B-306 | one individualized compound (I) | Spinetoram |
| B-307 | one individualized compound (I) | Hydramethylnon |
| B-308 | one individualized compound (I) | Chlorfenapyr |
| B-309 | one individualized compound (I) | Fenbutatin oxide |
| B-310 | one individualized compound (I) | Indoxacarb |
| B-311 | one individualized compound (I) | Metaflumizone |
| B-312 | one individualized compound (I) | Flonicamid |
| B-313 | one individualized compound (I) | Lubendiamide |
| B-314 | one individualized compound (I) | Chlorantraniliprole |
| B-315 | one individualized compound (I) | Cyazypyr (HGW86) |
| B-316 | one individualized compound (I) | Cyflumetofen |
| B-317 | one individualized compound (I) | Acetochlor |
| B-318 | one individualized compound (I) | Dimethenamid |
| B-319 | one individualized compound (I) | metolachlor |
| B-320 | one individualized compound (I) | Metazachlor |
| B-321 | one individualized compound (I) | Glyphosate |
| B-322 | one individualized compound (I) | Glufosinate |
| B-323 | one individualized compound (I) | Sulfosate |
| B-324 | one individualized compound (I) | Clodinafop |
| B-325 | one individualized compound (I) | Fenoxaprop |
| B-326 | one individualized compound (I) | Fluazifop |
| B-327 | one individualized compound (I) | Haloxyfop |
| B-328 | one individualized compound (I) | Paraquat |
| B-329 | one individualized compound (I) | Phenmedipham |
| B-330 | one individualized compound (I) | Clethodim |
| B-331 | one individualized compound (I) | Cycloxydim |
| B-332 | one individualized compound (I) | Profoxydim |
| B-333 | one individualized compound (I) | Sethoxydim |
| B-334 | one individualized compound (I) | Tepraloxydim |
| B-335 | one individualized compound (I) | Pendimethalin |
| B-336 | one individualized compound (I) | Prodiamine |
| B-337 | one individualized compound (I) | Trifluralin |
| B-338 | one individualized compound (I) | Acifluorfen |
| B-339 | one individualized compound (I) | Bromoxynil |
| B-340 | one individualized compound (I) | Imazamethabenz |
| B-341 | one individualized compound (I) | Imazamox |
| B-342 | one individualized compound (I) | Imazapic |
| B-343 | one individualized compound (I) | Imazapyr |
| B-344 | one individualized compound (I) | Imazaquin |
| B-345 | one individualized compound (I) | Imazethapyr |
| B-346 | one individualized compound (I) | 2,4-Dichlorophenoxyacetic acid (2,4-D) |
| B-347 | one individualized compound (I) | Chloridazon |
| B-348 | one individualized compound (I) | Clopyralid |
| B-349 | one individualized compound (I) | Fluroxypyr |
| B-350 | one individualized compound (I) | Picloram |
| B-351 | one individualized compound (I) | Picolinafen |
| B-352 | one individualized compound (I) | Bensulfuron |
| B-353 | one individualized compound (I) | Chlorimuron-ethyl |
| B-354 | one individualized compound (I) | Cyclosulfamuron |
| B-355 | one individualized compound (I) | Iodosulfuron |
| B-356 | one individualized compound (I) | Mesosulfuron |
| B-357 | one individualized compound (I) | Metsulfuron-methyl |
| B-358 | one individualized compound (I) | Nicosulfuron |
| B-359 | one individualized compound (I) | Rimsulfuron |

TABLE B-continued

Composition comprising one indiviualized compound (I) and one further active substance from groups A) bis F)

| Mixture | Component 1 | Component 2 |
|---|---|---|
| B-360 | one individualized compound (I) | Triflusulfuron |
| B-361 | one individualized compound (I) | Atrazine |
| B-362 | one individualized compound (I) | Hexazinone |
| B-363 | one individualized compound (I) | Diuron |
| B-364 | one individualized compound (I) | Florasulam |
| B-365 | one individualized compound (I) | Pyroxasulfone |
| B-366 | one individualized compound (I) | Bentazone |
| B-367 | one individualized compound (I) | Cinidon-ethlyl |
| B-368 | one individualized compound (I) | Cinmethylin |
| B-369 | one individualized compound (I) | Dicamba |
| B-370 | one individualized compound (I) | Diflufenzopyr |
| B-371 | one individualized compound (I) | Quinclorac |
| B-372 | one individualized compound (I) | Quinmerac |
| B-373 | one individualized compound (I) | Mesotrione |
| B-374 | one individualized compound (I) | Saflufenacil |
| B-375 | one individualized compound (I) | Topramezone |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48, 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The mixtures of active substances can be prepared as compositions comprising besides the active ingridients at least one inert ingredient by usual means, e.g. by the means given for the compositions of compounds (I). Concerning usual ingredients of such compositions reference is made to the explanations given for the compositions containing compounds (I).

The mixtures of active substances according to the present invention are suitable as fungicides, as are the compounds (I). They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds (I), respectively.

SYNTHESIS EXAMPLES

With due modification of the starting compounds, the procedures shown in the synthesis examples below were used to obtain further compounds (I). The resulting compounds (I), together with physical data, are listed in Table I below.

I. Preparation of Intermediates

I.1 Preparation of aminomethylpyridine compounds (II)

Example 1

Preparation of 4-(aminomethyl)-2,3-dimethylpyridine

To a solution of $NaBH_4$ (65 g, 0.28 mol) in THF (150 ml) was added dropwise $BF_3$-diethyletherate (119.2 g, 0.84 mol) at 0° C. The reaction mixture was stirred for 20 minutes at 23° C. before adding dropwise a solution of 4-cyano-2,3-dimethylpyridine (18.5 g, 0.14 mol, prepared according to J. Heterocycl. Chem. 27 (6), 1990, 1751) in THF (100 ml). The resulting reaction mixture was refluxed for 6 h. Subsequently the reaction mixture was slowly hydrolyzed with water (200 ml) and the pH-value was adjusted to pH 2 with aqueous hydrochloric acid (10% strength). The resulting reaction mixture was refluxed for another 2 hours. Subsequently the reaction mixture was poured onto water and extracted with MTBE. The aqueous layer was adjusted to pH 14 with an aqueous sodium hydroxide solution (50% strength) and extracted once more with DCM. The combined organic layers were dried and the solvent was removed in vacuo. The residue was purified by column chromatography ($SiO_2$, MTBE) to yield 4-(aminomethyl)-2,3-dimethylpyridine as an oily substance (16.5 g). $^1$H-NMR ($CDCl_3$): $\delta$=1.7 (s, 2H), 2.3 (s, 3H), 2.5 (s, 3H), 3.9 (s, 2H), 7.15 (d, 1H) and 8.3 ppm (d, 2H).

I.2 Preparation of Sulfonic Acid Derivatives (III)

Example 2

Preparation of 4-(4-trifluoromethylpyrimidin-2-oxy) benzenesulfonyl chloride a) Preparation of 2-phenoxy-4-trifluoromethylpyrimidine To a solution of 2-chloro-4-trifluoromethylpyrimidine (3.0 g, 0.016 mol) in DMF (30 ml) were successively added phenol (1.9 g, 20 mmol), potassium carbonate (3.3 g, 24 mmol) and Cu(I) (100 mg). The reaction mixture was stirred for 7 h at 90° C. The resulting reaction mixture was partitioned between MTBE and water. The aqueous layer was extracted with MTBE. The solvent was removed from the organic layers in vacuo. 2-Phenoxy-4-trifluoromethylpyrimidine was obtained as a yellowish solid (3.0 g). $^1$H-NMR (CDCl$_3$): δ=7.2-7.5 (m, 6H); 8.7 ppm (m, 1H).

b) Preparation of 4-(4-trifluoromethylpyrimidin-2-oxy)benzenesulfonyl chloride

To a solution of 2-phenoxy-4-trifluoromethylpyrimidine (3.0 g, 12.5 mmol, prepared under a) in dichloroethane (30 ml) was added a solution chlorosulfonic acid (10.2 g, 88 mmol) in DCM (20 ml). The reaction mixture was stirred 7 h at 50° C. Subsequently the reaction mixture was slowly quenched with water and extracted with MTBE. The organic layer was washed with water and dried and the solvent was removed in vacuo. The residue was suspended in n-pentane and stirred for 10 minutes. Filtration yielded 4-(4-trifluoromethylpyrimidin-2-oxy)benzenesulfonyl chloride as a brownish solid (1.5 g). $^1$H-NMR (CDCl$_3$): δ=7.5 (m, 3H), 8.17 (m, 2H), 8.9 ppm (m, 1H).

II. Preparation of pyridylmethyl-sulfonamides (I)

Example 3

Preparation of N-(2,3-dimethylpyridin-4-ylmethyl)-4-(5-trifluoromethylpyridin-2-oxy)benzenesulfonyl amide (3)

(3)

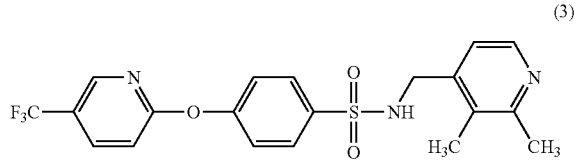

To a solution of 4-(aminomethyl)-2,3-dimethylpyridine (50 mg, 0.36 mmol, example I.1) in CH$_3$CN (150 ml) was added triethylamine (37.0 mg, 0.36 mmol). The reaction mixture was cooled to 0° C., 4-(5-trifluoromethylpyridin-2-oxy)benzenesulfonyl chloride (120 mg, 0.36 mmol, commercially available) was added and the reaction mixture was stirred 72 h at 23° C. Subsequently the solvent was removed in vacuo. The residue was dissolved in DCM, washed with water and dried. The solvent was removed in vacuo. The crude product was purified by column chromatography (SiO$_2$, MTBE/cyclohexane, 1:1) to yield the compound (3) (120 mg, HPLC-MS: 438.0 (M+H*)).

Example 4

Preparation of N-(pyridin-4-ylmethyl)-4-(4-trifluoromethylpyrimidin-2-oxy)benzenesulfonyl amide (4)

(4)

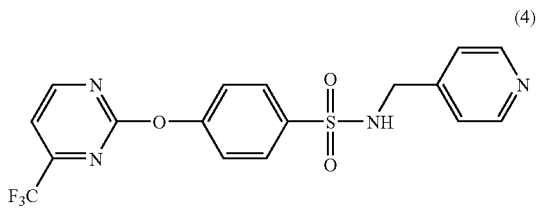

To a solution of 4-aminomethylpyridine (58 mg, 0.53 mmol) in CH$_3$CN (10 ml) was added triethylamine (55 mg, 0.53 mmol). The reaction mixture was cooled to 00° C. and 4-(4-trifluoromethylpyrimidin-2-oxy)benzenesulfonyl chloride (150 mg, 0.489 mmol, from example I.2) was added. The reaction mixture was stirred for 18 h at 23° C. The solvent was removed in vacuo. The residue was dissolved in DCM, washed once with water and dried. The solvent was removed in vacuo again to yield the title compound (4) (138 mg, HPLC: 410.8 (M+H*)).

The compounds (I) listed in Table I have been prepared in an analogous manner.

TABLE I (I)

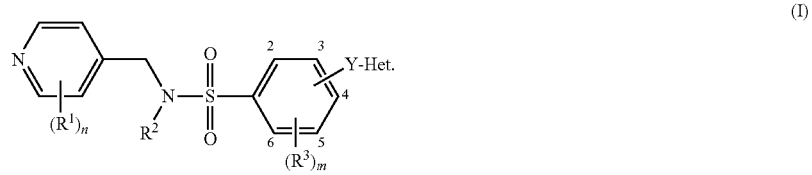

Compounds of formula

| ex. no | $(R^1)_n$ | $R^2$ | $(R^3)_m$ | Position Y-Het | Y | Het | m.p. [° C.]; HPLC R$_t$ [min], MS (M + H$^+$), $^1$H-NMR (CDCl$_3$, ppm) |
|---|---|---|---|---|---|---|---|
| 3 | 2-CH$_3$, 3-CH$_3$ | H | — | 4-Y-Het | —O— | 5-trifluoromethylpyridin-2-yl | 99-103° C. |
| 4 | — | H | — | 4-Y-Het | —O— | 4-trifluoromethylpyrimidin-2-yl | 2.32 min, 410.80 |
| 5 | —(CH)$_4$— | H | — | 4-Y-Het | —O— | pyridin-2-yl | 60-62° C. |
| 6 | —(CH)$_4$— | H | — | 4-Y-Het | —O— | 3-chloro-5-trifluoromethylpyridin-2-yl | 69-71° C. |
| 7 | 2-OCH$_3$ | H | — | 4-Y-Het | —O— | pyridin-2-yl | 108-110° C. |
| 8 | 3-OCH$_3$ | H | — | 4-Y-Het | —O— | pyridin-2-yl | 162° C. |
| 9 | — | H | — | 4-Y-Het | —O— | 5-trifluormethylpyridin-2-yl | 168.00-172.00 ° C. |
| 10 | — | H | — | 4-Y-Het | —O— | 3-trifluoromethylpyridin-2-yl | 2.42 min, 410.10 |
| 11 | — | H | — | 4-Y-Het | —O— | 3-chloro-5-trifluoromethylpyridin-2-yl | 2.68 min, 444.00 |
| 12 | 2-OCH$_3$ | H | — | 4-Y-Het | —O— | 5-trifluoromethylpyridin-2-yl | 119-122° C. |
| 13 | 2-OCH$_3$ | H | — | 4-Y-Het | —O— | 3-trifluoromethylpyridin-2-yl | 2.78 min, 440.10 |
| 14 | 2-OCH$_3$ | H | — | 4-Y-Het | —O— | 3-chloro-5-trifluoromethylpyridin-2-yl | 148-150° C. |

TABLE I-continued

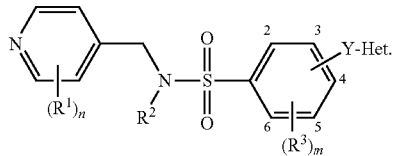

Compounds of formula (I)

| ex. no | $(R^1)_n$ | $R^2$ | $(R^3)_m$ | Position Y-Het | Y | Het | m.p. [° C.]; HPLC $R_t$ [min], MS (M + H$^+$), $^1$H-NMR (CDCl$_3$, ppm) |
|---|---|---|---|---|---|---|---|
| 15 | 3-OCH$_3$ | H | — | 4-Y-Het | —O— | 5-trifluoromethylpyridin-2-yl | 2.56 min, 440.10 |
| 16 | 3-OCH$_3$ | H | — | 4-Y-Het | —O— | 3-trifluoromethylpyridin-2-yl | 2.52 min, 440.10 |
| 17 | 3-OCH$_3$ | H | — | 4-Y-Het | —O— | 3-chloro-5-trifluoromethylpyridin-2-yl | 92-96° C. |
| 18 | 3-CH$_3$ | H | — | 4-Y-Het | —O— | 5-trifluoromethylpyridin-2-yl | 2.51 min, 420.10 |
| 19 | 3-CH$_3$ | H | — | 4-Y-Het | —O— | 3-trifluoromethylpyridin-2-yl | 2.47 min, 424.10 |
| 20 | 3-CH$_3$ | H | — | 4-Y-Het | —O— | 3-chloro-5-trifluoromethylpyridin-2-yl | 2.76 min, 458.00 |
| 21 | 2-OCH$_3$, 3-OCH$_3$ | H | — | 4-Y-Het | —O— | 5-trifluoromethylpyridin-2-yl | 3.47 min, 470.35 |
| 22 | 2-OCH$_3$, 3-OCH$_3$ | H | — | 4-Y-Het | —O— | 3-trifluoromethylpyridin-2-yl | 3.40 min, 470.35 |
| 23 | 2-OCH$_3$, 3-OCH$_3$ | H | — | 4-Y-Het | —O— | 3-chloro-5-trifluoromethylpyridin-2-yl | 3.73 min, 504.35 |
| 24 | 2-OCH$_3$, 5-OCH$_3$ | H | — | 4-Y-Het | —O— | 5-trifluoromethylpyridin-2-yl | 3.27 min, 470.10 |
| 25 | 2-OCH$_3$, 5-OCH$_3$ | H | — | 4-Y-Het | —O— | 3-trifluoromethylpyridin-2-yl | 3.1 min, 470.10 |
| 26 | 2-OCH$_3$, 5-OCH$_3$ | H | — | 4-Y-Het | —O— | 3-chloro-5-trifluoromethylpyridin-2-yl | 3.55 min, 504.00 |
| 27 | 2-CH$_3$, 3-CH$_3$ | H | — | 4-Y-Het | —O— | 3-chloro-5-trifluoromethylpyridin-2-yl | 134-136° C. |
| 28 | 2-CH$_3$, 3-CH$_3$ | H | — | 4-Y-Het | —O— | 3-trifluoromethylpyridin-2-yl | 128-132° C. |
| 29 | 2-Cl, 5-C$_2$H$_5$ | H | — | 4-Y-Het | —O— | 3-trifluoromethylpyridin-2-yl | 2.70 min, 438.00 |
| 30 | 2-Cl, 5-C$_2$H$_5$ | H | — | 4-Y-Het | —O— | 3-chloro-5-trifluoromethylpyridin-2-yl | 3.89 min, 505.90 |
| 31 | — | H | — | 4-Y-Het | —O— | pyridin-2-yl | 1.90 min, 341.90 |
| 32 | 3-CH$_3$ | H | — | 4-Y-Het | —O— | pyridin-2-yl | 3.07 min, 403.50 |
| 33 | 2-CH$_3$, 3-CH$_3$ | H | — | 4-Y-Het | —O— | pyridin-2-yl | 130-134° C. |
| 34 | — | H | — | 4-Y-Het | —O— | pyrimidin-2-yl | 1.51 min, 342.90 |
| 35 | 2-OCH$_3$ | H | — | 4-Y-Het | —O— | pyrimidin-2-yl | 1.83 min, 372.90 |
| 36 | 3-OCH$_3$ | H | — | 4-Y-Het | —O— | pyrimidin-2-yl | 1.76 min, 372.90 |
| 37 | 3-CH$_3$ | H | — | 4-Y-Het | —O— | pyrimidin-2-yl | 1.62 min, 356.90 |
| 38 | 2-CH$_3$, 3-CH$_3$ | H | — | 4-Y-Het | —O— | pyrimidin-2-yl | 1.68, 370.90 |
| 39 | — | H | — | 4-Y-Het | —O— | 4,6-dimethoxypyrimidin-2-yl | 2.15, 402.90 |
| 40 | 3-OCH$_3$ | H | — | 4-Y-Het | —O— | 4,6-dimethoxypyrimidin-2-yl | 2.27, 432.90 |
| 41 | 3-CH$_3$ | H | — | 4-Y-Het | —O— | 4,6-dimethoxypyrimidin-2-yl | 2.25, 416.90 |
| 42 | 2-CH$_3$, 3-CH$_3$ | H | — | 4-Y-Het | —O— | 4,6-dimethoxypyrimidin-2-yl | 2.30, 430,90 |
| 43 | 2-OCH$_3$ | H | — | 4-Y-Het | —O— | 4,6-dimethoxypyrimidin-2-yl | 2.55, 432.90 |
| 44 | — | H | — | 4-Y-Het | —O— | 6-methylpyridin-2-yl | 2.00, 356.35 |
| 45 | 2-OCH$_3$ | H | — | 4-Y-Het | —O— | 6-methylpyridin-2-yl | 2.32, 385.90 |
| 46 | 3-OCH$_3$ | H | — | 4-Y-Het | —O— | 6-methylpyridin-2-yl | 2.09, 385.90 |
| 47 | 2-CH$_3$, 3-CH$_3$ | H | — | 4-Y-Het | —O— | 6-methylpyridin-2-yl | 2.13, 384.35 |
| 48 | — | H | — | 4-Y-Het | —O— | 4,6-dimethylpyrimidin-2-yl | 1.87, 371.35 |
| 49 | 2-OCH$_3$ | H | — | 4-Y-Het | —O— | 4,6-dimethylpyrimidin-2-yl | 2.2, 401.35 |
| 50 | 3-OCH$_3$ | H | — | 4-Y-Het | —O— | 4,6-dimethylpyrimidin-2-yl | 2.00, 401.35 |
| 51 | 2-CH$_3$, 3-CH$_3$ | H | — | 4-Y-Het | —O— | 4,6-dimethylpyrimidin-2-yl | 2.02, 399.35 |
| 52 | 2-OCH$_3$ | H | — | 4-Y-Het | —O— | 5-methoxypyridazin-3-yl | 2.01, 402.90 |
| 53 | 2-CH$_3$, 3-CH$_3$ | H | — | 4-Y-Het | —O— | 5-methoxypyridazin-3-yl | 1.86, 400.90 |
| 54 | — | H | — | 4-Y-Het | —O— | 6-methylpyridazin-3-yl | 1.55, 357.00 |
| 55 | 2-OCH$_3$ | H | — | 4-Y-Het | —O— | 6-methylpyridazin-3-yl | 1.83, 386.90 |
| 56 | 3-OCH$_3$ | H | — | 4-Y-Het | —O— | 6-methylpyridazin-3-yl | 1.66, 386.90 |
| 57 | 2-CH$_3$, 3-CH$_3$ | H | — | 4-Y-Het | —O— | 6-methylpyridazin-3-yl | 1.69, 385.00 |
| 58 | — | H | — | 4-Y-Het | —O— | 6-methoxypyridazin-3-yl | 1.60, 372.90 |
| 59 | 2-OCH$_3$ | H | — | 4-Y-Het | —O— | 6-methoxypyridazin-3-yl | 1.91, 402.90 |
| 60 | 3-OCH$_3$ | H | — | 4-Y-Het | —O— | 6-methoxypyridazin-3-yl | 1.71, 402.90 |
| 61 | 2-CH$_3$, 3-CH$_3$ | H | — | 4-Y-Het | —O— | 6-methoxypyridazin-3-yl | 1.74, 400.90 |
| 62 | — | H | — | 4-Y-Het | —O— | 4-trifluoromethylpyrimidin-2-yl | 2.32, 410.80 |
| 63 | 2-OCH$_3$ | H | — | 4-Y-Het | —O— | 4-trifluoromethylpyrimidin-2-yl | 2.52, 440.80 |
| 64 | 3-OCH$_3$ | H | — | 4-Y-Het | —O— | 4-trifluoromethylpyrimidin-2-yl | 2.41, 440.90 |
| 65 | 2-CH$_3$, 3-CH$_3$ | H | — | 4-Y-Het | —O— | 4-trifluoromethylpyrimidin-2-yl | 2.43, 438.90 |
| 66 | — | H | — | 4-Y-Het | —O— | 4-methoxypyrimidin-2-yl | 2.01, 372.90 |
| 67 | 2-OCH$_3$ | H | — | 4-Y-Het | —O— | 4-methoxypyrimidin-2-yl | 2.26, 402.90 |
| 68 | 3-OCH$_3$ | H | — | 4-Y-Het | —O— | 4-methoxypyrimidin-2-yl | 2.00, 402.90 |
| 69 | 2-CH$_3$, 3-CH$_3$ | H | — | 4-Y-Het | —O— | 4-methoxypyrimidin-2-yl | 2.02, 400.90 |
| 70 | 2-OCH$_3$ | H | — | 4-Y-Het | —O— | 5-bromopyridin-2-yl | 2.90, 451.90 |
| 71 | 2-CH$_3$, 3-CH$_3$ | H | — | 4-Y-Het | —O— | 5-bromopyridin-2-yl | 2.57, 450.00 |
| 72 | —(CH)$_4$— | H | — | 4-Y-Het | —O— | 5-bromopyridin-2-yl | 2.69 min, 472.15 |
| 73 | 2-CH$_3$, 3-CH$_3$ | H | — | 4-Y-Het | —O— | 5-chloropyridin-2-yl | 2.44, 404.05 |
| 74 | 2-OCH$_3$ | H | — | 4-Y-Het | —O— | 5-chloropyridin-2-yl | 2.82, 406.00 |
| 75 | —(CH)$_4$— | H | — | 4-Y-Het | —O— | 5-chloropyridin-2-yl | Oil |
| 76 | —(CH)$_4$— | H | — | 4-Y-Het | —O— | 3-trifluoromethylpyridin-2-yl | 2.7 min, 460.25 |
| 77 | 2-CH$_3$, 3-CH$_3$ | H | — | 4-Y-Het | —O— | 3,5-dichloropyridin-2-yl | 96-100° C. |

TABLE I-continued

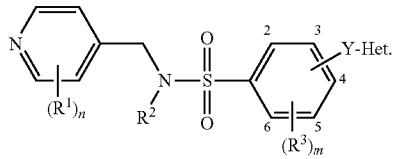

Compounds of formula (I)

| ex. no | (R¹)ₙ | R² | (R³)ₘ | Position Y-Het | Y | Het | m.p. [° C.]; HPLC Rₜ [min], MS (M + H⁺), ¹H-NMR (CDCl₃, ppm) |
|---|---|---|---|---|---|---|---|
| 78 | 2-OCH₃ | H | — | 4-Y-Het | —O— | 3,5-dichloropyridin-2-yl | 124-126° C. |
| 79 | —(CH)₄— | H | — | 4-Y-Het | —O— | 3,5-dichloropyridin-2-yl | 2.7 min, 460.15 |
| 80 | —(CH)₄— | H | — | 4-Y-Het | —O— | 5-trifluoromethylpyridin-2-yl | Oil |
| 81 | 2-OCH₃ | H | — | 4-Y-Het | —O— | 1-methyl-5-trifluoromethyl-1H-pyrazol-3-yl | 2.96 min, 442.9 |
| 82 | 3-OCH₃ | H | — | 4-Y-Het | —O— | 1-methyl-5-trifluoromethyl-1H-pyrazol-3-yl | 2.63 min, 442.8 |
| 83 | 2-CH₃, 3-CH₃ | H | — | 4-Y-Het | —O— | 1-methyl-5-trifluoromethyl-1H-pyrazol-3-yl | 2.6 min, 440.9 |
| 84 | 2-Cl, 3-OCH₃ | H | — | 4-Y-Het | —O— | 3-chloro-5-trifluoromethylpyridin-2-yl | 3.7 min, 509 |
| 85 | 2-Cl, 3-OCH₃ | H | — | 4-Y-Het | —O— | 5-trifluoromethylpyridin-2-yl | 3.4 min, 474 |
| 86 | 2-OCH₃ | H | — | 3-Y-Het | —O— | 3-chloro-5-trifluoromethylpyridin-2-yl | 3.2 min, 473.6 |
| 87 | 2-CH₃, 3-CH₃ | H | — | 3-Y-Het | —O— | 3-chloro-5-trifluoromethylpyridin-2-yl | 2.8 min, 471.6 |
| 88 | 2-OCH₃ | H | 2-F | 4-Y-Het | —O— | 3-chloro-5-trifluoromethylpyridin-2-yl | 3.3 min, 492 |
| 89 | 2-CH₃, 3-CH₃ | H | 2-F | 4-Y-Het | —O— | 3-chloro-5-trifluoromethylpyridin-2-yl | 2.9 min, 490 |
| 90 | 2-OCH₃ | H | 3-F | 4-Y-Het | —O— | 3-chloro-5-trifluoromethylpyridin-2-yl | 3.4 min, 492 |
| 91 | 2-CH₃, 3-CH₃ | H | 3-F | 4-Y-Het | —O— | 3-chloro-5-trifluoromethylpyridin-2-yl | 2.9 min, 490 |
| 92 | 2-OCH₃ | H | — | 4-Y-Het | —O— | 3-fluoro-5-chloropyridin-2-yl | 2.8 min, 424 |
| 93 | 2-CH₃, 3-CH₃ | H | — | 4-Y-Het | —O— | 3-fluoro-5-chloropyridin-2-yl | 2.5 min, 422 |
| 94 | 2-OCH₃ | H | 3-Cl | 4-Y-Het | —O— | 3-chloro-5-trifluoromethylpyridin-2-yl | 3.5 min, 508.6 |
| 95 | 2-CH₃, 3-CH₃ | H | 3-Cl | 4-Y-Het | —O— | 3-chloro-5-trifluoromethylpyridin-2-yl | 3.0 min, 505.6 |
| 96 | 2-OCH₃ | H | — | 4-Y-Het | —O— | 5-dichloromethylpyridin-2-yl | 147-149° C. |
| 97 | 2-CH₃, 3-CH₃ | H | — | 4-Y-Het | —O— | 3-bromo-5-chloropyridin-2-yl | 2.7 min, 483.5 |
| 98 | 2-OCH₃ | H | — | 4-Y-Het | —O— | 3-bromo-5-chloropyridin-2-yl | 3.1 min, 485.5 |
| 99 | 2-OCH₃ | H | — | 4-Y-Het | —O— | 3-methyl-5-chloropyridin-2-yl | 2.9 min, 419.7 |
| 100 | 2-CH₃, 3-CH₃ | H | — | 4-Y-Het | —O— | 3-methyl-5-chloropyridin-2-yl | 2.6 min, 417.7 |
| 101 | 2-OCH₃ | H | — | 4-Y-Het | —O— | 5-difluoromethoxypyridin-2-yl | 2.6 min, 437.1 |
| 102 | 2-CH₃, 3-CH₃ | H | — | 4-Y-Het | —O— | 5-difluoromethoxypyridin-2-yl | 2.4 min, 436.1 |
| 103 | 2-CH₃ | H | — | 4-Y-Het | —O— | 3-chloro-5-trifluoromethylpyridin-2-yl | 2.8 min, 458 |
| 104 | 2-CH₃ | H | — | 4-Y-Het | —O— | 5-trifluoromethylpyridin-2-yl | 2.5 min, 424 |
| 105 | 2-CH₃ | H | — | 4-Y-Het | —O— | 3,5-dichloropyridin-2-yl | 2.6 min, 423.9 |
| 106 | 2-OCH₃ | H | — | 4-Y-Het | —O— | 5-(1-methoxyimino)ethylpyridin-2-yl | 2.9 min, 443.2 |
| 107 | 2-CH₃, 3-CH₃ | H | — | 4-Y-Het | —O— | 5-(1-methoxyimino)ethylpyridin-2-yl | 2.6 min, 441.2 |
| 108 | 2-CF₃ | H | — | 4-Y-Het | —O— | 5-trifluoromethylpyridin-2-yl | 3.5 min, 477.6 |
| 109 | 2-CF₃ | H | — | 4-Y-Het | —O— | 3-chloro-5-trifluoromethylpyridin-2-yl | 3.8 min, 511.8 |
| 110 | 2-CF₃ | H | — | 4-Y-Het | —O— | 3,5-dichloropyridin-2-yl | 3.7 min, 479.5 |
| 111 | 2-CF₃ | H | — | 4-Y-Het | —O— | 3-methyl-5-trifluoromethylpyridin-2-yl | 3.7 min, 491.6 |
| 112 | 2-OCH₃ | H | — | 4-Y-Het | —O— | 5-trifluoromethylthiazol-2-yl | 3.2 min, 446.1 |
| 113 | 2-CH₃, 3-CH₃ | H | — | 4-Y-Het | —O— | 3-chloro-5-methoxypyridin-2-yl | 2.6 min, 434.2 |
| 114 | 2-CN | H | — | 4-Y-Het | —O— | 5-trifluoromethylpyridin-2-yl | 3.3 min, 435 |
| 115 | 2-CN | H | — | 4-Y-Het | —O— | 3,5-dichloropyridin-2-yl | 115-117° C. |
| 116 | 2-CN | H | — | 4-Y-Het | —O— | 5-chloropyridin-2-yl | 93-94° C. |
| 117 | 2-Cl | H | — | 4-Y-Het | —O— | 5-trifluoromethylpyridin-2-yl | 108-111° C. |
| 118 | 2-CN | H | — | 4-Y-Het | —O— | 3-chloro-5-trifluoromethylpyridin-2-yl | 154-157° C. |
| 119 | 2-C≡CH | CH₃ | — | 4-Y-Het | —O— | 3-chloro-5-trifluoromethylpyridin-2-yl | 3.6 min, 482.1 |
| 120 | 2-Cl | H | — | 4-Y-Het | —O— | 3-chloro-5-trifluoromethylpyridin-2-yl | 3.7 min, 478.1 |
| 121 | 2-C≡CH | CH₃ | — | 4-Y-Het | —O— | 5-trifluoromethylpyridin-2-yl | 3.2 min, 447.7 |
| 122 | 2-CN | H | — | 4-Y-Het | —O— | 5-chloropyridin-2-yl | 159-160.5° C. |
| 123 | 2-C₂H₅, 3-CH₃ | H | — | 4-Y-Het | —O— | 3-chloro-5-trifluoromethylpyridin-2-yl | 2.9 min, 485.6 |
| 124 | 2-CH₃, 3-CH₃ | H | 2-F | 4-Y-Het | —O— | 5-trifluoromethylpyridin-2-yl | 2.6 min, 456 |
| 125 | 2-OCH₃ | H | 2-CH₃, 5-CH₃ | 4-Y-Het | —O— | 3-chloro-5-trifluoromethylpyridin-2-yl | 3.5 min, 501.6 |
| 126 | 2-CH₃, 3-CH₃ | H | 2-CH₃, 5-CH₃ | 4-Y-Het | —O— | 3-chloro-5-trifluoromethylpyridin-2-yl | 3.1 min, 499.6 |
| 127 | 2-OCH₃ | H | 2-CH₃, 5-CH₃ | 4-Y-Het | —O— | 5-trifluoromethylpyridin-2-yl | 3.2 min, 468 |
| 128 | 2-CH₃, 3-CH₃ | H | 2-CH₃, 5-CH₃ | 4-Y-Het | —O— | 5-trifluoromethylpyridin-2-yl | 2.8 min, 466 |
| 129 | 2-OCH₃ | H | 3-CH₃, 5-CH₃ | 4-Y-Het | —O— | 3-chloro-5-trifluoromethylpyridin-2-yl | 3.5 min, 501.6 |
| 130 | 2-CH₃, 3-CH₃ | H | 3-CH₃, 5-CH₃ | 4-Y-Het | —O— | 3-chloro-5-trifluoromethylpyridin-2-yl | 3.0 min, 499.6 |
| 131 | 2-OCH₃ | H | 3-CH₃, 5-CH₃ | 4-Y-Het | —O— | 5-trifluoromethylpyridin-2-yl | 3.2 min, 467.7 |
| 132 | 2-CH₃, 3-CH₃ | H | 3-CH₃, 5-CH₃ | 4-Y-Het | —O— | 5-trifluoromethylpyridin-2-yl | 218-222° C. |
| 133 | 2-OCH₃ | H | 2-CH₃, 3-CH₃ | 4-Y-Het | —O— | 5-trifluoromethylpyridin-2-yl | 3.5 min, 502 |
| 134 | 2-CH₃, 3-CH₃ | H | 2-CH₃, 3-CH₃ | 4-Y-Het | —O— | 3-chloro-5-trifluoromethylpyridin-2-yl | 3.1 min, 500 |
| 135 | 2-OCH₃ | H | 2-CH₃, 3-CH₃ | 4-Y-Het | —O— | 5-trifluoromethylpyridin-2-yl | 3.2 min, 468 |
| 136 | 2-CH₃, 3-CH₃ | H | 2-CH₃, 3-CH₃ | 4-Y-Het | —O— | 5-trifluoromethylpyridin-2-yl | 2.8 min, 466 |
| 137 | 2-CH₃, 3-CH₃ | H | — | 4-Y-Het | —O— | 3-trifluoromethylpyridin-2-yl | 128-132° C. |

TABLE I-continued

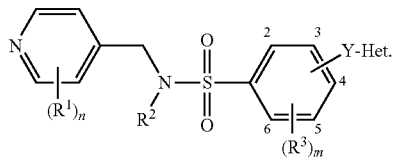

Compounds of formula

| ex. no | (R¹)ₙ | R² | (R³)ₘ | Position Y-Het | Y | Het | m.p. [°C.]; HPLC Rₜ [min], MS (M + H⁺), ¹H-NMR (CDCl₃, ppm) |
|---|---|---|---|---|---|---|---|
| 138 | 2-OCH₃ | H | — | 4-Y-Het | —O— | 3-trifluoromethyl-5-chloro-pyridin-2-yl | 131-134° C. |
| 139 | 2-CH₃, 3-CH₃ | H | — | 4-Y-Het | —O— | 3-trifluoromethyl-5-chloro-pyridin-2-yl | 2,85 min, 472,05 |
| 140 | — | H | — | 4-Y-Het | —O— | 5-trifluoromethyl-6-chloro-pyridin-2-yl | 143-146° C. |
| 141 | 2-OCH₃ | H | — | 4-Y-Het | —O— | 5-trifluoromethyl-6-chloro-pyridin-2-yl | 118-121° C. |
| 142 | 3-OCH₃ | H | — | 4-Y-Het | —O— | 5-trifluoromethyl-6-chloro-pyridin-2-yl | 2.80 min, 474.00 |
| 143 | 2-CH₃, 3-CH₃ | H | — | 4-Y-Het | —O— | 5-trifluoromethyl-6-chloro-pyridin-2-yl | 2.81 min, 472.00 |
| 144 | — | H | — | 4-Y-Het | —O— | 3,6-dichloro-4-trifluoromethylpyridin-2-yl | 2.89 min, 477.95 |
| 145 | 2-OCH₃ | H | — | 4-Y-Het | —O— | 3,6-dichloro-4-trifluoromethylpyridin-2-yl | 3.48 min, 507.95 |
| 146 | 3-OCH₃ | H | — | 4-Y-Het | —O— | 3,6-dichloro-4-trifluoromethylpyridin-2-yl | 3.01 min, 507.95 |
| 147 | 2-CH₃, 3-CH₃ | H | — | 4-Y-Het | —O— | 3,6-dichloro-4-trifluoromethylpyridin-2-yl | 3.01 min, 506.05 |
| 148 | — | H | — | 4-Y-Het | —O— | 5-nitropyridin-2-yl | 2.19 min, 386.80 |
| 149 | 2-OCH₃ | H | — | 4-Y-Het | —O— | 5-nitropyridin-2-yl | 2.62 min, 416.80 |
| 150 | 3-OCH₃ | H | — | 4-Y-Het | —O— | 5-nitropyridin-2-yl | 2.33 min, 416.80 |
| 151 | 2-CH₃, 3-CH₃ | H | — | 4-Y-Het | —O— | 5-nitropyridin-2-yl | 2.33 min, 414.90 |
| 152 | — | H | — | 4-Y-Het | —O— | 5-methansulfonylpyridin-2-yl | 1.80 min, 420.05 |
| 153 | 2-OCH₃ | H | — | 4-Y-Het | —O— | 5-methansulfonylpyridin-2-yl | 2.27 min, 450.05 |
| 154 | 3-OCH₃ | H | — | 4-Y-Het | —O— | 5-methansulfonylpyridin-2-yl | 2.1 min, 450.05 |
| 155 | 2-CH₃, 3-CH₃ | H | — | 4-Y-Het | —O— | 5-methansulfonylpyridin-2-yl | 1.90 min, 448.05 |
| 156 | 2-CH₃, 3-CH₃ | H | — | 4-Y-Het | —O— | 3-chloro-pyridin-2-yl | Oil |
| 157 | 2-CH₃, 3-CH₃ | H | — | 4-Y-Het | —O— | 6-trifluoromethylpyridin-2-yl | Oil |
| 158 | 2-CH₃, 3-CH₃ | H | — | 4-Y-Het | —O— | 3-fluoro-5-trifluoromethylpyridin-2-yl | 2.74 min, 456.05 |
| 159 | — | H | — | 4-Y-Het | —O— | 3-methyl-5-trifluoromethylpyridin-2-yl | 42-44° C. |
| 160 | 2-OCH₃ | H | — | 4-Y-Het | —O— | 3-methyl-5-trifluoromethylpyridin-2-yl | 106-109° C. |
| 161 | 3-OCH₃ | H | — | 4-Y-Het | —O— | 3-methyl-5-trifluoromethylpyridin-2-yl | 2.80 min, 454.00 |
| 162 | 2-CH₃, 3-CH₃ | H | — | 4-Y-Het | —O— | 3-methyl-5-trifluoromethylpyridin-2-yl | 53-66° C. |
| 163 | 2-OCH₃ | H | — | 4-Y-Het | —O— | 4-methyl-5-trifluoromethylpyridin-2-yl | 147-152° C. |
| 164 | 2-CH₃, 3-CH₃ | H | — | 4-Y-Het | —O— | 4-methyl-5-trifluoromethylpyridin-2-yl | 2.88 min, 451.90 |
| 165 | 2-OCH₃ | H | — | 4-Y-Het | —O— | 3-chloropyridin-2-yl | Oil |
| 166 | 2-CH₃, 3-CH₃ | H | — | 4-Y-Het | —O— | 3,5-difluoropyridin-2-yl | Oil |
| 167 | 2-OCH₃ | H | — | 4-Y-Het | —O— | 3,5-difluoropyridin-2-yl | 97-100° C. |
| 168 | — | H | — | 4-Y-Het | —O— | 4,5-dimethyl-2-trifluoromethylpyrimidin-4-yl | 2.4 min, 439.00 |
| 169 | 2-OCH₃ | H | — | 4-Y-Het | —O— | 4,5-dimethyl-2-trifluoromethyl-pyrimidin-4-yl | 2.93 min, 469.00 |
| 170 | 3-OCH₃ | H | — | 4-Y-Het | —O— | 4,5-dimethyl-2-trifluoromethyl-pyrimidin-4-yl | 2.62 min, 469.00 |
| 171 | 2-CH₃, 3-CH₃ | H | — | 4-Y-Het | —O— | 4,5-dimethyl-2-trifluoromethyl-pyrimidin-4-yl | 2.61 min, 467.10 |
| 172 | — | H | — | 4-Y-Het | —O— | 2-trifluoromethylpyrimidin-4-yl | 2.28, 410.90 |
| 173 | 2-OCH₃ | H | — | 4-Y-Het | —O— | 2-trifluoromethylpyrimidin-4-yl | Oil |
| 174 | 3-OCH₃ | H | — | 4-Y-Het | —O— | 2-trifluoromethylpyrimidin-4-yl | 2.39 min, 440.90 |
| 175 | 2-CH₃, 3-CH₃ | H | — | 4-Y-Het | —O— | 2-trifluoromethylpyrimidin-4-yl | 2.42 min, 438.90 |
| 176 | — | H | — | 4-Y-Het | —O— | 6-methyl-4-trifluoromethylpyridin-2-yl | 151-155° C. |
| 177 | 2-OCH₃ | H | — | 4-Y-Het | —O— | 6-methyl-4-trifluoromethylpyridin-2-yl | 3.21 min, 454.05 |
| 178 | 3-OCH₃ | H | — | 4-Y-Het | —O— | 6-methyl-4-trifluoromethylpyridin-2-yl | 2.82 min, 454.05 |
| 179 | 2-CH₃, 3-CH₃ | H | — | 4-Y-Het | —O— | 6-methyl-4-trifluoromethylpyridin-2-yl | 2.81 min, 452.05 |
| 180 | — | H | 3-CH₃ | 4-Y-Het | —O— | 3-chloro-5-trifluoromethylpyridin-2-yl | 2.93 min, 457.80 |
| 181 | 2-OCH₃ | H | 3-CH₃ | 4-Y-Het | —O— | 3-chloro-5-trifluoromethylpyridin-2-yl | 146-149° C. |
| 182 | 3-OCH₃ | H | 3-CH₃ | 4-Y-Het | —O— | 3-chloro-5-trifluoromethylpyridin-2-yl | 3.04 min, 487.80 |
| 183 | 2-CH₃, 3-CH₃ | H | 3-CH₃ | 4-Y-Het | —O— | 3-chloro-5-trifluoromethylpyridin-2-yl | 170-173° C. |
| 184 | — | H | 2-CH₃ | 4-Y-Het | —O— | 3-chloro-5-trifluoromethylpyridin-2-yl | 2.94 min, 457.80 |
| 185 | 2-OCH₃ | H | 2-CH₃ | 4-Y-Het | —O— | 3-chloro-5-trifluoromethylpyridin-2-yl | 103-105° C. |
| 186 | 3-OCH₃ | H | 2-CH₃ | 4-Y-Het | —O— | 3-chloro-5-trifluoromethylpyridin-2-yl | 133-139° C. |
| 187 | 2-CH₃, 3-CH₃ | H | 2-CH₃ | 4-Y-Het | —O— | 3-chloro-5-trifluoromethylpyridin-2-yl | 109-112° C. |
| 188 | — | H | 3-CH₃ | 4-Y-Het | —O— | 3-trifluoromethylpyridin-2-yl | 146-154° C. |
| 189 | 2-OCH₃ | H | 3-CH₃ | 4-Y-Het | —O— | 3-trifluoromethylpyridin-2-yl | 139-146° C. |
| 190 | 3-OCH₃ | H | 3-CH₃ | 4-Y-Het | —O— | 3-trifluoromethylpyridin-2-yl | 2.73 min, 454.05 |
| 191 | 2-CH₃, 3-CH₃ | H | 3-CH₃ | 4-Y-Het | —O— | 3-trifluoromethylpyridin-2-yl | 2.73 min, 452.05 |
| 192 | — | H | 2-CH₃ | 4-Y-Het | —O— | 3-trifluoromethylpyridin-2-yl | 142-145° C. |

TABLE I-continued

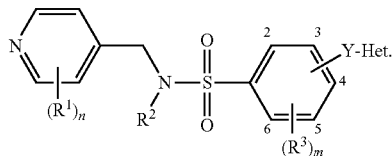

Compounds of formula

| ex. no | $(R^1)_n$ | $R^2$ | $(R^3)_m$ | Position Y-Het | Y | Het | m.p. [°C.]; HPLC $R_t$ [min], MS (M + H$^+$), $^1$H-NMR (CDCl$_3$, ppm) |
|---|---|---|---|---|---|---|---|
| 193 | 2-OCH$_3$ | H | 2-CH$_3$ | 4-Y-Het | —O— | 3-trifluoromethylpyridin-2-yl | 3.05 min, 454.05 |
| 194 | 3-OCH$_3$ | H | 2-CH$_3$ | 4-Y-Het | —O— | 3-trifluoromethylpyridin-2-yl | 2.56 min, 454.05 |
| 195 | 2-CH$_3$, 3-CH$_3$ | H | 2-CH$_3$ | 4-Y-Het | —O— | 3-trifluoromethylpyridin-2-yl | 2.67 min, 452.10 |
| 196 | — | H | 3-CH$_3$ | 4-Y-Het | —O— | 5-trifluoromethylpyridin-2-yl | 2.62 min, 424.00 |
| 197 | 2-OCH$_3$ | H | 3-CH$_3$ | 4-Y-Het | —O— | 5-trifluoromethylpyridin-2-yl | 112-114° C. |
| 198 | 3-OCH$_3$ | H | 3-CH$_3$ | 4-Y-Het | —O— | 5-trifluoromethylpyridin-2-yl | 2.71 min, 454.00 |
| 199 | 2-CH$_3$, 3-CH$_3$ | H | 3-CH$_3$ | 4-Y-Het | —O— | 5-trifluoromethylpyridin-2-yl | 145-148° C. |
| 200 | — | H | 2-CH$_3$ | 4-Y-Het | —O— | 5-trifluoromethylpyridin-2-yl | 2.62 min, 424.05 |
| 201 | 2-OCH$_3$ | H | 2-CH$_3$ | 4-Y-Het | —O— | 5-trifluoromethylpyridin-2-yl | 102-104° C. |
| 202 | 3-OCH$_3$ | H | 2-CH$_3$ | 4-Y-Het | —O— | 5-trifluoromethylpyridin-2-yl | 2.72 min, 454.05 |
| 203 | 2-CH$_3$, 3-CH$_3$ | H | 2-CH$_3$ | 4-Y-Het | —O— | 5-trifluoromethylpyridin-2-yl | 98-101° C. |
| 204 | — | H | — | 4-Y-Het | —O— | 3-chloro-4-methyl-5-trifluoromethylpyridin-2-yl | 2.92 min, 458.00 |
| 205 | 2-OCH$_3$ | H | — | 4-Y-Het | —O— | 3-chloro-4-methyl-5-trifluoromethylpyridin-2-yl | 3.36 min, 488.00 |
| 206 | 3-OCH$_3$ | H | — | 4-Y-Het | —O— | 3-chloro-4-methyl-5-trifluoromethylpyridin-2-yl | 3.03 min, 488.00 |
| 207 | 2-CH$_3$, 3-CH$_3$ | H | — | 4-Y-Het | —O— | 3-chloro-4-methyl-5-trifluoromethylpyridin-2-yl | 3.03 min, 486.00 |
| 208 | — | H | — | 4-Y-Het | —O— | 4-methyl-5-trifluoromethylpyridin-2-yl | 101-105° C. |
| 209 | 3-OCH$_3$ | H | — | 4-Y-Het | —O— | 4-methyl-5-trifluoromethylpyridin-2-yl | 106-111° C. |
| 210 | 2-Cl | H | — | 4-Y-Het | —O— | 3,5-dichloropyridin-2-yl | 95-98° C. |
| 211 | 2-CH$_3$, 3-CH$_3$ | H | 2-F | 4-Y-Het | —O— | 3-chloro-5-trifluoromethylpyridin-2-yl | Oil |
| 212 | 2-CH$_3$, 3-CH$_3$ | CH$_3$ | — | 4-Y-Het | —O— | 5-trifluoromethylpyridin-2-yl | 2.6 min, 451.70 |
| 213 | 2-CH$_3$, 3-CH$_3$ | ethyl | — | 4-Y-Het | —O— | 5-trifluoromethylpyridin-2-yl | 2.87 min, 465.70 |
| 214 | 2-CH$_3$, 3-CH$_3$ | CH$_3$ | 3-CH$_3$ | 4-Y-Het | —O— | 5-trifluoromethylpyridin-2-yl | 2.95 min, 465.70 |
| 215 | 2-CH$_3$, 3-CH$_3$ | ethyl | 3-CH$_3$ | 4-Y-Het | —O— | 5-trifluoromethylpyridin-2-yl | 3.3 min, 479.70 |
| 216 | 2-OCH$_3$ | CH$_3$ | — | 4-Y-Het | —O— | 3-chloro-5-trifluoromethylpyridin-2-yl | 3.73 min, 488.05 |
| 217 | 2-OCH$_3$ | ethyl | — | 4-Y-Het | —O— | 3-chloro-5-trifluoromethylpyridin-2-yl | 3.83 min, 502.05 |
| 218 | 2-CH$_3$, 3-CH$_3$ | allyl | — | 4-Y-Het | —O— | 5-trifluoromethylpyridin-2-yl | 2.95 min, 477.70 |
| 219 | 2-CH$_3$, 3-CH$_3$ | allyl | 3-CH$_3$ | 4-Y-Het | —O— | 5-trifluoromethylpyridin-2-yl | 3.10 min, .491.70 |
| 220 | 2-OCH$_3$ | allyl | — | 4-Y-Het | —O— | 3-chloro-5-trifluoromethylpyridin-2-yl | 3.77 min, 513.60 |
| 221 | 2-CH$_3$, 3-CH$_3$ | CH$_3$ | 2-CH$_3$ | 4-Y-Het | —O— | 5-trifluoromethylpyridin-2-yl | 2.88 min, 465.70 |
| 222 | 2-CH$_3$, 3-CH$_3$ | allyl | 2-CH$_3$ | 4-Y-Het | —O— | 5-trifluoromethylpyridin-2-yl | 3.05 min, 491.70 |
| 223 | 2-CH$_3$, 3-CH$_3$ | CH$_3$ | 2-CH$_3$ | 4-Y-Het | —O— | 3-chloro-5-trifluoromethylpyridin-2-yl | 3.11 min, 499.60 |
| 224 | 2-CH$_3$, 3-CH$_3$ | ethyl | 2-CH$_3$ | 4-Y-Het | —O— | 3-chloro-5-trifluoromethylpyridin-2-yl | 3.20 min, 513.60 |
| 225 | 2-CH$_3$, 3-CH$_3$ | allyl | 2-CH$_3$ | 4-Y-Het | —O— | 3-chloro-5-trifluoromethylpyridin-2-yl | 3.28 min, 525. 60 |
| 226 | 2-OCH$_3$ | CH$_3$ | — | 4-Y-Het | —O— | 5-trifluoromethylpyridin-2-yl | 3.51 min, 454.00 |
| 227 | 2-OCH$_3$ | ethyl | — | 4-Y-Het | —O— | 5-trifluoromethylpyridin-2-yl | 3.61 min, 468.05 |
| 228 | 2-OCH$_3$ | allyl | — | 4-Y-Het | —O— | 5-trifluoromethylpyridin-2-yl | 3.72 min, 480.05 |
| 229 | 2-OCH$_3$ | H | 3-Cl | 4-Y-Het | —O— | 5-trifluoromethylpyridin-2-yl | 112-115° C. |
| 230 | 2-CH$_3$, 3-CH$_3$ | H | 3-Cl | 4-Y-Het | —O— | 5-trifluoromethylpyridin-2-yl | 162-165° C. |
| 231 | —(CH$_2$)$_3$— | H | — | 4-Y-Het | —O— | 3-chloro-5-trifluoromethylpyridin-2-yl | 3.19 min, 484.10 |
| 232 | 2-CH$_3$, 3-OCH$_3$ | H | — | 4-Y-Het | —O— | 5-trifluoromethylpyridin-2-yl | 2.68 min, 437.70 |
| 233 | 2-CH$_3$, 3-OCH$_3$ | H | — | 4-Y-Het | —O— | 3-chloro-5-trifluoromethylpyridin-2-yl | 169-172° C. |
| 234 | —(CH2)$_4$— | H | — | 4-Y-Het | —O— | 5-trifluoromethylpyridin-2-yl | 164-168° C. |
| 235 | —(CH$_2$)$_4$— | H | — | 4-Y-Het | —O— | 3-chloro-5-trifluoromethylpyridin-2-yl | 2.93 min, 497.60 |
| 236 | 2-OCH$_3$ | H | — | 4-Y-Het | —O— | 2-trifluoromethylpyridin-4-yl | 2.79 min, 440.15 |
| 237 | 2-CH$_3$, 3-CH$_3$ | H | — | 4-Y-Het | —O— | 2-trifluoromethylpyridin-4-yl | 2.37 min, 437.70 |
| 238 | 2-OCH$_3$ | H | — | 4-Y-Het | —O— | 1-methyl-3-trifluoromethyl-1H-pyrazol-5-yl | 2.78 min, 442.70 |
| 239 | 2-CH$_3$, 3-CH$_3$ | H | — | 4-Y-Het | —O— | 1-methyl-3-trifluoromethyl-1H-pyrazol-5-yl | 2.40 min, 440.70 |
| 240 | —(CH$_2$)$_3$— | H | — | 4-Y-Het | —O— | 5-trifluoromethylpyridin-2-yl | 161-164° C. |
| 241 | 2-OCH$_3$ | H | — | 4-Y-Het | —O— | 4-chloro-1-methyl-3-trifluoromethyl-1H-pyrazol-5-yl | 3.08 min, 476.60 |
| 242 | 2-CH$_3$, 3-CH$_3$ | H | — | 4-Y-Het | —O— | 4-chloro-1-methyl-3-trifluoromethyl-1H-pyrazol-5-yl | 149-152° C. |
| 243 | 2-OCH$_3$ | H | — | 4-Y-Het | —O— | 5-ethoxycarbonylpyridin-2-yl | 2.72 min, 443.70 |
| 244 | 2-CH$_3$, 3-CH$_3$ | H | — | 4-Y-Het | —O— | 5-ethoxycarbonylpyridin-2-yl | 2.44 min, 441.70 |
| 245 | 2-OCH$_3$ | H | — | 4-Y-Het | —O— | 3-trifluoromethylpyridin-4-yl | 2.41 min, 439.60 |
| 246 | 2-CH$_3$, 3-CH$_3$ | H | — | 4-Y-Het | —O— | 3-trifluoromethylpyridin-4-yi | 2.13 min, 437.70 |

TABLE I-continued

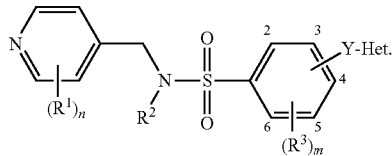

Compounds of formula (I)

| ex. no | (R¹)ₙ | R² | (R³)ₘ | Position Y-Het | Y | Het | m.p. [°C.]; HPLC R₁ [min], MS (M + H⁺), ¹H-NMR (CDCl₃, ppm) |
|---|---|---|---|---|---|---|---|
| 247 | 2-CH₃, 3-OCH₂CH₃ | H | — | 4-Y-Het | —O— | 5-trifluoromethylpyridin-2-yl | 2.72 min, 467.70 |
| 248 | 2-CH₃, 3-OCH₂CH₃ | H | — | 4-Y-Het | —O— | 3-chloro-5-trifluoromethylpyridin-2-yl | 2.97 min, 501.60 |
| 249 | 2-OCH₃ | H | — | 4-Y-Het | —O— | 6-trifluoromethylpyridazin-3-yl | 183-186° C. |
| 250 | 2-CH₃, 3-CH₃ | H | — | 4-Y-Het | —O— | 6-trifluoromethylpyridazin-3-yl | 171-174° C. |
| 251 | 2-OCH₃ | H | — | 4-Y-Het | —O— | isoquinolin-4-yl | 3,9 (s); 4,2 (d); 4,9 (m); 5,3 (s) |
| 252 | 2-CH₃, 3-CH₃ | H | — | 4-Y-Het | —O— | isoquinolin-4-yl | 2,15 (s); 2,4 (s); 4,2 d); 4,95 (m); 5,3 (s) |
| 253 | 2-OCH₃ | H | — | 4-Y-Het | —O— | 5-methylpyridin-2-yl | 2.48 min, 386.25 |
| 254 | 2-CH₃, 3-CH₃ | H | — | 4-Y-Het | —O— | 5-methylpyridin-2-yl | 2.24 min, 384.25 |
| 255 | 2-OCH₃ | H | — | 4-Y-Het | —O— | 2-methylpyridin-4-yl | 2,5 (s); 3,8 (s); 4,15 (m); 5,15 (m); 5,3 (s) |
| 256 | 2-CH₃, 3-CH₃ | H | — | 4-Y-Het | —O— | 2-methylpyridin-4-yl | 2,15 (s); 2,45 (s); 2,55 (s); 4,2 (m); 5,5 (s) |
| 257 | 2-OCH₃ | H | — | 4-Y-Het | —OCH₂— | 1-methyl-3-trifluoromethyl-1H-pyrazol-4-yl | 2.5 min, 456.70 |
| 258 | 2-CH₃, 3-CH₃ | H | — | 4-Y-Het | —OCH₂— | 1-methyl-3-trifluoromethyl-1H-pyrazol-4-yl | 2.31 min, 454.70 |
| 259 | 2-CH₃, 3-CH₂CH₃ | H | — | 4-Y-Het | —O— | 5-trifluoromethylpyridin-2-yl | 2.71 min, 452.25 |
| 260 | 2-CH₃, 3-CH₂CH₃ | H | — | 4-Y-Het | —O— | 3-chloro-5-trifluoromethylpyridin-2-yl | 2.92 min, 486.25 |
| 261 | 2-OCH₃ | H | — | 4-Y-Het | —OCH₂— | 4-trifluoromethylpyridin-2-yl | 137-141° C. |
| 262 | 2-CH₃, 3-CH₃ | H | — | 4-Y-Het | —OCH₂— | 4-trifluoromethylpyridin-2-yl | 159-162° C. |
| 263 | 2-OCH₃ | H | — | 4-Y-Het | —OCH₂— | 1-methyl-4-trifluoromethyl-thiazol-5-yl | 113-117° C. |
| 264 | 2-CH₃, 3-CH₃ | H | — | 4-Y-Het | —OCH₂— | 1-methyl-4-trifluoromethyl-thiazol-5-yl | 112-119° C. |
| 265 | 2-CH₃, 3-CH₃ | H | — | 4-Y-Het | —OCH₂— | 3-ethylisoxazol-5-yl | 141-144° C. |
| 266 | 2-OCH₃ | H | — | 4-Y-Het | —OCH₂— | 6-trifluoromethylpyridin-2-yl | 137-140° C. |
| 267 | 2-CH₃, 3-CH₃ | H | — | 4-Y-Het | —OCH₂— | 6-trifluoromethylpyridin-2-yl | 2.59-452.25 |
| 268 | 2-OCH₃ | H | — | 4-Y-Het | —OCH₂— | 3-ethylisoxazol-5-yl | 2.55 min, 404.25 |
| 269 | 2-OCH₃ | H | — | 4-Y-Het | —OCH₂— | 3-trifluoromethylpyridin-2-yl | 123-127° C. |
| 270 | 2-CH₃, 3-CH₃ | H | — | 4-Y-Het | —OCH₂— | 3-trifluoromethylpyridin-2-yl | 2.44 min, 452.25 |
| 271 | 2-OCH₃ | H | — | 4-Y-Het | —O— | 4-chloro-1-methyl-3-trifluoromethyl-1H-pyrazol-5-yl | 3.27 min, 477.15 |
| 272 | 2-CH₃, 3-CH₃ | H | — | 4-Y-Het | —O— | 4-chloro-1-methyl-3-trifluoromethyl-1H-pyrazol-5-yl | 2.86 min, 475.15 |
| 273 | 2-OCH₃ | H | — | 4-Y-Het | —OCH₂— | pyridin-4-yl | 125-130° C. |
| 274 | 2-CH₃, 3-CH₃ | H | — | 4-Y-Het | —OCH₂— | pyridin-4-yl | 2,15 (s); 2,4 (s); 3,95 (m); 5,2 (s); 8,6 (m) |
| 275 | 2-OCH₃ | H | — | 4-Y-Het | —OCH₂— | 2-chloro-thiazol-5-yl | 147-150° C. |
| 276 | 2-CH₃, 3-CH₃ | H | — | 4-Y-Het | —O— | 2-chloro-thiazol-5-yl | 153-156° C. |
| 277 | 2-OCH₃ | H | 3-CH₃ | 4-Y-Het | —O— | 5-chloro-pyridin-2-yl | 102-105° C. |
| 278 | 2-CH₃, 3-CH₃ | H | 3-CH₃ | 4-Y-Het | —O— | 5-chloro-pyridin-2-yl | 2.66 min, 417.70 |
| 279 | 2-OCH₃ | H | 2-CH₃ | 4-Y-Het | —O— | 5-chloro-pyridin-2-yl | 2.63 min, 417.70 |
| 280 | 2-CH₃, 3-CH₃ | H | 2-CH₃ | 4-Y-Het | —O— | 5-chloro-pyridin-2-yl | 3.03 min, 419.60 |
| 281 | 2-OCH₃ | H | 3-CH₃ | 4-Y-Het | —O— | 3,5-dichloro-pyridin-2-yl | 102° C. |
| 282 | 2-CH₃, 3-CH₃ | H | 3-CH₃ | 4-Y-Het | —O— | 3,5-dichloro-pyridin-2-yl | 172° C. |
| 283 | 2-OCH₃ | H | 2-CH₃ | 4-Y-Het | —O— | 3,5-dichloro-pyridin-2-yl | 104° C. |
| 284 | 2-CH₃, 3-CH₃ | H | 2-CH₃ | 4-Y-Het | —O— | 3,5-dichloro-pyridin-2-yl | 2.92 min, 453.60 |
| 285 | 2-OCH₃ | H | — | 4-Y-Het | —OCH₂— | 5-trifluoromethylpyridin-3-yl | 140-145° C. |
| 286 | 2-CH₃, 3-CH₃ | H | — | 4-Y-Het | —OCH₂— | 5-trifluoromethylpyridin-3-yl | 2.44 min, 451.70 |
| 287 | 2-OCH₃ | H | — | 4-Y-Het | —OCH₂— | 6-chloropyridin-3-yl | 2.67 min, 420.15 |
| 288 | 2-CH₃, 3-CH₃ | H | — | 4-Y-Het | —OCH₂— | 6-chloropyridin-3-yl | 165-167° C. |
| 289 | 2-CH₃, 3-Cl | H | — | 4-Y-Het | —O— | 3-chloro-5-trifluoromethylpyridin-2-yl | 138-141° C. |
| 290 | 2-OCH₃ | H | 2-F | 4-Y-Het | —O— | 5-trifluoromethylpyridin-2-yl | 128-132° C. |
| 291 | 2-OCH₃ | H | 3-F | 4-Y-Het | —O— | 5-trifluoromethylpyridin-2-yl | 101-104° C. |
| 292 | 2-CH₃, 3-CH₃ | H | — | 4-Y-Het | —O— | 3-chloro-5-difluoromethoxypyridin-2-yl | 2.72 min, 469.60 |
| 293 | 2-OCH₃ | H | — | 4-Y-Het | —OCH₂— | pyridin-2-yl | 121-125° C. |
| 294 | 2-CH₃, 3-CH₃ | H | — | 4-Y-Het | —OCH₂— | pyridin-2-yl | 154-156° C. |
| 295 | 2-OCH₃, 3-Cl | H | — | 4-Y-Het | —O— | 3-chloro-5-trifluoromethylpyridin-2-yl | 2.99 min, 474.15 |
| 296 | 2-OCH₃ | H | — | 4-Y-Het | —O— | 3-bromo-pyridin-4-yl | 2.29 min, 452.15 |
| 297 | 2-CH₃, 3-CH₃ | H | — | 4-Y-Het | —O— | 3-bromo-pyridin-4-yl | 2.03 min, 450.10 |
| 298 | 2-OCH₃ | H | — | 4-Y-Het | —O— | 3-chloro-pyridin-4-yl | 2.52 min, 406.15 |
| 299 | 2-OCH₃ | H | — | 4-Y-Het | —S— | 3-chloro-5-trifluoromethylpyridin-2-yl | 147-150° C. |

TABLE I-continued

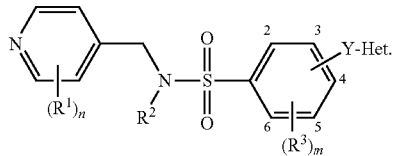

Compounds of formula

| ex. no | (R¹)ₙ | R² | (R³)ₘ | Position Y-Het | Y | Het | m.p. [° C.]; HPLC Rₜ [min], MS (M + H⁺), ¹H-NMR (CDCl₃, ppm) |
|---|---|---|---|---|---|---|---|
| 300 | 2-CH₃, 3-CH₃ | H | — | 4-Y-Het | —S— | 3-chloro-5-trifluoromethylpyridin-2-yl | 161-164° C. |
| 301 | 2-OCH₃ | H | — | 4-Y-Het | —O— | 5-methoxycarbonylpyridin-2-yl | 144-148° C. |
| 302 | 2-CH₃, 3-CH₃ | H | — | 4-Y-Het | —O— | 5-methoxycarbonylpyridin-2-yl | 2.42 min, 428.25 |
| 303 | 2-OCH₃ | H | — | 4-Y-Het | —O— | 3-chloro-5-ethoxycarbonylpyridin-2-yl | 133-136° C. |
| 304 | 2-CH₃, 3-CH₃ | H | — | 4-Y-Het | —O— | 3-chloro-5-ethoxycarbonylpyridin-2-yl | 2.85 min, 475.60 |
| 305 | 2-OCH₃ | H | 3-CH₃ | 4-Y-Het | —O— | 3-fluoro-5-chloropyridin-2-yl | 97-100° C. |
| 306 | 2-CH₃, 3-CH₃ | H | 3-CH₃ | 4-Y-Het | —O— | 3-fluoro-5-chloropyridin-2-yl | 141-144° C. |
| 307 | 2-OCH₃ | H | — | 4-Y-Het | —O— | pyridin-3-yl | 1.78 min, 371.70 |
| 308 | 2-CH₃, 3-CH₃ | H | — | 4-Y-Het | —O— | pyridin-3-yl | 1.60 min, 369.80 |
| 309 | 2-OCH₃ | H | — | 4-Y-Het | —O— | 3-bromo-5-methylpyridin-2-yl | 3.13 min, 465.60 |
| 310 | 2-CH₃, 3-CH₃ | H | — | 4-Y-Het | —O— | 3-bromo-5-methylpyridin-2-yl | 2.66 min, 463.60 |
| 311 | 2-OCH₃ | H | — | 4-Y-Het | —OCH₂— | 1,3-dimethyl-1H-pyrazol-5-yl | 120-125° C. |
| 312 | 2-CH₃, 3-CH₃ | H | — | 4-Y-Het | —OCH₂— | 1,3-dimethyl-1H-pyrazol-5-yl | 162-164° C. |
| 313 | 2-OCH₃ | H | — | 4-Y-Het | —S— | 5-trifluoromethylpyridin-2-yl | 109-113° C. |
| 314 | 2-CH₃, 3-CH₃ | H | — | 4-Y-Het | —S— | 5-trifluoromethylpyridin-2-yl | 129-133° C. |
| 315 | 2-CH₃, 3-CH₃ | H | — | 4-Y-Het | —O— | 3-chloropyridin-4-yl | 1.92 min, 402.70 |
| 316 | — | H | 3-CH₃ | 4-Y-Het | —O— | 2-fluoro-3-chloropyridin-2-yl | 150-152° C. |
| 317 | 3-OCH₃ | H | 3-CH₃ | 4-Y-Het | —O— | 2-fluoro-3-chloropyridin-2-yl | 2.77 min, 437.70 |
| 318 | — | H | — | 4-Y-Het | —S— | 5-trifluoromethylpyridin-2-yl | 176-179° C. |
| 319 | 3-OCH₃ | H | — | 4-Y-Het | —S— | 5-trifluoromethylpyridin-2-yl | 2.80 min, 455.60 |
| 320 | — | H | 2-CH₃ | 4-Y-Het | —O— | 2-fluoro-3-chloropyridin-2-yl | 2.62 min, 407.70 |
| 321 | 3-OCH₃ | H | 2-CH₃ | 4-Y-Het | —O— | 2-fluoro-3-chloropyridin-2-yl | 157-158° C. |
| 322 | 2-OCH₃ | H | — | 4-Y-Het | —OCH₂— | thiazol-4-yl | 142-144° C. |
| 323 | 2-CH₃, 3-CH₃ | H | — | 4-Y-Het | —OCH₂— | thiazol-4-yl | 247-250° C. |
| 324 | 2-OCH₃ | H | — | 4-Y-Het | —OCH₂— | 1-methyl-3-trifluoromethyl-1H-pyrazol-5-yl | 2.90 min, 456.70 |
| 325 | 2-CH₃, 3-CH₃ | H | — | 4-Y-Het | —OCH₂— | 1-methyl-3-trifluoromethyl-1H-pyrazol-5-yl | 216-218° C. |
| 326 | 2-CH₃, 3-CH₃ | H | — | 4-Y-Het | —OCH₂— | 1-methyl-3-cyclopropyl-1H-pyrazol-5-yl | 112-119° C. |
| 327 | 2-CH₃, 3-CH₃ | H | — | 4-Y-Het | —OCH₂— | 5-trifluoromethylpyridin-2-yl | 142° C. |
| 328 | 2-OCH₃ | H | — | 4-Y-Het | —N(CH₃)— | 3-chloro-5-trifluoromethylpyridin-2-yl | 122-124° C. |
| 329 | 2-CH₃, 3-CH₃ | H | — | 4-Y-Het | —N(CH₃)— | 3-chloro-5-trifluoromethylpyridin-2-yl | 2.88 min, 484.60 |
| 330 | — | H | — | 4-Y-Het | —N(CH₃)— | 3-chloro-5-trifluoromethylpyridin-2-yl | 84-88° C. |
| 331 | 3-OCH₃ | H | — | 4-Y-Het | —N(CH₃)— | 3-chloro-5-trifluoromethylpyridin-2-yl | 2.91 min, 486.60 |
| 332 | 2-CH₃, 3-CH₃ | H | — | 4-Y-Het | —OCH₂— | 4,6-dimethoxypyrimidin-2-yl | 145-148° C. |
| 333 | — | H | — | 4-Y-Het | —N(CH₃)— | 5-trifluoromethylpyridin-2-yl | 2.57 min, 423.05 |
| 334 | 2-OCH₃ | H | — | 4-Y-Het | —N(CH₃)— | 5-trifluoromethylpyridin-2-yl | 3.08 min, 453.23 |
| 335 | 3-OCH₃ | H | — | 4-Y-Het | —N(CH₃)— | 5-trifluoromethylpyridin-2-yl | 2.68 min, 453.25 |
| 336 | 2-CH₃, 3-CH₃ | H | — | 4-Y-Het | —N(CH₃)— | 5-trifluoromethylpyridin-2-yl | 2.71 min, 451.25 |
| 337 | 2-OCH₃ | H | 2-CH₃ | 4-Y-Het | —O— | 2-fluoro-3-chloropyridin-2-yl | 3.22 min, 438.15 |
| 338 | 2-CH₃, 3-CH₃ | H | 2-CH₃ | 4-Y-Het | —O— | 2-fluoro-3-chloropyridin-2-yl | 2.70 min, 436.15 |
| 339 | 2-OCH₃ | H | — | 4-Y-Het | —OCH₂— | 1-methyl-3-cyclopropyl-1H-pyrazol-5-yl | 2.53 min, 429.25 |
| 340 | 2-OCH₃ | H | — | 4-Y-Het | —OCH₂— | 2-trifluoromethylthiazol-4-yl | 111-114° C. |
| 341 | 2-CH₃, 3-CH₃ | H | — | 4-Y-Het | —OCH₂— | 2-trifluoromethylthiazol-4-yl | 127-129° C. |
| 342 | 2-OCH₃ | H | — | 4-Y-Het | —OCH₂— | benzothiazol-2-yl | 186-188° C. |
| 343 | 2-CH₃, 3-CH₃ | H | — | 4-Y-Het | —OCH₂— | benzothiazol-2-yl | 190-193° C. |
| 344 | 2-OCH₃ | H | — | 4-Y-Het | —OCH₂— | 3-methylisoxazol-5-yl | 127-130° C. |
| 345 | 2-CH₃, 3-CH₃ | H | — | 4-Y-Het | —OCH₂— | 3-methylisoxazol-5-yl | 146-148° C. |
| 346 | 2-CH₃, 6-CH₃ | H | — | 4-Y-Het | —OCH₂— | 5-trifluoromethylpyridin-2-yl | 2.65 min, 438.25 |
| 347 | 2-SCH₃ | H | 3-CH₃ | 4-Y-Het | —O— | 5-trifluoromethylpyridin-2-yl | 3.10 min, 469.60 |
| 348 | 2-SCH₃ | H | 3-CH₃ | 4-Y-Het | —O— | 3-chloro-5-trifluoromethylpyridin-2-yl | 127-130° C. |
| 349 | 2-SCH₃ | H | 2-CH₃ | 4-Y-Het | —O— | 5-trifluoromethylpyridin-2-yl | 3.17 min, 470.15 |
| 350 | 2-SCH₃ | H | 2-CH₃ | 4-Y-Het | —O— | 3-chloro-5-trifluoromethylpyridin-2-yl | 3.45 min, 504.15 |
| 351 | 2-OCH₃ | H | 2-CH₃ | 4-Y-Het | —O— | 3-chloro-5-trifluoromethylpyridin-2-yl | 3.06 min, 541.50 |
| 352 | 2-CH₃, 3-CH₃ | H | 2-CH₃ | 4-Y-Het | —O— | 3-chloro-5-trifluoromethylpyridin-2-yl | 143-146° C. |
| 353 | 2-OCH₃ | H | — | 4-Y-Het | —O— | 4,6-dimethoxypyrimidin-2-yl | 2.64 min, 447.25 |
| 354 | 2-CH₃, 3-CH₃, 5-CH₃ | H | — | 4-Y-Het | —O— | 5-trifluoromethylpyridin-2-yl | 145-148° C. |
| 355 | 2-CH₃, 3-CH₃, 5-CH₃ | H | — | 4-Y-Het | —O— | 3-chloro-5-trifluoromethylpyridin-2-yl | 2.93 min, 485.60 |
| 356 | 2-CH₃, 3-CH₃, 5-CH₃ | H | 3-CH₃ | 4-Y-Het | —O— | 5-trifluoromethylpyridin-2-yl | 2.79 min, 465.70 |

TABLE I-continued

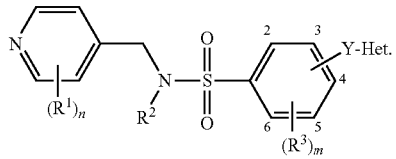

Compounds of formula (I)

| ex. no | $(R^1)_n$ | $R^2$ | $(R^3)_m$ | Position Y-Het | Y | Het | m.p. [° C.]; HPLC $R_t$ [min], MS (M + H$^+$), $^1$H-NMR (CDCl$_3$, ppm) |
|---|---|---|---|---|---|---|---|
| 357 | 2-CH$_3$, 3-CH$_3$, 5-CH$_3$ | H | 3-CH$_3$ | 4-Y-Het | —O— | 3-chloro-5-trifluoromethylpyridin-2-yl | 3.04 min, 499.60 |
| 358 | 2-CH$_3$, 3-CH$_3$, 5-CH$_3$ | H | 2-CH$_3$ | 4-Y-Het | —O— | 5-trifluoromethylpyridin-2-yl | 2.82 min, 466.25 |
| 359 | 2-CH$_3$, 3-CH$_3$, 5-CH$_3$ | H | 2-CH$_3$ | 4-Y-Het | —O— | 3-chloro-5-trifluoromethylpyridin-2-yl | 3.06 min, 500.25 |
| 360 | 2-F | H | — | 4-Y-Het | —O— | 5-trifluoromethylpyridin-2-yl | 2.56 min, 410.15 |
| 361 | 2-F | H | — | 4-Y-Het | —O— | 3-chloro-5-trifluoromethylpyridin-2-yl | 2.83 min, 444.15 |
| 362 | 2-F | H | 3-CH$_3$ | 4-Y-Het | —O— | 5-trifluoromethylpyridin-2-yl | 2.71 min, 424.15 |
| 363 | 2-F | H | 3-CH$_3$ | 4-Y-Het | —O— | 3-chloro-5-trifluoromethylpyridin-2-yl | 2.96 min, 458.15 |
| 364 | 2-F | H | 2-CH$_3$ | 4-Y-Het | —O— | 5-trifluoromethylpyridin-2-yl | 2.71 min, 424.15 |
| 365 | 2-F | H | 2-CH$_3$ | 4-Y-Het | —O— | 3-chloro-5-trifluoromethylpyridin-2-yl | 2.83 min, 458.15 |
| 366 | 2-OCH$_3$ | H | — | 4-Y-Het | —OCH$_2$— | pyrimidin-2-yl | 133-137° C. |
| 367 | 2-CH$_3$, 3-CH$_3$ | H | — | 4-Y-Het | —OCH$_2$— | pyrimidin-2-yl | 156-163° C. |
| 368 | — | H | 2,5,6-(CH$_3$)$_3$ | 4-Y-Het | —O— | 3-chloro-5-trifluoromethylpyridin-2-yl | 185-188° C. |
| 369 | 2-OCH$_3$ | H | 2,5,6-(CH$_3$)$_3$ | 4-Y-Het | —O— | 3-chloro-5-trifluoromethylpyridin-2-yl | 142-145° C. |
| 370 | 2-CH$_3$, 3-CH$_3$ | H | 2,5,6-(CH$_3$)$_3$ | 4-Y-Het | —O— | 3-chloro-5-trifluoromethylpyridin-2-yl | 169-172° C. |
| 371 | — | H | 2,3,6-(CH$_3$)$_3$ | 4-Y-Het | —O— | | 93-97° C. |
| 372 | 2-OCH$_3$ | H | 2,3,6-(CH$_3$)$_3$ | 4-Y-Het | —O— | 3-chloro-5-trifluoromethylpyridin-2-yl | 127-129° C. |
| 373 | 2-CH$_3$, 3-CH$_3$ | H | 2,3,6-(CH$_3$)$_3$ | 4-Y-Het | —O— | 3-chloro-5-trifluoromethylpyridin-2-yl | 160-163° C. |
| 374 | — | H | 2,5,6-(CH$_3$)$_3$ | 4-Y-Het | —O— | 5-trifluoromethylpyridin-2-yl | 173-176° C. |
| 375 | 2-OCH$_3$ | H | 2,5,6-(CH$_3$)$_3$ | 4-Y-Het | —O— | 5-trifluoromethylpyridin-2-yl | 127-130° C. |
| 376 | 2-CH$_3$, 3-CH$_3$ | H | 2,5,6-(CH$_3$)$_3$ | 4-Y-Het | —O— | 5-trifluoromethylpyridin-2-yl | 138-141° C. |
| 377 | 2-OCH$_3$ | H | — | 4-Y-Het | —SO$_2$— | 3-chloro-5-trifluoromethylpyridin-2-yl | 177-181° C. |
| 378 | 2-CH$_3$, 3-CH$_3$ | H | — | 4-Y-Het | —SO$_2$— | 3-chloro-5-trifluoromethylpyridin-2-yl | 214-217° C. |
| 379 | 2-CH$_3$, 3-CH$_3$ | CH$_2$Ph | — | 4-Y-Het | —O— | 3-chloro-5-trifluoromethylpyridin-2-yl | 122-127° C. |
| 380 | 2-SO$_2$ | H | 3-CH$_3$ | 4-Y-Het | —O— | 5-trifluoromethylpyridin-2-yl | 3.27 min, 502.15 |
| 381 | 2-SO$_2$ | H | 2-CH$_3$ | 4-Y-Het | —O— | 5-trifluoromethylpyridin-2-yl | 146-151° C. |
| 382 | 2-SO$_2$ | H | 2-CH$_3$ | 4-Y-Het | —O— | 3-chloro-5-trifluoromethylpyridin-2-yl | 3.54 min, 536.15 |
| 383 | 2-SO$_2$ | H | 3-CH$_3$ | 4-Y-Het | —O— | 3-chloro-5-trifluoromethylpyridin-2-yl | 203-207° C. |
| 384 | — | H | 3-OCH$_3$ | 4-Y-Het | —O— | 3-chloro-5-trifluoromethylpyridin-2-yl | 2.80 min, 473.60 |
| 385 | 2-OCH$_3$ | H | 3-OCH$_3$ | 4-Y-Het | —O— | 3-chloro-5-trifluoromethylpyridin-2-yl | 3.25 min, 503.60 |
| 386 | 2-CH$_3$, 3-CH$_3$ | H | 3-OCH$_3$ | 4-Y-Het | —O— | 3-chloro-5-trifluoromethylpyridin-2-yl | 125-127° C. |
| 387 | — | H | 2,3,5-(CH$_3$)$_3$ | 4-Y-Het | —O— | 5-trifluoromethylpyridin-2-yl | 140-147° C. |
| 388 | 2-OCH$_3$ | H | 2,3,5-(CH$_3$)$_3$ | 4-Y-Het | —O— | 5-trifluoromethylpyridin-2-yl | 88-93° C. |
| 389 | 2-CH$_3$, 3-CH$_3$ | H | 2,3,5-(CH$_3$)$_3$ | 4-Y-Het | —O— | 5-trifluoromethylpyridin-2-yl | 213-218° C. |
| 390 | 2-OCH$_3$ | H | — | 4-Y-Het | —O— | quinolin-4-yl | 2.0 min, 422.25 |
| 391 | 2-CH$_3$, 3-CH$_3$ | H | — | 4-Y-Het | —O— | quinolin-4-yl | 1.8 min, 420.25 |
| 392 | —(CH)$_4$— | H | — | 4-Y-Het | —O— | 3-trifluoromethyl-5-chloropyridin-2-yl | 3.03 min, 494.15 |
| 393 | —(CH)$_4$— | H | — | 4-Y-Het | —O— | 3-methyl-5-trifluoromethylpyridin-2-yl | 2.98 min, 474.25 |
| 394 | —(CH)$_4$— | H | — | 4-Y-Het | —O— | 6-trifluoromethylpyridin-2-yl | 2.75 min, 460.25 |
| 395 | —(CH)$_4$— | H | — | 4-Y-Het | —O— | 3-fluoro-5-trifluoromethylpyridin-2-yl | 2.85 min, 478.15 |
| 396 | 2-OCH$_3$ | H | 2,3,5-(CH$_3$)$_3$ | 4-Y-Het | —O— | 3-chloro-5-trifluoromethylpyridin-2-yl | 142-145° C. |
| 397 | 2-CH$_3$, 3-CH$_3$ | H | 2,3,5-(CH$_3$)$_3$ | 4-Y-Het | —O— | 3-chloro-5-trifluoromethylpyridin-2-yl | 169-172° C. |
| 398 | 2-CH$_2$CH$_2$CH$_3$, 3-OCH$_3$ | | — | 4-Y-Het | —O— | 5-trifluoromethylpyridin-2-yl | 141-145° C. |
| 399 | 2-CH$_2$CH$_2$CH$_3$, 3-OCH$_3$ | H | — | 4-Y-Het | —O— | 3-chloro-5-trifluoromethylpyridin-2-yl | 178-181° C. |
| 400 | 2-CH$_2$CH$_2$CH$_3$, 3-OCH$_3$ | H | 3-CH$_3$ | 4-Y-Het | —O— | 5-trifluoromethylpyridin-2-yl | 3.03 min, 495.70 |
| 401 | 2-CH$_2$CH$_2$CH$_3$, 3-OCH$_3$ | H | 3-CH$_3$ | 4-Y-Het | —O— | 3-chloro-5-trifluoromethylpyridin-2-yl | 131-134° C. |
| 402 | 2-CH$_2$CH$_2$CH$_3$, 3-OCH$_3$, | H | 2-CH$_3$ | 4-Y-Het | —O— | 5-trifluoromethylpyridin-2-yl | 70-75° C. |
| 403 | 2-CH$_2$CH$_2$CH$_3$, 3-OCH$_3$ | H | 2-CH$_3$ | 4-Y-Het | —O— | 3-chloro-5-trifluoromethylpyridin-2-yl | 146-149° C. |
| 404 | 2,3,4,5-F$_4$ | H | — | 4-Y-Het | —O— | 5-trifluoromethylpyridin-2-yl | 96-99° C. |
| 405 | 2,3,4,5-F$_4$ | H | — | 4-Y-Het | —O— | 3-chloro-5-trifluoromethylpyridin-2-yl | 70-75° C. |
| 406 | 2,3,4,5-F$_4$ | H | 3-CH$_3$ | 4-Y-Het | —O— | 5-trifluoromethylpyridin-2-yl | 124-129° C. |
| 407 | 2,3,4,5-F$_4$ | H | 3-CH$_3$ | 4-Y-Het | —O— | 3-chloro-5-trifluoromethylpyridin-2-yl | 96-100° C. |
| 408 | 2,3,4,5-F$_4$ | H | 2-CH$_3$ | 4-Y-Het | —O— | 5-trifluoromethylpyridin-2-yl | 126-131° C. |
| 409 | 2,3,4,5-F$_4$ | H | 2-CH$_3$ | 4-Y-Het | —O— | 3-chloro-5-trifluoromethylpyridin-2-yl | 136-142° C. |
| 410 | 2-OCH$_3$ | H | — | 4-Y-Het | —O— | 5-methylaminopyridin-2-yl | 1.92 min, 400.70 |

TABLE I-continued

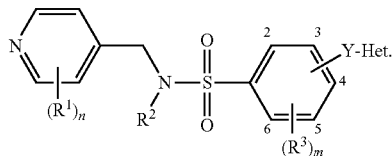

Compounds of formula

| ex. no | $(R^1)_n$ | $R^2$ | $(R^3)_m$ | Position Y-Het | Y | Het | m.p. [° C.]; HPLC $R_t$ [min], MS (M + H$^+$), $^1$H-NMR (CDCl$_3$, ppm) |
|---|---|---|---|---|---|---|---|
| 411 | 2-CH$_3$, 3-CH$_3$ | H | — | 4-Y-Het | —O— | 5-methylaminopyridin-2-yl | 1.80, 398.80 |
| 412 | — | H | — | 4-Y-Het | —O— | 5-dimethylaminopyridin-2-yl | 1.87 min, 385.25 |
| 413 | 2-OCH$_3$ | H | — | 4-Y-Het | —O— | 5-dimethylaminopyridin-2-yl | 2.18 min, 415.25 |
| 414 | 2-CH$_3$, 3-CH$_3$ | H | — | 4-Y-Het | —O— | 5-dimethylaminopyridin-2-yl | 2.00 min, 413.25 |
| 415 | 2-OCHF$_2$ | H | — | 4-Y-Het | —O— | 5-trifluoromethylpyridin-2-yl | 116-120° C. |
| 416 | 2-OCHF$_2$ | H | — | 4-Y-Het | —O— | 3-chloro-5-trifluoromethylpyridin-2-yl | 90-94° C. |
| 417 | 2-OCHF$_2$ | H | 3-CH$_3$ | 4-Y-Het | —O— | 5-trifluoromethylpyridin-2-yl | 102-106° C. |
| 418 | 2-OCHF$_2$ | H | 3-CH$_3$ | 4-Y-Het | —O— | 3-chloro-5-trifluoromethylpyridin-2-yl | 148-152° C. |
| 419 | 2-OCHF$_2$ | H | 2-CH$_3$ | 4-Y-Het | —O— | 5-trifluoromethylpyridin-2-yl | 3.70 min, 489.60 |
| 420 | 2-OCHF$_2$ | H | 2-CH$_3$ | 4-Y-Het | —O— | 3-chloro-5-trifluoromethylpyridin-2-yl | 3.93 min, 523.50 |
| 421 | 2-CH$_3$, 3-CH$_3$ | H | — | 4-Y-Het | —O— | 5-hex-1-ynyl-pyridin-5-yl | 3.36 min, 450.35 |
| 422 | 2-CH$_3$, 3-CH$_3$ | H | — | 4-Y-Het | —NH— | 5-trifluoromethylpyridin-2-yl | 106° C. |
| 423 | 2-CH$_3$, 6-CH$_3$ | H | 3-CH$_3$ | 4-Y-Het | —O— | 5-trifluoromethylpyridin-2-yl | 2.77 min, 452.25 |
| 424 | 2-CH$_3$, 3-CH$_3$ | H | — | 4-Y-Het | —CH$_2$— | 3-chloro-5-trifluoromethylpyridin-2-yl | 127° C. |
| 425 | 2-OCH$_3$ | CH$_3$ | — | 4-Y-Het | —CH$_2$O— | 3-chloro-5-trifluoromethylpyridin-2-yl | 132° C. |
| 426 | 2-CH$_3$, 3-CH$_3$ | H | — | 4-Y-Het | —O— | 5-thiomethylpyridin-2-yl | 2.51 min, 416.25 |
| 427 | 2-OCH$_3$ | H | — | 4-Y-Het | —O— | 5-thiomethylpyridin-2-yl | 66.5° C. |
| 428 | 2-CH$_3$, 3-CH$_3$ | H | — | 4-Y-Het | —CO— | 5-chloropyridin-2-yl | 178.5° C. |
| 429 | 2-CH$_3$, 6-CH$_3$ | H | — | 4-Y-Het | —O— | 3-chloro-5-trifluoromethylpyridin-2-yl | 128-131° C. |
| 430 | 2-CH$_3$, 6-CH$_3$ | H | 3-CH$_3$ | 4-Y-Het | —O— | 3-chloro-5-trifluoromethylpyridin-2-yl | 3.01 min, 486.25 |
| 431 | 2-CH$_3$, 6-CH$_3$ | H | 2-CH$_3$ | 4-Y-Het | —O— | 5-trifluoromethylpyridin-2-yl | 104-107° C. |
| 432 | 2-CH$_3$, 6-CH$_3$ | H | 2-CH$_3$ | 4-Y-Het | —O— | 3-chloro-5-trifluoromethylpyridin-2-yl | 3.02, 486.15 |
| 433 | 2-CH$_3$, 3-OCH$_3$ | H | 2-CH$_3$ | 4-Y-Het | —O— | 5-trifluoromethylpyridin-2-yl | 2.75 min, 468.25 |
| 434 | 2-CH$_3$, 3-OCH$_3$ | H | 2-CH$_3$ | 4-Y-Het | —O— | 3-chloro-5-trifluoromethylpyridin-2-yl | 3.01 min, 502.25 |
| 435 | 2-CH$_3$, 3-OCH$_3$ | H | 3-CH$_3$ | 4-Y-Het | —O— | 5-trifluoromethylpyridin-2-yl | 2.77 min, 468.25 |
| 436 | 2-CH$_3$, 3-OCH$_3$ | H | 3-CH$_3$ | 4-Y-Het | —O— | 3-chloro-5-trifluoromethylpyridin-2-yl | 141-144° C. |
| 437 | 2-CH$_3$, 3-OCH$_3$ | H | — | 4-Y-Het | —O— | 5-chloropyridin-2-yl | 2.46 min, 420.15 |
| 438 | 2-CH$_3$, 3-OCH$_3$ | H | — | 4-Y-Het | —O— | 3,5-dichloropyridin-2-yl | 134-138° C. |
| 439 | 2-CH$_3$, 3-OCH$_3$ | H | 2-CH$_3$ | 4-Y-Het | —O— | 5-chloropyridin-2-yl | 2.59 min, 435.15 |
| 440 | 2-CH$_3$, 3-OCH$_3$ | H | 2-CH$_3$ | 4-Y-Het | —O— | 3,5-dichloropyridin-2-yl | 2.84 min, 468,15 |
| 441 | 2-OCH$_3$ | H | — | 4-Y-Het | —CH$_2$O— | 3-chloro-5-trifluoromethylpyridin-2-yl | 127-129° C. |

— when referring to $(R^1)_n$ means that n is zero;
— when referring to $(R^3)_m$ means that m is zero;
—(CH)$_4$— when referring to $(R^1)_n$ means that two radicals bound to the 2- and 3-postion of the pyridine moiety together with the carbon atoms to which they are bound form a fused phenyl ring;
CH$_2$Ph = Phenylmethyl;
m.p. = melting point.
HPLC column: RP-18 column (Chromolith Speed ROD from Merck KgaA, Germany), 50 mm × 4.6 mm
Eluent: acetonitrile + 0.1% trifluoroacetic acid (TFA)/water + 0.1% TFA (gradient from 5:95 to 95:5 in 5 min at 40° C., flow of 1,8 ml/min)
MS: Quadrupol Elektrospray Ionisation, 80 V (positive mode)

III. Examples of the Action Against Harmful Fungi

The fungicidal action of the compounds (I) was demonstrated by the following experiments:

A) Microtiter Tests

The active compounds were formulated separately as a stock solution in DMSO at a concentration of 10 000 ppm.

The stock solution was pipetted into a microtiter plate (MTP) and diluted to the stated active compound concentration using nutrient medium as specified in the respective use example. An aqueous spore suspension as specified in the respective use example was then added. The plates were placed in a water vapor-saturated chamber at temperatures of 18° C.

Using an absorption photometer, the microtiter plates were measured at 405 nm on day 7 after the inoculation. The measured parameters were compared to the growth of the active compound-free control variant (=100%) and the fungus- and active compound-free blank value to determine the relative growth in % of the pathogens in the individual active compounds.

Use Example 1

Activity Against the Late Blight Pathogen *Phytophthora infestans*

A pea juice-based aqueous nutrient medium for fungi and an aqueous zoospore suspension of *Phytophthora infestans* were used.

In this test, the sample which had been treated with 125 ppm of the active compound from examples 3, 13, 55, 56, 61, 67 and 68, respectively, showed up to at most 15% growth of the pathogen.

Use Example 2

Activity Against the Rice Blast Pathogen Caused by *Pyricularia Oryzae*

A malt-based aqueous nutrient medium for fungi and an aqueous spore suspension of *Pyricularia oryzae* were used.

In this test, the sample which had been treated with 125 ppm of the active compound from examples 7, 12, 13, 15, 16, 17, 31, 33, 45, 46, 55, 56, 61 and 68, respectively, showed up to at most 15% relative growth of the pathogen.

Use Example 3

Activity Against the *Septoria* Blotch Pathogen Caused by *Septoria tritici*

A malt-based aqueous nutrient medium for fungi and an aqueous spore suspension of *Septoria tritici* were used.

In this test, the sample which had been treated with 125 ppm of the active compound from examples 7, 12, 13, 15, 16, 17, 31, 33, 45 and 46, respectively, showed up to at most 25% relative growth of the pathogen.

Use Example 4

Activity Against *Leptosphaeria nodorum*

An aqueous medium solution (containing yeast extract, bactopeptone and glycerol) and a spore suspension of *Leptosphaeria nodorum* were used.

In this test, the sample which had been treated with 125 ppm of the active compound from examples 9, 28, 45, 71 and 74, respectively, showed up to at most 25% relative growth of the pathogen.

Use Example 5

Activity against *Ustilago maydis*

An aqueous medium solution (containing yeast extract, bactopeptone and glycerol) and a spore suspension of *Ustilago maydis* were used.

In this test, the sample which had been treated with 125 ppm of the active compound from examples 7, 28, 33, 45, 71, 74 and 203, respectively, showed up to at most 25% relative growth of the pathogen.

Use Example 6

Activity Against *Corynespora cassiicola*

An aqueous medium solution (containing yeast extract, bactopeptone and glycerol) and a spore suspension of *Corynespora cassiicola* were used.

In this test, the sample which had been treated with 125 ppm of the active compound from examples 7 and 28, respectively, showed up to at most 25% relative growth of the pathogen.

Use Example 7

Activity Against *Septoria Glycines*

An aqueous medium solution (containing yeast extract, bactopeptone and glycerol) and a spore suspension of *Septoria* glycines were used.

In this test, the sample which had been treated with 125 ppm of the active compound from example 8 showed up to at most 25% relative growth of the pathogen.

Use Example 8

Activity Against *Scerotinia sclerotinum*

An aqueous medium solution (containing yeast extract, bactopeptone and glycerol) and a spore suspension of *Scerotinia scerotinum* were used.

In this test, the sample which had been treated with 125 ppm of the active compound from examples 7, 8, 27, 28, 33, 35, 45, 64, 71, 74 and 203, respectively, showed up to at most 25% relative growth of the pathogen.

Use Example 9

Activity Against *Mycosphaerella fijiensis* (Benzimidazole-Resistant Isolate)

An aqueous medium solution (containing yeast extract, bactopeptone and glycerol) and a spore suspension of *Mycosphaerella fijiensis* were used.

In this test, the sample which had been treated with 125 ppm of the active compound from examples 7, 8, 8, 9, 12, 13, 27, 28, 33, 35, 45, 64, 71, 74, 160 and 203, respectively, showed up to at most 25% relative growth of the pathogen.

Use Example 10

Activity Against *Mycosphaerella fijiensis* (Benzimidazole-Sensitive Isolate

An aqueous medium solution (containing yeast extract, bactopeptone and glycerol) and a spore suspension of *Mycosphaerella fijensis* were used.

In this test, the sample which had been treated with 125 ppm of the active compound from examples 7, 28, 45, 71, 74 and 203, respectively, showed up to at most 25% relative growth of the pathogen.

Use Example 11

Activity Against *Cercospora Sojina*

An aqueous medium solution (containing yeast extract, bactopeptone and glycerol) and a spore suspension of *Cercospora sojina* were used.

In this test, the sample which had been treated with 125 ppm of the active compound from examples 7, 8, 9, 45, 71, 74 and 203, respectively, showed up to at most 25% relative growth of the pathogen.

Use Example 12

Activity against *Microdochium nivale* (Benzimidazole-Resistant Isolate)

An aqueous medium solution (containing yeast extract, bactopeptone and glycerol) and a spore suspension of *Microdochium nivale* were used.

In this test, the sample which had been treated with 125 ppm of the active compound from examples 8, 28, 45, 71, 74 and 203, respectively, showed up to at most 25% relative growth of the pathogen.

Use Example 13

Activity Against *Microdochium nivale* (Benzimidazole-Sensitive Isolate)

An aqueous medium solution (containing yeast extract, bactopeptone and glycerol) and a spore suspension of *Microdochium nivale* were used.

In this test, the sample which had been treated with 125 ppm of the active compound from examples 8, 28 and 71, respectively, showed up to at most 25% relative growth of the pathogen.

B) Greenhouse Tests

The active compounds were formulated separately or together as a stock solution comprising 25 mg of active compound which was made up to 10 ml using a mixture of acetone and/or DMSO and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active compound concentration given below.

Use Example 14

Activity Against Early Blight on Tomatoes Caused by *Phytophthora infestans* with Protective Application Young seedlings of tomato plants were grown in pots. The plants were sprayed to runoff with an aqueous suspension containing the concentration of active ingredient stated below. The next day, the treated plants were inoculated with an aqueous suspension of sporangia of *Phytophthora infestans*. After inoculation, the trial plants were immediately transferred to a humid chamber. After 6 days at 18 to 20° C. and a relative humidity close to 100%, the extent of fungal attack on the leaves was visually assessed as % diseased leaf area.

In this test, the plants which had been treated with 250 ppm of the active compound from examples 5, 8, 9, 11, 13, 32, 34, 35, 36, 38, 39, 40, 41, 43, 47, 48, 49, 50, 51, 52, 53, 54, 58, 59, 60, 61, 62, 63, 64, 65, 66, 70, 71, 73, 74, 72, 76, 79, 86, 92, 93, 96, 97, 98, 100, 102, 104, 106, 112, 116, 117, 124, 127, 128, 129, 159, 160, 162, 163, 164, 165, 167, 168, 169, 170, 171, 173, 174, 175, 176, 177, 178, 179, 183, 188, 189, 190, 192, 195, 196, 199, 200, 202, 203, 208, 213, 218, 219, 229, 232, 233, 235, 236, 237, 238, 239, 240, 245, 246, 247, 251, 252, 253, 255, 257, 259, 261, 262, 263, 264, 265, 266, 268, 269, 270, 273, 274, 275, 276, 277, 278, 279, 280, 281 282, 283, 284, 285, 286, 287 288, 291, 292, 296, 297, 298, 299, 306, 307, 312, 313, 314 and 319, respectively, showed an infection of less than or equal to 15% whereas the untreated plants were 90% infected.

Use Example 1

Curative Action Against *Puccinia recondita* on Wheat (Brown Rust of Wheat)

Leaves of potted wheat seedlings of the cultivar "Kanzler" were dusted with a suspension of spores of brown rust of wheat (*Puccinia recondita*). The plants were then placed in a chamber with high atmospheric humidity (90 to 95%), at 20 to 22° C., for 24 hours. During this time, the spores germinated and the germinal tubes penetrated into the leaf tissue. The next day, the infected plants were sprayed to runoff point with an aqueous suspension having the concentration of active compound stated below. After drying of the sprayed suspension, the test plants were returned into the greenhouse and cultivated at temperatures between 20 and 22° C. and at 65 to 70% relative atmospheric humidity for a further 7 days. The extent of the rust development on the leaves was then determined visually.

In this test, the plants which had been treated with 250 ppm of the active compound from examples 5, 8, 9, 11, 14, 19, 20, 21, 29, 30, 34, 35, 36, 37, 38, 40, 41, 42, 45, 47, 50, 51, 52, 59, 63, 64 and 79 respectively, showed an infection of less than or equal to 15% whereas the untreated plants were 90% infected.

Use Example 16

Protective Action Against *Puccinia recondita* on Wheat (Brown Rust of Wheat Leaves of potted wheat seedlings of the cultivar "Kanzler" were sprayed to runoff point with an aqueous suspension having the concentration of active compound stated below. The next day, the treated plants were dusted with a suspension of spores of brown rust of wheat (*Puccinia recondita*). The plants were then placed in a chamber with high atmospheric humidity (90 to 95%), at 20 to 22° C., for 24 hours. During this time, the spores germinated and the germinal tubes penetrated into the leaf tissue. The next day, the test plants were returned into the greenhouse and cultivated at temperatures between 20 and 22° C. and at 65 to 70% relative atmospheric humidity for a further 7 days. The extent of the rust development on the leaves was then determined visually.

In this test, the plants which had been treated with 250 ppm of the active compound from examples 13, 14, 18, 19, 20, 22, 23, 27, 28, 86, 87, 89, 90, 91, 92, 93, 94, 95, 97, 98, 100, 101, 102, 103, 104, 105, 106, 107, 110, 113, 114, 115, 117, 120, 123, 125, 126, 127, 128, 159, 160, 162, 163, 164, 165, 167, 168, 174, 175, 178, 179, 180, 181, 182, 186, 187, 191, 193, 194, 195, 196, 197, 200, 201, 202, 203, 204, 205, 206, 207, 208, 210, 212, 213, 214, 215, 216, 217, 218, 219, 220, 222, 223, 224, 225, 227, 228, 229, 230, 231, 232, 233, 234, 235, 236, 237, 238, 239, 242, 244, 245, 246, 247, 250, 251, 252, 253, 254, 258, 259, 260, 269, 270, 271, 272, 277 and 278, respectively, showed an infection of less than or equal to 15% whereas the untreated plants were 90% infected.

Use Example 17

Protective Action Against *Blumeria graminis tritici* on Wheat (Mildew of Wheat)

Leaves of potted wheat seedlings of the cultivar "Kanzler" were sprayed to runoff point with an aqueous suspension having the concentration of active compound stated below. The next day, the treated plants were dusted with a suspension of spores of mildew of wheat (*Blumeria graminis tritici*). The plants were then returned into the greenhouse and cultivated at temperatures between 20 and 24° C. and at 60 to 90% relative atmospheric humidity for a further 7 days. The extent of the mildew development on the leaves was then determined visually.

In this test, the plants which had been treated with 250 ppm of the active compound from examples 14, 21, 23, 27 and 28, respectively, showed an infection of less than or equal to 15% whereas the untreated plants were 90% infected.

Use Example 18

Protective Action Against *Sphaerotheca fuliginea* on Cucumber (Mildew of Cucumber)

Leaves of potted cucumber seedlings (in the germ layer stage) were sprayed to runoff point with an aqueous suspension having the concentration of active compound stated below. The next day, the treated plants were dusted with a suspension of spores of mildew of cucumber (*Sphaerotheca fuliginea*). The plants were then returned into the greenhouse and cultivated at temperatures between 20 and 24° C. and at 60 to 80% relative atmospheric humidity for a further 7 days. The extent of the mildew development on the seed leaves was then determined visually.

In this test, the plants which had been treated with 250 ppm of the active compound from examples 32, 39, 69, 70, 71, 72, 73 and 74, respectively, showed an infection of less than or equal to 15% whereas the untreated plants were 90% infected.

Use Example 19

Protective Action Against *Phakopsora pachyrhizi* on Soybean (Rust of Soybean)

Leaves of potted soybean seedlings were sprayed to runoff point with an aqueous suspension having the concentration of active compound stated below. The next day, the treated plants were dusted with a suspension of spores of soybean rust (*Phakopsora pachyrhizi*). The plants were then placed in a chamber with high atmospheric humidity (90 to 95%), at 23 to 27° C., for 24 hours. During this time, the spores germinated and the germinal tubes penetrated into the leaf tissue. The plants were then returned into the greenhouse and cultivated at temperatures between 23 and 27° C. and at 60 to 80% relative atmospheric humidity for a further 14 days. The extent of the rust development on the leaves was then determined visually.

In this test, the plants which had been treated with 250 ppm of the active compound from examples 107, 112, 123, 197, 201, 210, 230, 243, 244, 248, 254, 256, 272, 288, 290, 293, 294, 295, 296, 297, 299, 300, 301, 302, 303, 304, 305, 306, 307, 308, 311, 312, 313, 314, 315, 317, 318 and 319, respectively, showed an infection of less than or equal to 15% whereas the untreated plants were 90% infected.

Use Example 20

Protective Action Against *Septoria tritici* on Wheat (Septoria Leaf Blotch of Wheat)

Leaves of potted wheat seedlings of the cultivar "Kanzler" were sprayed to runoff point with an aqueous suspension having the concentration of active compound stated below. Two days later, the treated plants were dusted with a suspension of spores of *Septoria* triticL The plants were then placed in a greenhouse chamber with high atmospheric humidity (90 to 95%), at 20 to 24° C., for 4 days, afterwards at temperatures between 18 and 22° C. and at about 70% relative atmospheric humidity. The extent of the disease symptom development on the leaves was determined visually after 21 days.

In this test, the plants which had been treated with 250 ppm of the active compound from examples 91, 101, 129, 169, 173, 176, 177, 180, 181, 182, 183, 184, 185, 186, 187, 188, 192, 193, 194, 205, 206, 207, 248, 260, 271, 279, 280, 281, 282, 283, 284, 285, 286, 291, 292, 293, 294, 295, 298 and 305, respectively, showed an infection of less than or equal to 15% whereas the untreated plants were 90% infected.

IV. Comparative Examples

A) Microtiter Tests

The active compounds were formulated separately as a stock solution in DMSO at a concentration of 10 000 ppm.

Use Example 21

Activity Against the Rice Blast Pathogen Caused by *Pyricularia oryzae* in the Microtiter Test The stock solution was pipetted into a microtiter plate (MTP) and diluted to the stated active compound concentration given in table 3 (31 ppm) using a malt-based aqueous nutrient medium for fungi. An aqueous spore suspension of *Pyricularia oryzae* was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (=100%) and the fungus- and active compound-free blank value to determine the relative growth in % of the pathogens in the individual active compounds. The results are shown in table II below.

TABLE II

| Compound | growth in [%] at 31 ppm |
|---|---|
| (comparative example 1 from (WO 2005/033081: table 31, No. A-81) | 97 |
| (Ex. No. 7) | 53 |

B) Greenhouse Tests

The active compounds were formulated separately or together as a stock solution comprising 25 mg of active compound which was made up to 10 ml using a mixture of acetone and/or dimethyl sulfoxide (DMSO) and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active compound concentration given below.

Use Example 22

Curative Action Against Soybean Rust caused by *Phakopsora pachyrhizi*

Leaves of potted soybean seedlings were dusted with a suspension of spores of rust of soybean (*Phakopsora pachyrhizi*). The plants were then placed in a chamber with high atmospheric humidity (90 to 95%), at 23 to 27° C., for 24 hours. During this time, the spores germinated and the germinal tubes penetrated into the leaf tissue. The next day, the infected plants were sprayed to runoff point with an aqueous suspension having the concentration of active compound stated in table 4 (250 ppm). After drying of the sprayed suspension, the test plants were returned to the greenhouse and cultivated at temperatures between 23 and 27° C. and at 60 to 80% relative atmospheric humidity for a further 14 days. The extent of the rust development on the leaves was then determined visually. The results are given in table III below.

synergistic and antagonistic responses of herbicide combinations, Weeds 15, 20-22 (1967)] and compared with the observed efficacies.

$$E = x + y - x \cdot y / 100 \qquad \text{Colby's formula}$$

E expected efficacy, expressed in % of the untreated control, when using the mixture of the compounds A and B at the concentration a and b x efficacy, expressed in % of the untreated control, when using compound A at a concentration of a y efficacy, expressed in % of the untreated control, when using compound B at a concentration of b A) Microtiter Tests The active compounds were formulated separately as a stock solution in DMSO at a concentration of 10 000 ppm. The compounds pyraclostrobin, boscalid and epoxiconazole were used as commercial finished formulations and diluted with water to the stated concentration of the active compound.

The stock solutions were mixed according to the ratio, pipetted onto a micro titer plate (MTP) and diluted with water to the stated concentrations. A spore suspension of the respective pathogen in a nutrient medium was then added as specified in the respective use example. The plates were placed in a water vapor-saturated chamber at a temperature of 18° C. Using an absorption photometer, the MTPs were measured at 405 nm 7 days after the inoculation.

TABLE III

| Compound | infection in [%] at 250 ppm |
|---|---|
| untreated control | 100 |
| 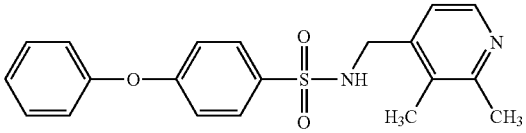 (comparative example 2 from (WO 2005/033081: Table 2, No. A-81) | 100 |
| 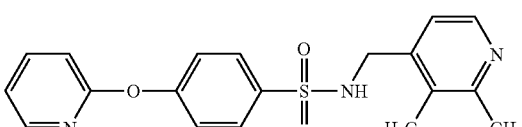 (Ex. No. 33) | 5 |

V. Synergistic Mixture Examples

The measured parameters were compared to the growth of the active compound-free control variant (100%) and the fungus-free and active compound-free blank value to determine the relative growth in % of the pathogens in the respective active compounds.

These percentages were converted into efficacies. An efficacy of 0 means that the growth level of the pathogens corresponds to that of the untreated control; an efficacy of 100 means that the pathogens were not growing.

The expected efficacies of active compound mixtures were determined using Colby's formula [R. S. Colby, Calculating Use Example 23

Activity Against the Late Blight Pathogen *Phytophthora infestans*

A spore suspension of *Phytophtora infestans* in a pea juice-based aqueous nutrient medium was used.

TABLE IV

| Compound or mixture tested | Concentration of compounds (ppm) | Mixing ratio | Observed efficacy (%) | Expected efficacy (%) |
|---|---|---|---|---|
| Ex. No. 7 | 0.016 | n.a. | 11 | n.a. |
| Ex. No. 13 | 0.25 | n.a. | 16 | n.a. |

TABLE IV-continued

| Compound or mixture tested | Concentration of compounds (ppm) | Mixing ratio | Observed efficacy (%) | Expected efficacy (%) |
|---|---|---|---|---|
| Ex. No. 28 | 0.016 | n.a. | 10 | n.a. |
| Ex. No. 160 | 1 | n.a. | 17 | n.a. |
| Epoxiconazol | 0.001 | n.a. | 0 | n.a. |
| Pyraclostrobin | 0.00025 | n.a. | 8 | n.a. |
| Boscalid | 0.016 | n.a. | 5 | n.a. |
| Captan | 0.25 | n.a. | 3 | n.a. |
|  | 0.063 | n.a. | 7 | n.a. |
|  | 0.004 | n.a. | 0 | n.a. |
| Chlorothalonil | 0.25 | n.a. | 10 | n.a. |
|  | 0.004 | n.a. | 4 | n.a. |
| Ex. No. 7 + Epoxiconazol | 0.016 0.001 | 16:1 | 30 | 11 |
| Ex. No. 7 + Captan | 0.25 0.063 | 4:1 | 57 | 34 |
| Ex. No. 13 + Captan | 1 0.25 | 4:1 | 56 | 34 |
| Ex. No. 28 + Epoxiconazol | 0.016 0.001 | 16:1 | 42 | 10 |
| Ex. No. 28 + Pyraclostrobin | 0.016 0.00025 | 63:1 | 39 | 17 |
| Ex. No. 28 + Boscalid | 0.016 0.016 | 1:1 | 41 | 14 |
| Ex. No. 28 + Captan | 0.016 0.004 | 4:1 | 38 | 10 |
| Ex. No. 28 + Chlorothalonil | 0.016 0.004 | 4:1 | 34 | 13 |
| Ex. No. 160 + Chlorothalonil | 1 0.25 | 4:1 | 44 | 25 | n.a. = not applicable

Use Example 24

Activity Against the Early Blight Pathogen *Alternaria solani*

A spore suspension of *Alternaria solani* in an aqueous biomalt solution was used.

TABLE V

| Compound or mixture tested | Concentration of compounds (ppm) | Mixing ratio | Observed efficacy (%) | Expected efficacy (%) |
|---|---|---|---|---|
| Ex. No. 7 | 0.016 | n.a. | 11 | n.a. |
| Ex. No. 8 | 0.063 | n.a. | 3 | n.a. |
| Ex. No. 12 | 0.063 | n.a. | 6 | n.a. |
| Ex. No. 33 | 0.063 | n.a. | 4 | n.a. |
| Ex. No. 45 | 0.063 | n.a. | 1 | n.a. |
| Ex. No. 64 | 0.063 | n.a. | 0 | n.a. |
| Ex. No. 71 | 0.063 | n.a. | 4 | n.a. |
| Ex. No. 74 | 0.063 | n.a. | 0 | n.a. |
| Ex. No. 203 | 0.063 | n.a. | 0 | n.a. |
| Boscalid | 0.063 | n.a. | 23 | n.a. |
| Ex. No. 8 + Boscalid | 0.063 0.063 | 1:1 | 53 | 25 |
| Ex. No. 12 + Boscalid | 0.063 0.063 | 1:1 | 62 | 27 |
| Ex. No. 33 + Boscalid | 0.063 0.063 | 1:1 | 57 | 26 |
| Ex. No. 45 + Boscalid | 0.063 0.063 | 1:1 | 49 | 23 |
| Ex. No. 64 + Boscalid | 0.063 0.063 | 1:1 | 64 | 23 |
| Ex. No. 71 + Boscalid | 0.063 0.063 | 1:1 | 67 | 26 |
| Ex. No. 74 + Boscalid | 0.063 0.063 | 1:1 | 54 | 23 |
| Ex. No. 203 + Boscalid | 0.063 0.063 | 1:1 | 52 | 23 | n.a. = not applicable

Use Example 25

Activity Against the Rice Blast Pathogen *Pyricularia oryzae*

A spore suspension of *Pyricularia oryzae* in an aqueous biomalt solution was used.

TABLE VI

| Compound or mixture tested | Concentration of compounds (ppm) | Mixing ratio | Observed efficacy (%) | Expected efficacy (%) |
|---|---|---|---|---|
| Ex. No. 7 | 0.063 | n.a. | 1 | n.a. |
| Ex. No. 12 | 0.063 | n.a. | 45 | n.a. |
| Ex. No. 27 | 0.25 | n.a. | 65 | n.a. |
|  | 0.063 | n.a. | 65 | n.a. |
| Ex. No. 28 | 0.25 | n.a. | 52 | n.a. |
|  | 0.063 | n.a. | 27 | n.a. |
| Ex. No. 33 | 0.25 | n.a. | 38 | n.a. |
| Ex. No. 45 | 0.063 | n.a. | 30 | n.a. |
| Ex. No. 64 | 1 | n.a. | 12 | n.a. |
| Ex. No. 160 | 0.25 | n.a. | 60 | n.a. |
| Pyraclostrobin | 0.001 | n.a. | 17 | n.a. |
| Captan | 0.063 | n.a. | 0 | n.a. |
| Epoxiconazol | 0.063 | n.a. | 0 | n.a. |
| Chlorothalonil | 0.063 | n.a. | 0 | n.a. |
| Ex. No. 7 + Pyraclostrobin | 0.063 0.001 | 63:1 | 78 | 18 |
| Ex. No. 12 + Pyraclostrobin | 0.063 0.001 | 63:1 | 100 | 55 |
| Ex. No. 27 + Pyraclostrobin | 0.063 0.001 | 63:1 | 100 | 71 |
| Ex. No. 27 + Captan | 0.25 0.063 | 4:1 | 87 | 65 |
| Ex. No. 28 + Pyraclostrobin | 0.063 0.001 | 63:1 | 70 | 40 |
| Ex. No. 28 + Captan | 0.25 0.063 | 4:1 | 77 | 52 |
| Ex. No. 33 + Captan | 0.25 0.063 | 4:1 | 60 | 38 |
| Ex. No. 45 + Pyraclostrobin | 0.063 0.001 | | 67 | 42 |
| Ex. No. 64 + Epoxiconazol | 1 0.063 | 16:1 | 67 | 12 |
| Ex. No. 160 + Chlorothalonil | 0.25 0.063 | 4:1 | 89 | 60 | n.a. = not applicable

Use Example 26

Activity Against the Leaf Blotch Pathogen *Septoria tritici*

A spore suspension of *Septoria tritici* in an aqueous biomalt solution was used.

TABLE VII

| Compound or mixture tested | Concentration of compounds (ppm) | Mixing ratio | Observed efficacy (%) | Expected efficacy (%) |
|---|---|---|---|---|
| Ex. No. 9 | 4 | n.a. | 2 | n.a. |
| Ex. No. 12 | 4 | n.a. | 47 | n.a. |
| Ex. No. 13 | 4 | n.a. | 39 | n.a. |
| Ex. No. 27 | 4 | n.a. | 47 | n.a. |
| Ex. No. 28 | 4 | n.a. | 29 | n.a. |
| Ex. No. 33 | 4 | n.a. | 22 | n.a. |
| Ex. No. 45 | 4 | n.a. | 50 | n.a. |
| Ex. No. 71 | 4 | n.a. | 43 | n.a. |
| Ex. No. 74 | 4 | n.a. | 58 | n.a. |
| Ex. No. 160 | 4 | n.a. | 55 | n.a. |
| Ex. No. 203 | 4 | n.a. | 45 | n.a. |
| Captan | 1 | n.a. | 31 | n.a. |
| Ex. No. 9 + Captan | 4 1 | 4:1 | 70 | 33 |

TABLE VII-continued

| Compound or mixture tested | Concentration of compounds (ppm) | Mixing ratio | Observed efficacy (%) | Expected efficacy (%) |
|---|---|---|---|---|
| Ex. No. 12 + Captan | 4 1 | 4:1 | 99 | 64 |
| Ex. No. 13 + Captan | 4 1 | 4:1 | 97 | 58 |
| Ex. No. 27 + Captan | 4 1 | 4:1 | 98 | 63 |
| Ex. No. 28 + Captan | 4 1 | 4:1 | 89 | 52 |
| Ex. No. 33 + Captan | 4 1 | 4:1 | 75 | 46 |
| Ex. No. 45 + Captan | 4 1 | 4:1 | 98 | 65 |
| Ex. No. 71 + Captan | 4 1 | 4:1 | 99 | 61 |
| Ex. No. 74 + Captan | 4 1 | 4:1 | 98 | 71 |
| Ex. No. 160 + Captan | 4 1 | 4:1 | 100 | 69 |
| Ex. No. 203 + Captan | 4 1 | 4:1 | 97 | 62 | n.a. = not applicable

Use Example 27

Activity Against the Pathogen *Fusarium culmorum*

A spore suspension of *Fusarium culmorum* in an aqueous biomalt solution was used.

TABLE VIII

| Compound or mixture tested | Concentration of compounds (ppm) | Mixing ratio | Observed efficacy (%) | Expected efficacy (%) |
|---|---|---|---|---|
| Ex. No. 7 | 16 | | 7 | |
| Ex. No. 8 | 16 | | 0 | |
| Ex. No. 9 | 16 | | 0 | |
| Ex. No. 12 | 16 | | 3 | |
| Ex. No. 13 | 16 | | 2 | |
| Ex. No. 27 | 16 | | 0 | |
| Ex. No. 28 | 16 | | 1 | |
| Ex. No. 33 | 16 | | 1 | |
| Ex. No. 45 | 16 | | 2 | |
| Ex. No. 64 | 16 | | 0 | |
| Ex. No. 71 | 16 | | 1 | |
| Ex. No. 74 | 16 | | 1 | |
| Ex. No. 160 | 16 | | 3 | |
| Ex. No. 203 | 16 | | 1 | |
| Pyraclostrobin | 0.25 | | 0 | |
| Boscalid | 16 | | 1 | |
| Captan | 4 | | 39 | |
| Chlorothalonil | 4 | | 5 | |
| Ex. No. 7 + Captan | 16 4 | 4:1 | 88 | 44 |
| Ex. No. 8 + Captan | 16 4 | 4:1 | 80 | 40 |
| Ex. No. 9 + Boscalid | 16 16 | 1:1 | 26 | 1 |
| Ex. No. 9 + Captan | 16 4 | 4:1 | 99 | 39 |
| Ex. No. 12 + Boscalid | 16 16 | 1:1 | 31 | 4 |
| Ex. No. 12 + Captan | 16 4 | 4:1 | 99 | 41 |
| Ex. No. 13 + Boscalid | 16 16 | 1:1 | 25 | 3 |
| Ex. No. 13 + Captan | 16 4 | 4:1 | 99 | 40 |
| Ex. No. 27 + Pyraclostrobin | 16 0.25 | 63:1 | 31 | 0 |
| Ex. No. 27 + Captan | 16 4 | 4:1 | 98 | 39 |
| Ex. No. 28 + Captan | 16 4 | 4:1 | 99 | 40 |
| Ex. No. 28 + Boscalid | 16 16 | 1:1 | 28 | 2 |
| Ex. No. 33 + Boscalid | 16 16 | 1:1 | 27 | 2 |
| Ex. No. 45 + Pyraclostrobin | 16 0.25 | 63:1 | 28 | 2 |
| Ex. No. 45 + Captan | 16 4 | 4:1 | 92 | 40 |
| Ex. No. 45 + Boscalid | 16 16 | 1:1 | 26 | 3 |
| Ex. No. 64 + Boscalid | 16 16 | 1:1 | 26 | 1 |
| Ex. No. 71 + Boscalid | 16 16 | 1:1 | 28 | 3 |
| Ex. No. 71 + Captan | 16 4 | 4:1 | 99 | 40 |
| Ex. No. 74 + Boscalid | 16 16 | 1:1 | 30 | 3 |
| Ex. No. 74 + Captan | 16 4 | 4:1 | 93 | 40 |
| Ex. No. 160 + Boscalid | 16 16 | 1:1 | 27 | 5 |
| Ex. No. 160 + Captan | 16 4 | 4:1 | 99 | 41 |
| Ex. No. 203 + Boscalid | 16 16 | 1:1 | 23 | 2 |
| Ex. No. 203 + Captan | 16 4 | 4:1 | 99 | 40 |
| Ex. No. 203 + Chlorothalonil | 16 4 | 4:1 | 27 | 6 | n.a. = not applicable.

Use Example 28

Activity Against the Pathogen *Colletotrichum truncatum*

A spore suspension of *Colletotrichum truncatum* in an aqueous biomalt solution was used.

TABLE IX

| Compound or mixture tested | Concentration of compounds (ppm) | Mixing ratio | Observed efficacy (%) | Expected efficacy (%) |
|---|---|---|---|---|
| Ex. No. 7 | 4 | n.a. | 20 | n.a. |
| Ex. No. 12 | 16 | n.a. | 50 | n.a. |
| Ex. No. 13 | 4 | n.a. | 26 | n.a. |
| Ex. No. 28 | 4 | n.a. | 20 | n.a. |
| Ex. No. 27 | 16 | n.a. | 45 | n.a. |
| Ex. No. 33 | 4 | n.a. | 24 | n.a. |
| Ex. No. 45 | 4 | n.a. | 25 | n.a. |
| Ex. No. 71 | 4 | n.a. | 29 | n.a. |
| Ex. No. 74 | 16 | n.a. | 35 | n.a. |
| Ex. No. 160 | 4 | n.a. | 37 | n.a. |
| Ex. No. 203 | 4 | n.a. | 36 | n.a. |
| Pyraclostrobin | 0.25 | n.a. | 60 | n.a. |
| | 0.063 | n.a. | 27 | n.a. |
| Ex. No. 7 + Pyraclostrobin | 4 0.063 | 63:1 | 88 | 42 |
| Ex. No. 12 + Pyraclostrobin | 16 0.25 | 63:1 | 100 | 80 |
| Ex. No. 13 + Pyraclostrobin | 4 0.063 | 63:1 | 86 | 46 |
| Ex. No. 28 + Pyraclostrobin | 4 0.063 | 63:1 | 64 | 42 |
| Ex. No. 27 + Pyraclostrobin | 16 0.25 | 63:1 | 100 | 78 |
| Ex. No. 33 + Pyraclostrobin | 4 0.063 | 63:1 | 78 | 44 |

TABLE IX-continued

| Compound or mixture tested | Concentration of compounds (ppm) | Mixing ratio | Observed efficacy (%) | Expected efficacy (%) |
|---|---|---|---|---|
| Ex. No. 45 + Pyraclostrobin | 4<br>0.063 | 63:1 | 87 | 45 |
| Ex. No. 71 + Pyraclostrobin | 4<br>0.063 | 63:1 | 78 | 48 |
| Ex. No. 74 + Pyraclostrobin | 16<br>0.25 | 63:1 | 100 | 74 |
| Ex. No. 160 + Pyraclostrobin | 4<br>0.063 | 63:1 | 78 | 54 |
| Ex. No. 203 + Pyraclostrobin | 4<br>0.063 | 63:1 | 81 | 54 |

Use Example 29

Activity Against the Net Blotch Pathogen *Pyrenophora teres*

A spore suspension of *Pyrenophora teres* in an aqueous biomalt solution was used.

TABLE X

| Compound or mixture tested | Concentration of compounds (ppm) | Mixing ratio | Observed efficacy (%) | Expected efficacy (%) |
|---|---|---|---|---|
| Ex. No. 7 | 1 | n.a. | 28 | n.a. |
|  | 0.25 | n.a. | 17 | n.a. |
| Ex. No. 8 | 1 | n.a. | 9 | n.a. |
|  | 0.25 | n.a. | 0 | n.a. |
| Ex. No. 12 | 0.063 | n.a. | 25 | n.a. |
| Ex. No. 13 | 0.063 | n.a. | 19 | n.a. |
| Ex. No. 27 | 1 | n.a. | 31 | n.a. |
| Ex. No. 28 | 0.25 | n.a. | 4 | n.a. |
| Ex. No. 33 | 0.25 | n.a. | 0 | n.a. |
| Ex. No. 45 | 1 | n.a. | 25 | n.a. |
| Ex. No. 64 | 0.25 | n.a. | 5 | n.a. |
| Ex. No. 71 | 0.25 | n.a. | 20 | n.a. |
| Ex. No. 74 | 0.25 | n.a. | 33 | n.a. |
| Ex. No. 160 | 0.25 | n.a. | 11 | n.a. |
| Ex. No. 203 | 0.25 | n.a. | 34 | n.a. |
| Pyraclostrobin | 0.016 | n.a. | 52 | n.a. |
| Boscalid | 0.25 | n.a. | 49 | n.a. |
| Captan | 0.063 | n.a. | 16 | n.a. |
|  | 0.016 | n.a. | 5 | n.a. |
| Ex. No. 7 + Pyraclostrobin | 1<br>0.016 | 63:1 | 93 | 66 |
| Ex. No. 7 + Boscalid | 0.25<br>0.25 | 1:1 | 78 | 57 |
| Ex. No. 8 + Pyraclostrobin | 1<br>0.016 | 63:1 | 83 | 57 |
| Ex. No. 8 + Boscalid | 0.25<br>0.25 | 1:1 | 81 | 49 |
| Ex. No. 12 + Captan | 0.25<br>0.063 | 4:1 | 62 | 38 |
| Ex. No. 13 + Captan | 0.25<br>0.063 | 4:1 | 52 | 26 |
| Ex. No. 27 + Pyraclostrobin | 1<br>0.016 | 63:1 | 88 | 67 |
| Ex. No. 28 + Boscalid | 0.25<br>0.25 | 1:1 | 73 | 51 |
| Ex. No. 33 + Boscalid | 0.25<br>0.25 | 1:1 | 81 | 49 |
| Ex. No. 45 + Pyraclostrobin | 1<br>0.016 | 63:1 | 89 | 65 |
| Ex. No. 64 + Boscalid | 0.25<br>0.25 | 1:1 | 78 | 51 |
| Ex. No. 71 + Boscalid | 0.25<br>0.25 | 1:1 | 88 | 59 |
| Ex. No. 74 + Boscalid | 0.25<br>0.25 | 1:1 | 91 | 66 |
| Ex. No. 160 + Boscalid | 0.25<br>0.25 | 1:1 | 79 | 55 |
| Ex. No. 160 + Captan | 0.25<br>0.063 | 4:1 | 53 | 25 |
| Ex. No. 203 + Boscalid | 0.25<br>0.25 | 1:1 | 88 | 66 |
| Ex. No. 203 + Captan | 0.063<br>0.016 | 4:1 | 36 | 16 | n.a. = not applicable.

Use Example 30

Activity against *Gaeumannomyces graminis*

A spore suspension of *Gaeumannomyces graminis* in an aqueous biomalt solution was used.

TABLE XI

| Compound or mixture tested | Concentration of compounds (ppm) | Mixing ratio | Observed efficacy (%) | Expected efficacy (%) |
|---|---|---|---|---|
| Ex. No. 7 | 0.25 | n.a. | 51 | n.a. |
|  | 0.063 | n.a. | 9 | n.a. |
| Ex. No. 8 | 0.063 | n.a. | 0 | n.a. |
| Ex. No. 9 | 0.25 | n.a. | 5 | n.a. |
| Ex. No. 12 | 0.016 | n.a. | 30 | n.a. |
| Ex. No. 13 | 0.063 | n.a. | 31 | n.a. |
|  | 0.016 | n.a. | 6 | n.a. |
| Ex. No. 27 | 0.016 | n.a. | 58 | n.a. |
| Ex. No. 28 | 0.063 | n.a. | 29 | n.a. |
| Ex. No. 33 | 0.25 | n.a. | 21 | n.a. |
|  | 0.063 | n.a. | 4 | n.a. |
| Ex. No. 71 | 0.063 | n.a. | 52 | n.a. |
| Epoxiconazol | 0.004 | n.a. | 2 | n.a. |
| Pyraclostrobin | 0.001 | n.a. | 57 | n.a. |
|  | 0.00025 | n.a. | 29 | n.a. |
| Captan | 0.063 | n.a. | 42 | n.a. |
|  | 0.016 | n.a. | 12 | n.a. |
| Chlorothalonil | 0.016 | n.a. | 9 | n.a. |
|  | 0.004 | n.a. | 0 | n.a. |
| Ex. No. 7 + Pyraclostrobin | 0.063<br>0.001 | 63:1 | 95 | 61 |
| Ex. No. 7 + Captan | 0.25<br>0.063 | 4:1 | 91 | 71 |
| Ex. No. 8 + Pyraclostrobin | 0.063<br>0.001 | 63:1 | 81 | 57 |
| Ex. No. 9 + Captan | 0.25<br>0.063 | 4:1 | 70 | 45 |
| Ex. No. 12 + Pyraclostrobin | 0.016<br>0.00025 | 63:1 | 72 | 51 |
| Ex. No. 13 + Pyraclostrobin | 0.063<br>0.001 | 63:1 | 96 | 70 |
| Ex. No. 13 + Chlorothalonil | 0.016<br>0.004 | 4:1 | 44 | 6 |
| Ex. No. 27 + Pyraclostrobin | 0.016<br>0.00025 | 63:1 | 92 | 70 |
| Ex. No. 28 + Epoxiconazol | 0.063<br>0.004 | 16:1 | 49 | 30 |
| Ex. No. 28 + Pyraclostrobin | 0.063<br>0.001 | 63:1 | 88 | 69 |
| Ex. No. 28 + Chlorothalonil | 0.063<br>0.016 | 4:1 | 75 | 35 |
| Ex. No. 33 + Pyraclostrobin | 0.063<br>0.001 | 63:1 | 82 | 59 |
| Ex. No. 33 + Captan | 0.25<br>0.063 | 4:1 | 81 | 54 |
| Ex. No. 71 + Captan | 0.063<br>0.016 | 4:1 | 98 | 58 |

Use Example 31

Activity Against *Thielaviopsis basicola*

A spore suspension of *Thielaviopsis basicola* in an aqueous biomalt solution was used.

TABLE XII

| Compound or mixture tested | Concentration of compounds (ppm) | Mixing ratio | Observed efficacy (%) | Expected efficacy (%) |
|---|---|---|---|---|
| Ex. No. 8 | 16 | n.a. | 6 | n.a. |
|  | 4 | n.a. | 11 | n.a. |
| Ex. No. 9 | 1 | n.a. | 11 | n.a. |
| Ex. No. 27 | 4 | n.a. | 21 | n.a. |
|  | 1 | n.a. | 1 | n.a. |
| Ex. No. 28 | 16 | n.a. | 23 | n.a. |
| Ex. No. 33 | 16 | n.a. | 9 | n.a. |
| Ex. No. 64 | 16 | n.a. | 20 | n.a. |
| Ex. No. 71 | 16 | n.a. | 56 | n.a. |
|  | 1 | n.a. | 9 | n.a. |
| Ex. No. 74 | 1 | n.a. | 32 | n.a. |
| Ex. No. 160 | 1 | n.a. | 14 | n.a. |
| Ex. No. 203 | 4 | n.a. | 13 | n.a. |
|  | 1 | n.a. | 0 | n.a. |
| Pyraclostrobin | 0.25 | n.a. | 19 | n.a. |
| Captan | 0.25 | n.a. | 40 | n.a. |
| Chlorothalonil | 1 | n.a. | 56 | n.a. |
| Ex. No. 8 + Pyraclostrobin | 16 0.25 | 63:1 | 56 | 24 |
| Ex. No. 8 + Chlorothalonil | 4 1 | 4:1 | 79 | 60 |
| Ex. No. 9 + Captan | 1 0.25 | 4:1 | 80 | 47 |
| Ex. No. 27 + Captan | 1 0.25 | 4:1 | 71 | 41 |
| Ex. No. 27 + Chlorothalonil | 4 1 | 4:1 | 88 | 65 |
| Ex. No. 28 + Pyraclostrobin | 16 0.25 | 63:1 | 93 | 37 |
| Ex. No. 33 + Pyraclostrobin | 16 0.25 | 63:1 | 85 | 26 |
| Ex. No. 64 + Pyraclostrobin | 16 0.25 | 63:1 | 61 | 35 |
| Ex. No. 71 + Pyraclostrobin | 16 0.25 | 63:1 | 87 | 64 |
| Ex. No. 71 + Captan | 1 0.25 | 4:1 | 66 | 46 |
| Ex. No. 74 + Captan | 1 0.25 | 4:1 | 85 | 60 |
| Ex. No. 160 + Captan | 1 0.25 | 4:1 | 72 | 49 |
| Ex. No. 203 + Captan | 1 0.25 | 4:1 | 80 | 40 |
| Ex. No. 203 + Chlorothalonil | 4 1 | 4:1 | 94 | 62 |

Use Example 32

Activity Against *Verticillium dahliae*

A spore suspension of *Verticillium dahliae* in an aqueous biomalt solution was used.

TABLE XIII

| Compound or mixture tested | Concentration of compounds (ppm) | Mixing ratio | Observed efficacy (%) | Expected efficacy (%) |
|---|---|---|---|---|
| Ex. No. 27 | 4 | n.a. | 56 | n.a. |
| Ex. No. 71 | 4 | n.a. | 55 | n.a. |
| Ex. No. 203 | 4 | n.a. | 56 | n.a. |
|  | 1 | n.a. | 52 | n.a. |
| Captan | 0.25 | n.a. | 26 | n.a. |
| Chlorothalonil | 1 | n.a. | 40 | n.a. |
| Ex. No. 27 + Chlorothalonil | 4 1 | 4:1 | 98 | 74 |
| Ex. No. 71 + Chlorothalonil | 4 1 | 4:1 | 99 | 73 |
| Ex. No. 203 + Captan | 1 0.25 | 4:1 | 76 | 64 |
| Ex. No. 203 + Chlorothalonil | 4 1 | 4:1 | 99 | 74 |

Use Example 33

Activity Against *Fusarium oxysporum*

A spore suspension of *Fusarium oxysporum* in an aqueous biomalt solution was used.

TABLE XIV

| Compound or mixture tested | Concentration of compounds (ppm) | Mixing ratio | Observed efficacy (%) | Expected efficacy (%) |
|---|---|---|---|---|
| Ex. No. 27 | 16 | n.a. | 13 | n.a. |
| Pyraclostrobin | 0.25 | n.a. | 0 | n.a. |
| Ex. No. 27 + Pyraclostrobin | 16 0.25 | 63:1 | 33 | 13 |

B. Greenhouse

The spray solutions were prepared in several steps:

The stock solution were prepared as follows: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 10 ml. Water was then added to total volume of 100 ml.

This stock solution was diluted with the described solvent-emulsifier-water mixture to the given concentration. The compounds pyraclostrobin, boscalid and epoxiconazole were used as commercial finished formulations and diluted with water to the stated concentration of the active compound.

Use Example 34

Preventative Control of Brown Rust on Wheat Caused by *Puccinia recondita*

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and at temperatures between 20 and 24° C. for 24 h. Then, the plants were cultivated for 6 days in a greenhouse chamber at 20 to 24° C. and a relative humidity between 65 and 70%. The extent of fungal attack on the leaves was visually assessed as % diseased leaf area.

TABLE XV

| Compound or mixture tested | Concentration of compounds (ppm) | Mixing ratio | Observed efficacy (%) | Expected efficacy (%) |
|---|---|---|---|---|
| untreated control | n.a. | n.a. | 90% disease | n.a. |
| Ex. No. 9 | 16 | n.a. | 0 | n.a. |
| Ex. No. 12 | 1 | n.a. | 22 | n.a. |
|  | 0.25 | n.a. | 0 | n.a. |
| Ex. No. 27 | 16 | n.a. | 22 | n.a. |
|  | 4 | n.a. | 0 | n.a. |
| Ex. No. 28 | 1 | n.a. | 0 | n.a. |
| Ex. No. 33 | 16 | n.a. | 33 | n.a. |
| Ex. No. 45 | 16 | n.a. | 0 | n.a. |
|  | 4 | n.a. | 0 | n.a. |
| Ex. No. 64 | 16 | n.a. | 0 | n.a. |
|  | 4 | n.a. | 0 | n.a. |
| Ex. No. 71 | 16 | n.a. | 0 | n.a. |
| Ex. No. 74 | 16 | n.a. | 44 | n.a. |
| Ex. No. 160 | 4 | n.a. | 0 | n.a. |
|  | 1 | n.a. | 0 | n.a. |
| Ex. No. 203 | 16 | n.a. | 44 | n.a. |
|  | 4 | n.a. | 22 | n.a. |
| Epoxiconazol | 1 | n.a. | 33 | n.a. |
|  | 0.25 | n.a. | 0 | n.a. |
|  | 0.063 | n.a. | 0 | n.a. |
| Pyraclostrobin | 0.25 | n.a. | 0 | n.a. |
|  | 0.063 | n.a. | 0 | n.a. |
|  | 0.016 | n.a. | 0 | n.a. |
| Boscalid | 16 | n.a. | 0 | n.a. |
|  | 4 | n.a. | 0 | n.a. |
|  | 1 | n.a. | 0 | n.a. |
|  | 0.25 | n.a. | 0 | n.a. |
| Ex. No. 9 + Boscalid | 16 16 | 1:1 | 22 | 0 |
| Ex. No. 12 + Pyraclostrobin | 1 0.016 | 63:1 | 44 | 22 |
| Ex. No. 12 + Boscalid | 0.25 0.25 | 1:1 | 33 | 0 |
| Ex. No. 27 + Epoxiconazol | 4 0.25 | 1:16 | 56 | 0 |
| Ex. No. 27 + Pyraclostrobin | 4 0.063 | 63:1 | 33 | 0 |
| Ex. No. 27 + Boscalid | 16 16 | 1:1 | 67 | 22 |
| Ex. No. 28 + Epoxiconazol | 1 0.063 | 1:16 | 22 | 0 |
| Ex. No. 33 + Boscalid | 16 16 | 1:1 | 67 | 33 |
| Ex. No. 45 + Epoxiconazol | 4 0.25 | 1:16 | 33 | 0 |
| Ex. No. 45 + Boscalid | 16 16 | 1:1 | 56 | 0 |
| Ex. No. 64 + Epoxiconazol | 4 0.25 | 1:16 | 22 | 0 |
| Ex. No. 45 + Pyraclostrobin | 16 0.25 | 63:1 | 33 | 0 |
| Ex. No. 64 + Pyraclostrobin | 16 0.25 | 63:1 | 22 | 0 |
| Ex. No. 71 + Epoxiconazol | 16 1 | 1:16 | 89 | 33 |
| Ex. No. 71 + Pyraclostrobin | 16 0.25 | 63:1 | 89 | 0 |
| Ex. No. 71 + Boscalid | 16 16 | 1:1 | 89 | 0 |
| Ex. No. 74 + Boscalid | 4 4 | 1:1 | 67 | 44 |
| Ex. No. 160 + Pyraclostrobin | 4 0.063 | 63:1 | 22 | 0 |
| Ex. No. 160 + Boscalid | 1 1 | 1:1 | 22 | 0 |
| Ex. No. 203 + Epoxiconazol | 4 0.25 | 1:16 | 44 | 22 |
| Ex. No. 203 + Pyraclostrobin | 16 0.25 | 63:1 | 89 | 44 |
| Ex. No. 203 + Boscalid | 4 4 | 1:1 | 44 | 22 |

The invention claimed is:

1. A pyridylmethyl-sulfonamide compound of the formula (I)

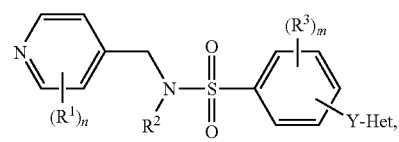

where:
indicates the number of substituents $R^1$ on the pyridine ring and n is 0, 1, 2, 3 or 4;
m indicates the number of substituents $R^3$ on the phenyl ring and m is 0, 1, 2, 3 or 4;
$R^1$ is halogen, CN, $NO_2$, OH, SH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, $C_2$-$C_4$-alkenyl, $C_2$-$C_4$-alkynyl, $C_3$-$C_8$-cycloalkyl or $C_1$-$C_4$-alkyl-$C_3$-$C_8$-cycloalkyl; and/or
two radicals $R^1$ that are bound to adjacent carbon atoms of the pyridine ring may form together with said carbon atoms a fused benzene ring, a fused saturated or partially unsaturated 5-, 6-, or 7-membered carbocycle or a fused 5-, 6-, or 7-membered heterocycle containing 1, 2, or 3 heteroatoms selected from the group consisting of 2 nitrogen atoms, 1 oxygen atom, and 1 sulfur atom as ring members, it being possible for the fused ring to carry 1 or 2 radicals selected from the group consisting of halogen, $C_1$-$C_4$-alkyl, halomethyl, $C_1$-$C_4$-alkoxy and halomethoxy,
it being possible for n=2, 3 or 4 that $R^1$ are identical or different;
$R^2$ is hydrogen, $C_1$-$C_4$-alkyl, $C_1$-$C_4$-haloalkyl, $C_2$-$C_4$-alkenyl, $C_2$-$C_4$-alkynyl, $C_3$-$C_8$-cycloalkyl, $C_1$-$C_4$-alkyl-$C_3$-$C_8$-cycloalkyl or benzyl wherein the phenyl moiety of benzyl group is unsubstituted or carries 1, 2, 3, 4, or 5 substituents selected from the group consisting of cyano, halogen, $C_1$-$C_4$-alkyl, $C_1$-$C_4$-haloalkyl, $C_1$-$C_4$-alkoxy, $C_1$-$C_4$-haloalkoxy, ($C_1$-$C_4$-alkoxy)carbonyl and di($C_1$-$C_4$-alkyl)aminocarbonyl;
$R^3$ is halogen, CN, $NO_2$, $C_1$-$C_4$-alkyl, $C_1$-$C_4$-haloalkyl, $C_1$-$C_4$-alkoxy or $C_1$-$C_4$-haloalkoxy, it being possible for m=2, 3 or 4 that $R^3$ are identical or different;
Y is —O—;
Het is a 5- or 6-membered heteroaromatic radical, wherein the ring member atoms of the heteroaromatic radical include, besides carbon atoms 1, 2, 3 or 4 nitrogen atoms, or 1 oxygen atom and 0, 1 or 2 nitrogen atoms or 1 sulfur atom and 0, 1 or 2 nitrogen atoms and wherein the heteroaromatic radical is unsubstituted or carries 1, 2, 3 or 4 identical or different substituents $R^a$, wherein two radicals $R^a$ that are bound to adjacent ring member atoms may form a fused 5- or 6-membered carbocycle or heterocycle, wherein the fused carbocycle or heterocycle is unsubstituted or carries 1, 2, 3 or 4 identical or different substituents $R^b$;
$R^a$ is halogen, CN, $NO_2$, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$- alkylsulfonyl, $C_1$-$C_4$-haloalkylsulfonyl, amino, $C_1$-$C_4$-alkylamino, di($C_1$-$C_4$-alkyl)amino, $C_1$-$C_4$-alkoxy-$C_1$-$C_4$-alkyl, a radical C(=O)R, wherein R is H, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkoxy, $C_1$-$C_4$-haloalkoxy, amino, $C_1$-$C_4$-alkylamino or di($C_1$-$C_4$-alkyl)amino, a radical CR'(=NOR"), wherein R' is H or $C_1$-$C_4$-alkyl, and R" is $C_1$-$C_4$-alkyl, $C_1$-$C_4$-haloalkyl, $C_2$-$C_4$-alkenyl, $C_2$-$C_4$-alkynyl or $C_1$-$C_4$-alkoxy-$C_1$-$C_4$-alkyl, phenyl, pyridinyl, pyrimidinyl, phenoxy or phenoxyalkyl, where the five last mentioned radicals are unsubstituted or carry 1, 2, 3 or 4 identical or different substituents $R^c$;

$R^b$ and $R^c$ independently of each other are selected from the group consisting of halogen, CN, $NO_2$, OH, SH, $C_1$-$C_4$-alkyl, $C_1$-$C_4$-haloalkyl, $C_1$-$C_4$-alkoxy and $C_1$-$C_4$-haloalkoxy;

and the N-oxides and the agriculturally acceptable salts of the compounds of the formula (I).

2. The compound of claim 1, in which Het is selected from the group consisting of pyridinyl, pyrimidinyl, pyridazinyl, pyrazinyl, thiazolyl, oxazolyl, isothiazolyl, isoxazolyl, thienyl, furyl, 1,3,5-triazinyl, 1,2,4-triazinyl, thiadiazolyl, 1,2,3-triazolyl, 1,2,4-triazolyl, pyrazolyl, and imidazolyl, wherein the aforementioned heteroaromatic radicals are unsubstituted or carry 1, 2, 3 or 4 identical or different substituents $R^a$.

3. The compound of claim 1, wherein the moiety Het-Y is located on the phenyl ring in the para-position with respect to the sulfonyl group.

4. The compound of claim 1, wherein Het is pyridin-2-yl, which is unsubstituted or carries 1 or 2 radicals $R^a$.

5. The compound of claim 4, wherein Het is selected from the group consisting of 3-trifluoromethylpyridin-2-yl, 5-trifluoromethylpyridin-2-yl, 4-trifluoromethylpyridin-2-yl, 3-chloropyridin-2-yl, 5-chloropyridin-2-yl, 4-chloropyridin-2-yl, 3-bromopyridin-2-yl, 5-bromopyridin-2-yl, 4-bromopyridin-2-yl, 3-trichloromethylpyridin-2-yl, 5-trichloromethylpyridin-2-yl, 4-trichloromethylpyridin-2-yl, 3-cyanopyridin-2-yl, 5-cyanopyridin-2-yl, 4-cyanopyridin-2-yl, 3-nitropyridin-2-yl, 5-nitropyridin-2-yl, 4-nitropyridin-2-yl, 3-methylsulfonylpyridin-2-yl, 5-methylsulfonylpyridin-2-yl, 4-methylsulfonylpyridin-2-yl, 3-ethylsulfonylpyridin-2-yl, 5-ethylsulfonylpyridin-2-yl, 4-ethylsulfonylpyridin-2-yl, 3-methoxycarbonylpyridin-2-yl, 5-methoxycarbonylpyridin-2-yl, 4-methoxycarbonylpyridin-2-yl, 5-aminocarbonylpyridin-2-yl, 4-aminocarbonylpyridin-2-yl, 3-aminocarbonylpyridin-2-yl, 5-N-methylaminocarbonylpyridin-2-yl, 4-N-methylaminocarbonylpyridin-2-yl, 3-N-methylaminocarbonylpyridin-2-yl, 3-methoxypyridin-2-yl, 3-ethoxypyridin-2-yl, 3-difluoromethoxypyridin-2-yl, 5-methoxypyridin-2-yl, 5-ethoxypyridin-2-yl, 5-difluoromethoxypyridin-2-yl, 3-chloro-5-trifluoromethylpyridin-2-yl, 3-fluoro-5-trifluoromethylpyridin-2-yl, 3-bromo-5-trifluoromethylpyridin-2-yl, 3-methyl-5-trifluoromethylpyridin-2-yl, 3-ethyl-5-trifluoromethylpyridin-2-yl, 3-chloro-5-difluoromethoxypyridin-2-yl, 3-fluoro-5-difluoromethoxypyridin-2-yl, 3-methyl-5-difluoromethoxypyridin-2-yl, 3-chloro-5-trichloromethylpyridin-2-yl, 3-fluoro-5-trichloromethylpyridin-2-yl, 3-chloro-5-cyanopyridin-2-yl, 3-fluoro-5-cyanopyridin-2-yl, 3-methyl-5-cyanopyridin-2-yl, 3-ethyl-5-cyanopyridin-2-yl, 3-chloro-5-nitropyridin-2-yl, 3-chloro-5-methoxycarbonylpyridin-2-yl, 3-chloro-5-aminocarbonylpyridin-2-yl, 3-chloro-5-methylaminocarbonylpyridin-2-yl, 3-fluoro-5-nitropyridin-2-yl, 3-fluoro-5-methoxycarbonylpyridin-2-yl, 3-fluoro-5-aminocarbonylpyridin-2-yl, 3-fluoro-5-methylaminocarbonylpyridin-2-yl, 4-chloro-5-trifluoromethylpyridin-2-yl, 4-fluoro-5-trifluoromethylpyridin-2-yl, 4-bromo-5-trifluoromethylpyridin-2-yl, 4-methyl-5-trifluoromethylpyridin-2-yl, 4-chloro-5-nitropyridin-2-yl, 4-chloro-5-cyanopyridin-2-yl, 3-chloro-6-trifluoromethylpyridin-2-yl, 3-fluoro-6-trifluoromethylpyridin-2-yl, 3-methyl-6-trifluoromethylpyridin-2-yl, 4-chloro-5-difluoromethoxypyridin-2-yl, 4-fluoro-5-difluoromethoxypyridin-2-yl, 3-chloro-5-bromopyridin-2-yl, 3,5-dichloropyridin-2-yl, 3,5-difluoropyridin-2-yl, 3,5-dibromopyridin-2-yl, 3-methyl-5-chloropyridin-2-yl, 3-methyl-5-fluoropyridin-2-yl, 3-methyl-5-bromopyridin-2-yl, 3-methoxy-5-trifluoromethylpyridin-2-yl, 3-methoxy-5-cyanopyridin-2-yl, 3-methoxy-5-nitropyridin-2-yl, 3-methoxy-5-difluoromethoxypyridin-2-yl, 3-ethoxy-5-trifluoromethylpyridin-2-yl, 3-ethoxy-5-cyanopyridin-2-yl, 3-ethoxy-5-nitropyridin-2-yl, 3-ethoxy-5-difluoromethoxypyridin-2-yl, 3-chloro-4-methyl-5-trifluoromethylpyridin-2-yl and 3,4-dichloro-5-trifluoromethylpyridin-2-yl.

6. A process for preparing a compound of claim 1, which comprises reacting an aminomethylpyridine compound of the formula (II)

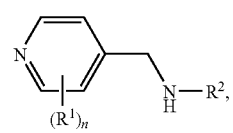

(II)

under basic conditions with a sulfonic acid derivative of the formula (III)

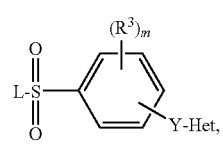

(III)

wherein L is a leaving group selected from the group consisting of halogen, hydroxy, azido, optionally substituted heteroaryl, optionally substituted heteroaryloxy or optionally substituted phenoxy.

7. A process for preparing a compound of claim 1, which comprises reacting a compound of the formula (IV)

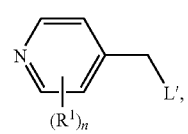

(IV)

wherein L' is a leaving group,
under basic conditions with compound (III.a)

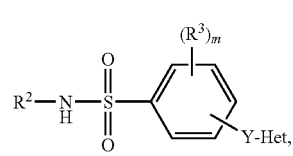

(III.a)

wherein n, $R^1$, Y, Het, m, $R^2$ and $R^3$ are as defined in claim 1.

8. A compound of the formula (II)

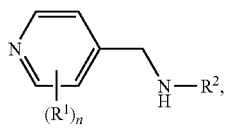

wherein $R^2$ is hydrogen, $C_1$-$C_2$-alkyl, —CH=CH$_2$ or —CH$_2$—C≡CH, n is 2 and $R^1$ is in position 2 and 3 of the pyridine ring and is selected from halogen, $C_1$-$C_2$-alkyl, $C_1$-$C_2$-alkoxy, $C_1$-$C_2$-haloalkyl or $C_1$-$C_2$-haloalkoxy and wherein $R^1$ in position 2 is different from $R^1$ in position 3 and if one of both $R^1$ is $CH_3$, the other $R^1$ is not $OCH_3$.

9. A compound of the formula (III)

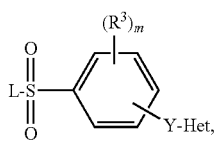

wherein $R^3$, Y and Het are defined as in claim 1, L is halogen and m is 1, 2, 3 or 4.

10. A compound of the formula (III), wherein L is halogen, $R^3$ is $CH_3$, m is 0, 1 or 2, Y is —O—, the moiety Y-Het is located on the phenyl ring in the para-position in respect to the sulfonyl group, Het is pyridin-4-yl that carries 2 radicals $R^a$ which are selected from F, Cl, Br, $CH_3$, $CHF_2$, $OCH_3$, $OCF_3$, $OCHF_2$ and $SCH_3$.

11. An agricultural composition which comprises a solvent or solid carrier and at least one compound of the formula (I) or an N-oxide or an agriculturally acceptable salt thereof, according to claim 1.

12. The composition according to claim 11, comprising at least one further active substance.

13. A method for combating phytopathogenic harmful fungi, which process comprises treating the fungi or the materials, plants, the soil or seeds to be protected against fungal attack, with an effective amount of at least one compound of the formula (I) of an or an N-oxide or an agriculturally acceptable salt thereof, according to claim 1.

14. A seed treated with a compound of the formula (I), or an N-oxide or an agriculturally acceptable salt thereof, as defined in claim 1, in an amount of from 0.1 g to 10 kg per 100 kg of seed.

15. The process of claim 6, wherein L' is methylsulfonyl or toluenesulfonyl.

16. The method of claim 6, wherein L' is chloro, fluoro, optionally substituted pyrazol-1-yl, optionally substituted imidazol-1-yl, optionally substituted 1,2,3-triazol-1-yl, optionally substituted 1,2,4-triazol-1-yl, pentafluorphenoxy or hydroxybenzotriazoloxy.

* * * * *